(12) United States Patent
Sun et al.

(10) Patent No.: US 11,254,745 B1
(45) Date of Patent: Feb. 22, 2022

(54) ANTI-CD4 ANTIBODIES

(71) Applicant: Crown Bioscience Inc., San Diego, CA (US)

(72) Inventors: Ziyong Sun, Taicang (CN); Wencui Ma, Taicang (CN); Hongli Ma, Taicang (CN); Qian (Nicole) Niu, San Diego, CA (US); Ying Jin, Taicang (CN); Wen Yu, Taicang (CN); Huanhuan Zhang, Taicang (CN); Chengcheng Wang, Taicang (CN); Yangzhou Wang, San Diego, CA (US); Jean Pierre Wery, San Diego, CA (US)

(73) Assignee: CROWN BIOSCIENCE INC., San Diego, CA (US)

( * ) Notice: Subject to any disclaimer, the term of this patent is extended or adjusted under 35 U.S.C. 154(b) by 0 days.

(21) Appl. No.: 17/315,343

(22) Filed: May 9, 2021

(30) Foreign Application Priority Data

Apr. 7, 2021 (CN) .......................... 202110373640.7

(51) Int. Cl.
| | |
|---|---|
| *C07K 16/28* | (2006.01) |
| *A61K 45/06* | (2006.01) |
| *A61K 39/395* | (2006.01) |
| *A61K 31/436* | (2006.01) |
| *A61K 47/68* | (2017.01) |

(52) U.S. Cl.
CPC ........ *C07K 16/2812* (2013.01); *A61K 31/436* (2013.01); *A61K 39/3955* (2013.01); *A61K 45/06* (2013.01); *A61K 47/6849* (2017.08); *C07K 16/2803* (2013.01); *C07K 16/2809* (2013.01); *C07K 2317/24* (2013.01); *C07K 2317/31* (2013.01); *C07K 2317/52* (2013.01); *C07K 2317/565* (2013.01); *C07K 2317/732* (2013.01); *C07K 2317/734* (2013.01); *C07K 2317/76* (2013.01); *C07K 2317/92* (2013.01)

(58) Field of Classification Search
CPC ...................... C07K 2317/565; C07K 16/2812
USPC ............................................ 424/133.1, 136.1
See application file for complete search history.

(56) References Cited

U.S. PATENT DOCUMENTS

| | | | |
|---|---|---|---|
| 10,442,862 B2 * | 10/2019 | Yang ................ | A61K 39/39558 |
| 2010/0310573 A1 | 12/2010 | Nakagawa et al. | |
| 2015/0283269 A1 * | 10/2015 | An ...................... | A61K 33/243 800/11 |
| 2016/0024216 A1 * | 1/2016 | Yang ................ | A61K 39/39558 424/133.1 |
| 2017/0007698 A1 | 1/2017 | Kim et al. | |

FOREIGN PATENT DOCUMENTS

CN 102898525 A 1/2013

OTHER PUBLICATIONS

The First Office Action of the corresponding CN application 202110373640.7, dated Aug. 30, 2021.

* cited by examiner

*Primary Examiner* — Lynn A Bristol
(74) *Attorney, Agent, or Firm* — Jun He Law Offices P.C.; Yi Zhang

(57) ABSTRACT

The present disclosure provides herein anti-CD4 antibodies or antigen-binding fragments thereof, isolated polynucleotides encoding the same, pharmaceutical compositions comprising the same, and the uses thereof.

27 Claims, 4 Drawing Sheets

Specification includes a Sequence Listing.

ANTI-CD4 ANTIBODIES

CROSS-REFERENCE TO RELATED APPLICATIONS

The present application claims the priority of Chinese Patent Application No. 202110373640.7, filed Apr. 7, 2021, the disclosure of which is incorporated herein by reference in the entirety.

SEQUENCE LISTING

The sequence listing that is contained in the file named "056211-8004US01_SL_ST25", which is 38 KB (as measured in Microsoft Windows) and was created on May 25, 2021, is filed herewith by electronic submission and is incorporated by reference herein.

BACKGROUND

1. Field of the Invention

The present disclosure generally relates to antibodies and antigen-binding fragments thereof that bind to human CD4, and to methods of using such antibodies and antigen-binding fragments.

2. Description of Related Art

CD4 is a monomeric type I transmembrane glycoprotein and a member of the immunoglobulin supergene family, and it comprises four extracellular Ig-like domains, a hydrophobic transmembrane domain, and a highly basic cytoplasmic tail (Glatzova D, et al., Front Immunol (2019) 10: 618). The N-terminal Ig-like domains of CD4 interact with the α2 and β2 domains of MHC class II molecules to assemble TCR-pMHC-CD4 ternary complex, and the resulting close proximity between the TCR and CD4 allows the tyrosine kinase Lck bound to the cytoplasmic tail of CD4 to phosphorylate tyrosine residues of immunoreceptor tyrosine activation motifs (ITAMs) on the cytoplasmic domains of CD3 to amplify the signal generated by the TCR (Rudd C E, et al., Proc Natl Acad Sci USA (1988) 85: 5190; Barber E K, et al., Proc Natl Acad Sci USA (1989) 86: 3277 and Li Q J, et al., Nat Immunol (2004) 5: 791).

CD4 is expressed in a large proportion of thymocytes (80-90%) and over 50% of the peripheral blood T-cells (Nakamura K, et al., Mol Immunol (2003) 39: 909). CD4 is also expressed to a minor extent on macrophages, monocytes, dendritic cells and Langerhans cells. CD4 plays an important role not only in the differentiation of thymocytes and the regulation of T-lymphocyte/B-lymphocyte adhesion, but also in MHC class II-restricted T cell activation (Gaubin M, et al., Eur J Clin Chem Clin Biochem (1996) 34: 723; Artyomov M N, et al., Proc Natl Acad Sci USA (2010) 107: 16916; Yili L, et al., Front Immunol (2013) 4: 206).

More importantly, CD4 expressing cells, such as regulatory T cells (Tregs) have been shown to suppress tumor-induced immunity, thereby compromising the therapeutic efficacy of various cancer therapies (Baba J, et al., Blood (2012) 120: 2417; Togashi Y, et al., Nature Reviews Clinical Oncology (2019) 16: 356). Therefore, there is a need for novel anti-CD4 antibodies that can effectively target and eliminate the CD4-expressing cells, especially Tregs.

BRIEF SUMMARY OF THE INVENTION

Throughout the present disclosure, the articles "a," "an," and "the" are used herein to refer to one or to more than one (i.e., to at least one) of the grammatical object of the article. By way of example, "an antibody" means one antibody or more than one antibody.

The present disclosure provides, among others, an isolated antibody against human CD4 (hCD4) or an antigen-binding fragment thereof, comprising a heavy chain variable (VH) region and/or a light chain variable (VL) region, wherein the heavy chain variable region comprises:
  a) a HCDR1 comprises a sequence selected from the group consisting of SEQ ID NOs: 1, 11, 21, 31 and 41,
  b) a HCDR2 comprises a sequence selected from the group consisting of SEQ ID NOs: 2, 12, 22 and 42, and
  c) a HCDR3 comprises a sequence selected from the group consisting of SEQ ID NOs: 3, 13, 23, 33 and 43, and/or
wherein the light chain variable region comprises:
  d) a LCDR1 comprises a sequence selected from the group consisting of SEQ ID NOs: 4, 14, 24 and 34,
  e) a LCDR2 comprises a sequence selected from the group consisting of SEQ ID NOs: 5, 15 and 25, and
  f) a LCDR3 comprises a sequence selected from the group consisting of SEQ ID NOs: 6, 16, 26 and 46.

In certain embodiments, the heavy chain variable region is selected from the group consisting of:
  a) a heavy chain variable region comprising a HCDR1 comprising the sequence of SEQ ID NO: 1, a HCDR2 comprising the sequence of SEQ ID NO: 2, and a HCDR3 comprising the sequence of SEQ ID NO: 3;
  b) a heavy chain variable region comprising a HCDR1 comprising the sequence of SEQ ID NO: 11, a HCDR2 comprising the sequence of SEQ ID NO: 12, and a HCDR3 comprising the sequence of SEQ ID NO: 13;
  c) a heavy chain variable region comprising a HCDR1 comprising the sequence of SEQ ID NO: 21, a HCDR2 comprising the sequence of SEQ ID NO: 22, and a HCDR3 comprising the sequence of SEQ ID NO: 23;
  d) a heavy chain variable region comprising a HCDR1 comprising the sequence of SEQ ID NO: 31, a HCDR2 comprising the sequence of SEQ ID NO: 2, and a HCDR3 comprising the sequence of SEQ ID NO: 33; and
  e) a heavy chain variable region comprising a HCDR1 comprising the sequence of SEQ ID NO: 41, a HCDR2 comprising the sequence of SEQ ID NO: 42, and a HCDR3 comprising the sequence of SEQ ID NO: 43.

In certain embodiments, the light chain variable region is selected from the group consisting of:
  a) a light chain variable region comprising a LCDR1 comprising the sequence of SEQ ID NO: 4, a LCDR2 comprising the sequence of SEQ ID NO: 5, and a LCDR3 comprising the sequence of SEQ ID NO: 6;
  b) a light chain variable region comprising a LCDR1 comprising the sequence of SEQ ID NO: 14, a LCDR2 comprising the sequence of SEQ ID NO: 15, and a LCDR3 comprising the sequence of SEQ ID NO: 16;
  c) a light chain variable region comprising a LCDR1 comprising the sequence of SEQ ID NO: 24, a LCDR2 comprising the sequence of SEQ ID NO: 25, and a LCDR3 comprising the sequence of SEQ ID NO: 26;
  d) a light chain variable region comprising a LCDR1 comprising the sequence of SEQ ID NO: 34, a LCDR2 comprising the sequence of SEQ ID NO: 5, and a LCDR3 comprising the sequence of SEQ ID NO: 6; and
  e) a light chain variable region comprising a LCDR1 comprising the sequence of SEQ ID NO: 24, a LCDR2 comprising the sequence of SEQ ID NO: 25, and a LCDR3 comprising the sequence of SEQ ID NO: 46.

In certain embodiments, the antibody or an antigen-binding fragment thereof provided herein comprises:
- a) a heavy chain variable region comprises a HCDR1 comprising the sequence of SEQ ID NO: 1, a HCDR2 comprising the sequence of SEQ ID NO: 2, and a HCDR3 comprising the sequence of SEQ ID NO: 3; and a light chain variable region comprises a LCDR1 comprising the sequence of SEQ ID NO: 4, a LCDR2 comprising the sequence of SEQ ID NO: 5, and a LCDR3 comprising the sequence of SEQ ID NO: 6;
- b) a heavy chain variable region comprises a HCDR1 comprising the sequence of SEQ ID NO: 11, a HCDR2 comprising the sequence of SEQ ID NO: 12, and a HCDR3 comprising the sequence of SEQ ID NO: 13; and a light chain variable region comprises a LCDR1 comprising the sequence of SEQ ID NO: 14, a LCDR2 comprising the sequence of SEQ ID NO: 15, and a LCDR3 comprising the sequence of SEQ ID NO: 16;
- c) a heavy chain variable region comprises a HCDR1 comprising the sequence of SEQ ID NO: 21, a HCDR2 comprising the sequence of SEQ ID NO: 22, and a HCDR3 comprising the sequence of SEQ ID NO: 23; and a light chain variable region comprises a LCDR1 comprising the sequence of SEQ ID NO: 24, a LCDR2 comprising the sequence of SEQ ID NO: 25, and a LCDR3 comprising the sequence of SEQ ID NO: 26;
- d) a heavy chain variable region comprises a HCDR1 comprising the sequence of SEQ ID NO: 31, a HCDR2 comprising the sequence of SEQ ID NO: 2, and a HCDR3 comprising the sequence of SEQ ID NO: 33; and a light chain variable region comprises a LCDR1 comprising the sequence of SEQ ID NO: 34, a LCDR2 comprising the sequence of SEQ ID NO: 5, and a LCDR3 comprising the sequence of SEQ ID NO: 6; or
- e) a heavy chain variable region comprises a HCDR1 comprising the sequence of SEQ ID NO: 41, a HCDR2 comprising the sequence of SEQ ID NO: 42, and a HCDR3 comprising the sequence of SEQ ID NO: 43; and a light chain variable region comprises a LCDR1 comprising the sequence of SEQ ID NO: 24, a LCDR2 comprising the sequence of SEQ ID NO: 25, and a LCDR3 comprising the sequence of SEQ ID NO: 46.

In certain embodiments, the heavy chain variable region comprises a sequence selected from the group consisting of SEQ ID NO: 7, SEQ ID NO: 17, SEQ ID NO: 27, SEQ ID NO: 37, SEQ ID NO: 47, SEQ ID NO: 61, and SEQ ID NO: 63, and a homologous sequence thereof having at least 80% sequence identity yet retaining specific binding specificity or affinity to CD4.

In certain embodiments, the light chain variable region comprises a sequence selected from the group consisting of SEQ ID NO: 8, SEQ ID NO: 18, SEQ ID NO: 28, SEQ ID NO: 38, SEQ ID NO: 48, SEQ ID NO: 62, and SEQ ID NO: 64, and a homologous sequence thereof having at least 80% sequence identity yet retaining specific binding specificity or affinity to CD4.

In certain embodiments, the antibody or an antigen-binding fragment thereof provided herein comprises:
- a) a heavy chain variable region comprising the sequence of SEQ ID NO: 7 and a light chain variable region comprising the sequence of SEQ ID NO: 8; or
- b) a heavy chain variable region comprising a sequence of SEQ ID NO: 17 and a light chain variable region comprising a sequence of SEQ ID NO: 18; or
- c) a heavy chain variable region comprising a sequence of SEQ ID NO: 27 and a light chain variable region comprising a sequence of SEQ ID NO: 28; or
- d) a heavy chain variable region comprising a sequence of SEQ ID NO: 37 and a light chain variable region comprising a sequence of SEQ ID NO: 38; or
- e) a heavy chain variable region comprising a sequence of SEQ ID NO: 47 and a light chain variable region comprising a sequence of SEQ ID NO: 48; or
- f) a heavy chain variable region comprising a sequence of SEQ ID NO: 61 and a light chain variable region comprising a sequence of SEQ ID NO: 62; or
- g) a heavy chain variable region comprising a sequence of SEQ ID NO: 63 and a light chain variable region comprising a sequence of SEQ ID NO: 64.

In another aspect, the present disclosure provides an isolated antibody against human CD4 (hCD4) or an antigen-binding fragment thereof, comprising: a heavy chain variable region comprising the sequence of SEQ ID NO: 65 and a light chain variable region comprising the sequence of SEQ ID NO: 66, and a homologous sequence thereof having at least 80% sequence identity yet retaining specific binding specificity or affinity to CD4.

In certain embodiments, the antibody or antigen-binding fragment thereof provided herein further comprises one or more amino acid residue substitutions or modifications yet retains specific binding specificity or affinity to hCD4.

In certain embodiments, at least one of the substitutions or modifications is in one or more of the CDR sequences, and/or in one or more of the non-CDR regions of the VH or VL sequences.

In certain embodiments, the antibody or antigen-binding fragment thereof provided herein further comprises an immunoglobulin constant region, optionally a constant region of human Ig, or optionally a constant region of human IgG.

In certain embodiments, the constant region comprises a constant region of human IgG1, IgG2, IgG3, or IgG4.

In certain embodiments, the constant region comprises a constant region of human IgG1.

In certain embodiments, the IgG1 comprises one or more mutations that can confer increased CDC or ADCC relative to wild-type constant region.

In certain embodiments, the one or more mutations is selected from the group consisting of S239D, I332E, H268F, S324T S236A, G236A, P247I, A339(D/Q), D280H, K290S, S298 (D/V), F243L, R292P, Y300L, P396L, V305I, K290 (E/N), S298G, T299A, K326E, E382V, M428I, S298A, K326A, E333A, K334A, S298A, E333A, and K334A, according to EU numbering.

In certain embodiments, the one or more mutations comprise a combination of S298A, E333A, and K334A, according to EU numbering.

In certain embodiments, the antibody or an antigen-binding fragment thereof provided herein is humanized.

In certain embodiments, the antibody or antigen-binding fragment thereof provided herein is a diabody, a Fab, a Fab', a F(ab')$_2$, a Fd, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), an scFv dimer (bivalent diabody), a multispecific antibody, a camelized single domain antibody, a nanobody, a domain antibody, and a bivalent domain antibody.

In certain embodiments, the antibody or antigen-binding fragment thereof provided herein is bispecific.

In certain embodiments, the antibody or antigen-binding fragment thereof provided herein is capable of specifically binding to a first and a second epitope of hCD4, or capable of specifically binding to both hCD4 and a second antigen.

In certain embodiments, the second antigen comprises an immune related target.

In certain embodiments, the second antigen comprises PD-1, PD-L1, PD-L2, CTLA-4, TIM-3, LAG3, A2AR, CD160, 2B4, TGF β, VISTA, BTLA, TIGIT, LAIR1, OX40, CD2, CD27, CD28, CD30, CD40, CD47, CD122, ICAM-1, IDO, NKG2C, SLAMF7, SIGLEC7, NKp80, CD160, B7-H3, LFA-1, 1COS, 4-1BB, GITR, BAFFR, HVEM, CD7, LIGHT, IL-2, IL-7, IL-15, IL-21, CD3, CD16 or CD83.

In certain embodiments, the second antigen comprises a tumor antigen.

In certain embodiments, the tumor antigen comprises a tumor specific antigen or a tumor associated antigen.

In certain embodiments, the tumor antigen comprises prostate specific antigen (PSA), CA-125, gangliosides G(D2), G(M2) and G(D3), CD20, CD52, CD33, Ep-CAM, CEA, bombesin-like peptides, HER2/neu, epidermal growth factor receptor (EGFR), erbB2, erbB3/HER3, erbB4, CD44v6, Ki-67, cancer-associated mucin, VEGF, VEGFRs (e.g., VEGFR-1, VEGFR-2, VEGFR-3), estrogen receptors, Lewis-Y antigen, TGF-beta1, IGF-1 receptor, EGF, c-Kit receptor, transferrin receptor, Claudin 18.2, GPC-3, Nectin-4, ROR1, methothelin, PCMA, MAGE-1, MAGE-3, BAGE, GAGE-1, GAGE-2, p15, BCR-ABL, E2APRL, H4-RET, IGH-IGK, MYL-RAR, IL-2R, CO17-1A, TROP2, or LIV-1.

In certain embodiments, the antibody or antigen-binding fragment thereof provided herein is linked to one or more conjugate moieties.

In certain embodiments, the conjugate moiety comprises a clearance-modifying agent, a chemotherapeutic agent, a toxin, a radioactive isotope, a lanthanide, a luminescent label, a fluorescent label, an enzyme-substrate label, a DNA-alkylator, a topoisomerase inhibitor, a tubulin-binders, or other anticancer drugs such as androgen receptor inhibitor.

In another aspect, the present disclosure provides an antibody or an antigen-binding fragment thereof, which competes for binding to hCD4 with the antibody or antigen-binding fragment thereof provided herein.

In another aspect, the present disclosure provides a pharmaceutical composition or kit comprising the antibody or antigen-binding fragment thereof provided herein, and a pharmaceutically acceptable carrier.

In certain embodiments, the pharmaceutical composition or kit provided herein further comprises a second therapeutic agent.

In certain embodiments, the second therapeutic agent comprises an anti-cancer agent, such as a mTOR inhibitor, an immune checkpoint inhibitor and a T cell-recruiting antibody.

In certain embodiments, the mTOR inhibitor is Temsirolimus, Evirolimus or Rapamycin.

In certain embodiments, the immune checkpoint inhibitor is selected from an PD-1 antibody, PD-L1 antibody, PD-L2 antibody, LAG-3 antibody, TIM-1 antibody, CTLA-4 antibody, VISTA antibody, B7-H2 antibody, B7-H3 antibody, B7-H4 antibody, B7-H antibody 6, ICOS antibody, HVEM antibody, CD160 antibody, gp49B antibody, PIR-B antibody, KIR family receptors antibody, TIM-1 antibody, TIM-4 antibody, BTLA antibody, SIRPalpha (CD47) antibody, CD244 antibody, B7.1 antibody, B7.2 antibody, ILT-2 antibody, ILT-4 antibody, TIGIT antibody and A2aR antibody.

In certain embodiments, the T cell-recruiting antibody comprises a CD19/CD3 bispecific antibody.

In another aspect, the present disclosure provides an isolated polynucleotide encoding the antibody or an antigen-binding fragment thereof provided herein.

In another aspect, the present disclosure provides a vector comprising the isolated polynucleotide provided herein.

In another aspect, the present disclosure provides a host cell comprising the vector provided herein.

In another aspect, the present disclosure provides a method of expressing the antibody or antigen-binding fragment thereof provided herein, comprising culturing the host cell under the condition at which the vector is expressed.

In another aspect, the present disclosure provides a method of treating a CD4-related disease or condition in a subject, comprising administering to the subject a therapeutically effective amount of the antibody or antigen-binding fragment thereof or the pharmaceutical composition provided herein.

In certain embodiments, the CD4-related disease or condition is cancer, adaptive immune disease, autoimmune disease, inflammatory disease, or infectious disease.

In certain embodiments, the cancer is selected from the group consisting of lung cancer, bronchial cancer, bone cancer, liver and bile duct cancer, pancreatic cancer, breast cancer, liver cancer, ovarian cancer, testicle cancer, kidney cancer, bladder cancer, head and neck cancer, spine cancer, brain cancer, cervix cancer, uterine cancer, endometrial cancer, colon cancer, colorectal cancer, rectal cancer, anal cancer, esophageal cancer, gastrointestinal cancer, skin cancer, prostate cancer, pituitary cancer, stomach cancer, vagina cancer, thyroid cancer, glioblastoma, astrocytoma, melanoma, myelodysplastic syndrome, sarcoma, teratoma, adenocarcinoma, leukemia (e.g., chronic lymphocytic leukemia, relapsed or refractory B-cell precursor acute lymphoblastic leukemia), myeloma and lymphoma.

In another aspect, the present disclosure provides a method of detecting presence or amount of CD4 in a sample, comprising contacting the sample with the antibody or antigen-binding fragment thereof provided herein, and determining the presence or the amount of CD4 in the sample.

In another aspect, the present disclosure provides a method of diagnosing a CD4-related disease or condition in a subject, comprising: a) obtaining a sample from the subject; b) contacting the sample obtained from the subject with the antibody or antigen-binding fragment thereof provided herein; c) determining presence or amount of CD4 in the sample; and d) correlating the presence or the amount of CD4 to existence or status of the CD4 related disease or condition in the subject.

In another aspect, the present disclosure provides a method of eliminating CD4-expressing cells in a subject in need thereof, comprising administering to the subject a therapeutically effective amount of the antibody or antigen-binding fragment thereof or the pharmaceutical composition provided herein.

In certain embodiments, the CD4-expressing cell is regulatory T cell (Tregs).

In another aspect, the present disclosure provides a method of enhancing immunogenicity of tumor microenvironment in a subject in need thereof, comprising administering to the subject a therapeutically effective amount of the antibody or antigen-binding fragment thereof or the pharmaceutical composition provided herein.

In another aspect, the present disclosure provides a method of improving the therapeutic efficacy of immunotherapy in a subject in need thereof, comprising administering to the subject a therapeutically effective amount of the antibody or antigen-binding fragment thereof or the pharmaceutical composition provided herein.

In certain embodiments, the method provided herein further comprises administering a second therapeutic agent.

In certain embodiments, the second therapeutic agent comprises an anti-cancer agent, such as a mTOR inhibitor, an immune checkpoint inhibitor and a T cell-recruiting antibody.

In certain embodiments, the T cell-recruiting antibody comprises a CD19/CD3 bispecific antibody.

In another aspect, the present disclosure provides use of the antibody or antigen-binding fragment thereof provided herein in the manufacture of a medicament for treating a CD4-related disease or condition in a subject.

In another aspect, the present disclosure provides use of the antibody or antigen-binding fragment thereof provided herein in the manufacture of a medicament for enhancing immunogenicity of tumor microenvironment in a subject in need thereof.

In another aspect, the present disclosure provides use of the antibody or antigen-binding fragment thereof provided herein in the manufacture of a medicament for improving the therapeutic efficacy of immunotherapy in a subject in need thereof.

DETAILED DESCRIPTION OF THE INVENTION

Figure 1:
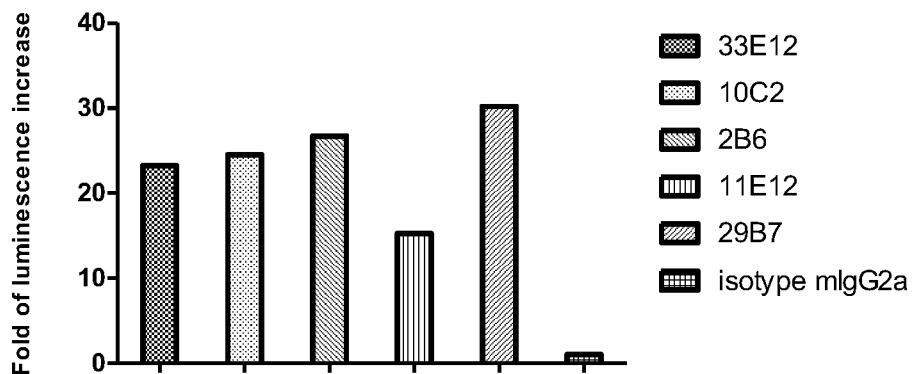
FIG. 1 shows the effect of murine hybridoma anti-CD4 antibodies on 293T-CD16-NFκB gene reporter assay.

The following description of the disclosure is merely intended to illustrate various embodiments of the disclosure. As such, the specific modifications discussed are not to be construed as limitations on the scope of the disclosure. It will be apparent to one skilled in the art that various equivalents, changes, and modifications may be made without departing from the scope of the disclosure, and it is understood that such equivalent embodiments are to be included herein. All references cited herein, including publications, patents and patent applications are incorporated herein by reference in their entirety.

I. Definitions

As used herein, the term "a," "an," "the" and similar terms used in the context of the present invention (especially in the context of the claims) are to be construed to cover both the singular and plural unless otherwise indicated herein or clearly contradicted by the context.

The term "antibody" as used herein includes any immunoglobulin, monoclonal antibody, polyclonal antibody, multivalent antibody, bivalent antibody, monovalent antibody, multi specific antibody, or bispecific antibody that binds to a specific antigen. A native intact antibody comprises two heavy (H) chains and two light (L) chains. Mammalian heavy chains are classified as alpha, delta, epsilon, gamma, and mu, each heavy chain consists of a variable region ($V_H$) and a first, second, and third constant region ($C_{H1}$, $C_{H2}$, $C_{H3}$, respectively); mammalian light chains are classified as λ or κ, while each light chain consists of a variable region ($V_L$) and a constant region. The antibody has a "Y" shape, with the stem of the Y consisting of the second and third constant regions of two heavy chains bound together via disulfide bonding. Each arm of the Y includes the variable region and first constant region of a single heavy chain bound to the variable and constant regions of a single light chain. The variable regions of the light and heavy chains are responsible for antigen binding. The variable regions in both chains generally contain three highly variable loops called the complementarity determining regions (CDRs) (light chain CDRs including LCDR1, LCDR2, and LCDR3, heavy chain CDRs including HCDR1, HCDR2, HCDR3). CDR boundaries for the antibodies and antigen-binding domains disclosed herein may be defined or identified by the conventions of Kabat, IMGT, AbM, Chothia, or Al-Lazikani (Al-Lazikani, B., Chothia, C., Lesk, A. M., J. Mol. Biol., 273(4), 927 (1997); Chothia, C. et al., J Mol Biol. December 5; 186(3):651-63 (1985); Chothia, C. and Lesk, A. M., J. Mol. Biol., 196,901 (1987); N. R. Whitelegg et al, Protein Engineering, v13(12), 819-824 (2000); Chothia, C. et al., Nature. December 21-28; 342(6252):877-83 (1989); Kabat E. A. et al., National Institutes of Health, Bethesda, Md. (1991); Marie-Paule Lefranc et al, Developmental and Comparative Immunology, 27: 55-77 (2003); Marie-Paule Lefranc et al, Immunome Research, 1(3), (2005); Marie-Paule Lefranc, Molecular Biology of B cells (second edition), chapter 26, 481-514, (2015)). The three CDRs are interposed between flanking stretches known as framework regions (FRs), which are more highly conserved than the CDRs and form a scaffold to support the hypervariable loops. The constant regions of the heavy and light chains are not involved in antigen-binding, but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of alpha, delta, epsilon, gamma, and mu heavy chains, respectively. Several of the major antibody classes are divided into subclasses such as IgG1 (gamma1 heavy chain), IgG2 (gamma2 heavy chain), IgG3 (gamma3 heavy chain), IgG4 (gamma4 heavy chain), IgA1 (alpha1 heavy chain), or IgA2 (alpha2 heavy chain). In certain embodiments, the antibody provided herein encompasses any antigen-binding fragments thereof.

As used herein, the term "antigen-binding fragment" refers to an antibody fragment formed from a fragment of an antibody comprising one or more CDRs, or any other antibody portion that binds to an antigen but does not comprise an intact native antibody structure. Examples of antigen-binding fragment include, without limitation, a diabody, a Fab, a Fab', a F(ab)$_2$, a Fd, an Fv fragment, a disulfide stabilized Fv fragment (dsFv), a (dsFv)$_2$, a bispecific dsFv (dsFv-dsFv'), a disulfide stabilized diabody (ds diabody), a single-chain variable fragment (scFv), an scFv dimer (bivalent diabody), a multispecific antibody, a camelized single domain antibody, a nanobody, a domain antibody, and a bivalent domain antibody. An antigen-binding fragment is capable of binding to the same antigen to which the parent antibody binds. In certain embodiments, an antigen-binding fragment may comprise one or more CDRs from a particular parent antibody.

"Fab" or "F(ab)" with regard to an antibody refers to a monovalent antigen-binding fragment of the antibody consisting of a single light chain (both variable and constant regions) bound to the variable region and first constant region of a single heavy chain by a disulfide bond. Fab can be obtained by papain digestion of an antibody at the residues proximal to the N-terminus of the disulfide bond between the heavy chains of the hinge region.

"F(ab')" refers to a Fab fragment that includes a portion of the hinge region, which can be obtained by pepsin digestion of an antibody at the residues proximal to the C-terminus of the disulfide bond between the heavy chains of the hinge region and thus is different from Fab in a small number of residues (including one or more cysteines) in the hinge region.

"F(ab')$_2$" refers to a dimer of F(ab') that comprises two light chains and part of two heavy chains.

"Fc" with regard to an antibody (e.g., of IgG, IgA, or IgD isotype) refers to that portion of the antibody consisting of the second and third constant domains of a first heavy chain bound to the second and third constant domains of a second heavy chain via disulfide bonding. Fc with regard to antibody of IgM and IgE isotype further comprises a fourth constant domain. The Fc portion of the antibody is responsible for various effector functions such as antibody-dependent cell-mediated cytotoxicity (ADCC), and complement dependent cytotoxicity (CDC), but does not function in antigen binding.

"Fv" with regard to an antibody refers to the smallest fragment of the antibody to bear the complete antigen binding site. A Fv fragment consists of the variable region of a single light chain bound to the variable region of a single heavy chain. A "dsFv" refers to a disulfide-stabilized Fv fragment that the linkage between the variable region of a single light chain and the variable region of a single heavy chain is a disulfide bond.

"Single-chain variable fragment" or "single-chain Fv antibody" or "scFv" refers to an engineered antibody consisting of a light chain variable region and a heavy chain variable region connected to one another directly or via a peptide linker sequence (Huston J S et al. *Proc Natl Acad Sci USA*, 85:5879 (1988)). A "scFv dimer" refers to a single chain comprising two heavy chain variable regions and two light chain variable regions with a linker. In certain embodiments, an "scFv dimer" is a bivalent diabody or bivalent ScFv (BsFv) comprising $V_H$-$V_L$ (linked by a peptide linker) dimerized with another $V_H$-$V_L$ moiety such that $V_H$'s of one moiety coordinate with the $V_L$'s of the other moiety and form two binding sites which can target the same antigens (or epitopes) or different antigens (or epitopes). In other embodiments, a "scFv dimer" is a bispecific diabody comprising $V_{H1}$-$V_{L2}$ (linked by a peptide linker) associated with $V_{L1}$-$V_{H2}$ (also linked by a peptide linker) such that $V_{H1}$ and $V_{L1}$ coordinate and $V_{H2}$ and $V_{L2}$ coordinate and each coordinated pair has a different antigen specificity.

"Single-chain Fv-Fc antibody" or "scFv-Fc" refers to an engineered antibody consisting of a scFv connected to the Fc region of an antibody.

"Camelized single domain antibody," "heavy chain antibody," "nanobody" or "HCAb" refers to an antibody that contains two $V_H$ domains and no light chains (Riechmann L. and Muyldermans S., *J Immunol Methods*. December 10; 231 (1-2):25-38 (1999); Muyldermans S., *J Biotechnol*. June; 74(4):277-302 (2001); WO94/04678; WO94/25591; U.S. Pat. No. 6,005,079). Heavy chain antibodies were originally obtained from Camelidae (camels, dromedaries, and llamas). Although devoid of light chains, camelized antibodies have an authentic antigen-binding repertoire (Hamers-Casterman C. et al., *Nature*. June 3; 363(6428): 446-8 (1993); Nguyen V K. et al. "Heavy-chain antibodies in Camelidae; a case of evolutionary innovation," Immunogenetics. April; 54(1):39-47 (2002); Nguyen V K. et al. *Immunology. May;* 109(1):93-101 (2003)). The variable domain of a heavy chain antibody (VHH domain) represents the smallest known antigen-binding unit generated by adaptive immune responses (Koch-Nolte F. et al., *FASEB J*. November;21(13):3490-8. Epub 2007 June 15 (2007)).

"Diabodies" include small antibody fragments with two antigen-binding sites, wherein the fragments comprise a $V_H$ domain connected to a $V_L$ domain in a single polypeptide chain ($V_H$-$V_L$ or $V_L$-$V_H$) (see, e.g., Holliger P. et al., *Proc Natl Acad Sci USA*. July 15; 90(14):6444-8 (1993); EP404097; WO93/11161). The two domains on the same chain cannot be paired, because the linker is too short, thus, the domains are forced to pair with the complementary domains of another chain, thereby creating two antigen-binding sites. The antigen-binding sites may target the same of different antigens (or epitopes).

A "domain antibody" refers to an antibody fragment containing only the variable region of a heavy chain or the variable region of a light chain. In certain embodiments, two or more $V_H$ domains are covalently joined with a peptide linker to form a bivalent or multivalent domain antibody. The two $V_H$ domains of a bivalent domain antibody may target the same or different antigens.

In certain embodiments, a "(dsFv)$_2$" comprises three peptide chains: two $V_H$ moieties linked by a peptide linker and bound by disulfide bridges to two $V_L$ moieties.

In certain embodiments, a "bispecific ds diabody" comprises $V_{H1}$-$V_{L2}$ (linked by a peptide linker) bound to $V_{L1}$-$V_{H2}$ (also linked by a peptide linker) via a disulfide bridge between $V_{H1}$ and $V_{L1}$.

In certain embodiments, a "bispecific dsFv" or "dsFv-dsFv'" comprises three peptide chains: a $V_{H1}$-$V_{H2}$ moiety wherein the heavy chains are bound by a peptide linker (e.g., a long flexible linker) and paired via disulfide bridges to $V_{L1}$ and $V_{L2}$ moieties, respectively. Each disulfide paired heavy and light chain has a different antigen specificity.

The term "humanized" as used herein means that the antibody or antigen-binding fragment comprises CDRs derived from non-human animals, FR regions derived from human, and when applicable, constant regions derived from human. In certain embodiments, the amino acid residues of the variable region framework of the humanized CD4 antibody are substituted for sequence optimization. In certain embodiments, the variable region framework sequences of the humanized CD4 antibody chain are at least 65%, 70%, 75%, 80%, 85%, 90%, 95% or 100% identical to the corresponding human variable region framework sequences.

The term "chimeric" as used herein refers to an antibody or antigen-binding fragment that has a portion of heavy and/or light chain derived from one species, and the rest of the heavy and/or light chain derived from a different species. In an illustrative example, a chimeric antibody may comprise a constant region derived from human and a variable region derived from a non-human species, such as from mouse.

The term "germline sequence" refers to the nucleic acid sequence encoding a variable region amino acid sequence or subsequence that shares the highest determined amino acid sequence identity with a reference variable region amino acid sequence or subsequence in comparison to all other known variable region amino acid sequences encoded by germline immunoglobulin variable region sequences. The germline sequence can also refer to the variable region amino acid sequence or subsequence with the highest amino acid sequence identity with a reference variable region amino acid sequence or subsequence in comparison to all other evaluated variable region amino acid sequences. The germline sequence can be framework regions only, complementarity determining regions only, framework and complementarity determining regions, a variable segment (as defined above), or other combinations of sequences or subsequences that comprise a variable region. Sequence identity can be determined using the methods described herein, for example, aligning two sequences using BLAST, ALIGN, or another alignment algorithm known in the art. The germline nucleic acid or amino acid sequence can have at least about 90%, 91, 92%, 93%, 94%, 95%, 96%, 97%, 98%, 99%, or 100% sequence identity with the reference variable region nucleic acid or amino acid sequence. Germline sequences can be determined, for example, through the publicly available international ImMunoGeneTics database (IMGT) and V-base.

The term "anti-human CD4 antibody" as used herein refers to an antibody or an antigen-binding fragment thereof that is capable of specific binding to human CD4 (hCD4) or variant thereof with a sufficient specificity and/or affinity, for example, to provide for therapeutic use. The term "variant" with respect to a reference protein or peptide (e.g., hCD4) as used herein refers to a modified version of the reference protein or peptide, e.g., functional equivalents, fragments, fusions, derivatives, mimetics, or any combination thereof, that has an amino acid sequence of at least 70% (e.g. 80%, 85%, 90%, 91%, 92%, 93%, 94%, 95%, 96%, 97%, 98%, 99%) sequence identity to the sequence of the reference protein or peptide, and retains at least 25% (e.g. 35%, 50%, 75%, 90%, 95%, or 99%) of the biological activity or binding activity of the protein or peptide (e.g. the wild-type protein or peptide). The variant can be a fragment, mutant, a fusion, a truncation, or any combination thereof, of the reference protein or peptide.

The term "affinity" as used herein refers to the strength of non-covalent interaction between an immunoglobulin molecule (i.e., antibody) or fragment thereof and an antigen.

The term "specific binding" or "specifically binds" as used herein refers to a non-random binding reaction between two molecules, such as for example between an antibody and an antigen. In certain embodiments, the antibodies or antigen-binding fragments provided herein specifically bind to human and/or non-human antigen with a binding affinity ($K_D$) of $\leq 10^{-6}$M (e.g., $\leq 5 \times 10^{-7}$M, $\leq 2 \times 10^{-7}$ M, $\leq 10^{-7}$ M, $\leq 5 \times 10^{-8}$ M, $\leq 2 \times 10^{-8}$ M, $\leq 10^{-8}$ M, $\leq 5 \times 10^{-9}$ M, $\leq 4 \times 10^{-9}$ M, $\leq 3 \times 10^{-9}$M, $\leq 2 \times 10^{-9}$M, or $\leq 10^{-9}$ M. $K_D$ used herein refers to the ratio of the dissociation rate to the association rate ($k_{off}/k_{on}$), which may be determined by using any conventional method known in the art, including but are not limited to surface plasmon resonance method, microscale thermophoresis method, HPLC-MS method and flow cytometry (such as FACS) method. In certain embodiments, the $K_D$ value can be appropriately determined by using flow cytometry method. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998), for a description of immunoassay formats and conditions that can be used to determine specific immunoreactivity). Typically, a specific or selective binding reaction will produce a signal at least twice over the background signal and more typically at least 10 to 100 times over the background.

The term "amino acid" as used herein refers to an organic compound containing amine (—NH$_2$) and carboxyl (—COOH) functional groups, along with a side chain specific to each amino acid. The names of amino acids are also represented as standard single letter or three-letter codes in the present disclosure, which are summarized as follows.

| Names | Three-letter Code | Single-letter Code |
|---|---|---|
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

A "conservative substitution" with reference to amino acid sequence refers to replacing an amino acid residue with a different amino acid residue having a side chain with similar physiochemical properties. For example, conservative substitutions can be made among amino acid residues with hydrophobic side chains (e.g., Met, Ala, Val, Leu, and Ile), among residues with neutral hydrophilic side chains (e.g., Cys, Ser, Thr, Asn and Gln), among residues with acidic side chains (e.g., Asp, Glu), among amino acids with basic side chains (e.g., His, Lys, and Arg), or among residues with aromatic side chains (e.g., Trp, Tyr, and Phe). As known in the art, conservative substitution usually does not cause significant change in the protein conformational structure, and therefore could retain the biological activity of a protein.

"Percent (%) sequence identity" with respect to amino acid sequence (or nucleic acid sequence) is defined as the percentage of amino acid (or nucleic acid) residues in a candidate sequence that are identical to the amino acid (or nucleic acid) residues in a reference sequence, after aligning the sequences and, if necessary, introducing gaps, to achieve the maximum correspondence. Alignment for purposes of determining percent amino acid (or nucleic acid) sequence identity can be achieved, for example, using publicly available tools such as BLASTN, BLASTp (available on the website of U.S. National Center for Biotechnology Information (NCBI), see also, Altschul S. F. et al, J. Mol. Biol., 215:403-410 (1990); Stephen F. et al, Nucleic Acids Res., 25:3389-3402 (1997)), ClustalW2 (available on the website of European Bioinformatics Institute, see also, Higgins D.

G. et al, Methods in Enzymology, 266:383-402 (1996); Larkin M. A. et al, Bioinformatics (Oxford, England), 23(21): 2947-8 (2007)), and ALIGN or Megalign (DNASTAR) software. Those skilled in the art may use the default parameters provided by the tool, or may customize the parameters as appropriate for the alignment, such as for example, by selecting a suitable algorithm. In certain embodiments, the non-identical residue positions may differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331, which is herein incorporated by reference.

As used herein, a "homologous sequence" refers to a polynucleotide sequence (or its complementary strand) or an amino acid sequence that has sequence identity of at least 80% (e.g., at least 85%, 88%, 90%, 91%, 92%, 93%, 94%, 95%, 96%, 97%, 98%, 99%) to another sequence when optionally aligned.

An "isolated" substance has been altered by the hand of man from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide is "isolated" if it has been sufficiently separated from the coexisting materials of its natural state so as to exist in a substantially pure state. An isolated "nucleic acid" or "polynucleotide" are used interchangeably and refer to the sequence of an isolated nucleic acid molecule. In certain embodiments, an "isolated antibody or antigen-binding fragment thereof" refers to the antibody or antigen-binding fragments having a purity of at least 60%, 70%, 75%, 80%, 81%, 82%, 83%, 84%, 85%, 86%, 87%, 88%, 89%, 90%, 91%, 92%, 93%, 94%, 95%, 96%, 97%, 98%, 99% as determined by electrophoretic methods (such as SDS-PAGE, isoelectric focusing, capillary electrophoresis), or chromatographic methods (such as ion exchange chromatography or reverse phase HPLC).

The term "subject" includes human and non-human animals. Non-human animals include all vertebrates, e.g., mammals and non-mammals, such as non-human primates, mouse, rat, cat, rabbit, sheep, dog, cow, chickens, amphibians, and reptiles. Except when noted, the terms "patient" or "subject" are used herein interchangeably.

"Treating" or "treatment" of a condition as used herein includes preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition, or some combination thereof.

The term "vector" as used herein refers to a vehicle into which a polynucleotide encoding a protein may be operably inserted so as to bring about the expression of that protein. A vector may be used to transform, transduce, or transfect a host cell so as to bring about expression of the genetic element it carries within the host cell. Examples of vectors include plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Categories of animal viruses used as vectors include retrovirus (including lentivirus), adenovirus, adeno-associated virus, herpesvirus (e.g., herpes simplex virus), poxvirus, baculovirus, papillomavirus, and papovavirus (e.g., SV40). A vector may contain a variety of elements for controlling expression, including promoter sequences, transcription initiation sequences, enhancer sequences, selectable elements, and reporter genes. In addition, the vector may contain an origin of replication. A vector may also include materials to aid in its entry into the cell, including but not limited to a viral particle, a liposome, or a protein coating. A vector can be an expression vector or a cloning vector. The present disclosure provides vectors (e.g., expression vectors) containing the nucleic acid sequence provided herein encoding the antibody or antigen-binding fragment thereof, at least one promoter (e.g., SV40, CMV, EF-1a) operably linked to the nucleic acid sequence, and at least one selection marker. Examples of vectors include, but are not limited to, retrovirus (including lentivirus), adenovirus, adeno-associated virus, herpesvirus (e.g., herpes simplex virus), poxvirus, baculovirus, papillomavirus, papovavirus (e.g., SV40), lambda phage, and M13 phage, plasmid pcDNA3.3, pMD18-T, pOptivec, pCMV, pEGFP, pIRES, pQD-Hyg-GSeu, pALTER, pBAD, pcDNA, pCal, pL, pET, pGEMEX, pGEX, pCI, pEGFT, pSV2, pFUSE, pVITRO, pVIVO, pMAL, pMONO, pSELECT, pUNO, pDUO, Psg5L, pBABE, pWPXL, pBI, p15TV-L, pPro18, pTD, pRS10, pLexA, pACT2.2, pCMV-SCRIPT®, pCDM8, pCDNA1.1/amp, pcDNA3.1, pRc/RSV, PCR 2.1, pEF-1, pFB, pSG5, pXT1, pCDEF3, pSVSPORT, pEF-Bos etc. The "host cell" as used herein refers to a cell into which an exogenous polynucleotide and/or a vector has been introduced.

The term "CD4", acronym for the term "cluster of differentiation 4" as used herein refers to is a glycoprotein found on the surface of immune cells such as T helper cells, monocytes, macrophages, and dendritic cells, and encompasses all the isoforms of CD4. A "CD4-related" disease or condition as used herein refers to any disease or condition that is associated with CD4 and/or CD4-expressing cells, e.g., CD4+ T cells, especially, Tregs. In some embodiments, the CD4 related disease or condition is, for example, autoimmune diseases, cancer, adaptive immune disease, inflammatory disease, or infectious disease.

"Cancer" as used herein refers to any medical condition characterized by malignant cell growth or neoplasm, abnormal proliferation, infiltration or metastasis, and can be benign or malignant, and includes both solid tumors and non-solid cancers (e.g., hematologic malignancies) such as leukemia. As used herein "solid tumor" refers to a solid mass of neoplastic and/or malignant cells.

The term "pharmaceutically acceptable" indicates that the designated carrier, vehicle, diluent, excipient(s), and/or salt is generally chemically and/or physically compatible with the other ingredients comprising the formulation, and physiologically compatible with the recipient thereof.

Reference to "about" a value or parameter herein includes (and describes) embodiments that are directed to that value or parameter per se. For example, description referring to "about X" includes description of "X." Numeric ranges are inclusive of the numbers defining the range. Generally speaking, the term "about" refers to the indicated value of the variable and to all values of the variable that are within the experimental error of the indicated value (e.g., within the 95% confidence interval for the mean) or within 10 percent of the indicated value, whichever is greater. Where the term "about" is used within the context of a time period (years, months, weeks, days etc.), the term "about" means that period of time plus or minus one amount of the next subordinate time period (e.g., about 1 year means 11-13 months; about 6 months means 6 months plus or minus 1 week; about 1 week means 6-8 days; etc.), or within 10 percent of the indicated value, whichever is greater.

II. Anti-Human CD4 Antibodies

In one aspect, the present disclosure provides anti-human CD4 (hCD4) antibodies and antigen-binding fragments thereof.

Binding Affinity

In certain embodiments, the anti-hCD4 antibodies provided herein are capable of binding to hCD4 at a Kd of no more than 5 nM, no more than 4.5 nM, no more than 4 nM, no more than 3.5 nM, no more than 3 nM, no more than 2.5 nM, no more than 2 nM, no more than 1.5 nM, no more than 1 nM or no more than 0.5 nM as measured by Biacore™. In certain embodiments, the anti-hCD4 antibodies provided herein are capable of binding to hCD4 at a Kd of no more than 0.5 nM, no more than 0.45 nM, no more than 0.4 nM, no more than 0.35 nM, no more than 0.3 nM, no more than 0.25 nM, no more than 0.2 nM, no more than 0.15 nM, no more than 0.1 nM or no more than 0.05 nM as measured by Biacore™. Binding affinity of the anti-hCD4 antibodies and antigen-binding fragments provided herein can be represented by $K_D$ value, which represents the ratio of dissociation rate to association rate ($k_{off}/k_{on}$) when the binding between the antigen and antigen-binding molecule reaches equilibrium. The antigen-binding affinity (e.g., $K_D$) can be appropriately determined using any suitable methods known in the art, including, for example, Kinetic Exclusion Assay (KinExA™), Biacore™, Fortebio™ or flow cytometry.

In general, the Biacore™ works by equilibrating a constant amount of one binding partner (CBP) with a varying concentration of the other binding partner (Titrant), and then capture a portion of the free CBP by fluorescence labeled secondary antibody in a short contact time which is less than the time needed for dissociation of the pre-formed CBP-Titrant complex. The fluorescence signals generated from the captured CBP are directly proportional to the concentration of free CBP in the equilibrated samples, and are used to generate a binding curve (percent free CBP vs. total Titrant concentration) when measured in a series. More details are available from Schreiber, G., Fersht, A. R. Nature Structural Biology. 1996, 3(5), 427-431. When anti-CD4 antibody is used as CBP with a constant amount, then CD4 protein can be used as the Titrant, or vice versa.

In certain embodiments, the $K_D$ of the anti-CD4 antibodies provided herein are determined in accordance to the method as described in Example 4 in the present disclosure.

Other methods suitable for measurement of $K_D$ may also be used under applicable circumstances, for example, radio-labelled antigen-binding assay (see, e.g. Chen, et al., (1999) J. Mol Biol 293:865-881), or surface plasmon resonance assays other than Biacore™.

Alternatively, binding affinity of the anti-CD4 antibodies and antigen-binding fragments provided herein to human CD4 can also be represented by "half maximal effective concentration" ($EC_{50}$) value, which refers to the concentration of an antibody where 50% of its maximal effect (e.g., binding) is observed. The $EC_{50}$ value can be measured by methods known in the art, for example, sandwich assay such as ELISA, Western Blot, flow cytometry assay, and other binding assay. In certain embodiments, the anti-CD4 antibodies and the fragments thereof provided herein specifically bind to human CD4 (e.g. a cell expressing human CD4) at an EC50 value of no more than 700 ng/ml (or no more than 680, 660, 640, 620, 600, 580, 560, 540, 520, 500, 480, 460, 440, 420, 400, 380, 360, 340, 320, 300, 280, 260, 240, 220, 200, 180, 160, 140, 120, 100, 80, 60, 40, 20, 13.5 13, 12.5, 12, 11.5, 11, 10.5, 10, 9, 8, 7, 6, 5.5, 5, 4.5, 4, 3, 2, or 1 ng/ml) as measured by FACS. In certain embodiments, the anti-CD4 antibodies and the fragments thereof provided herein specifically bind to human CD4 (e.g., a cell expressing human CD4) at an EC50 value of no more than 40 ng/ml (or no more than 38, 36, 34, 32, 30, 28, 26, 24, 22, 20, 16, 14, 12, 10, 8, 6, 4, 2, or 1 ng/ml) as measured by ELISA.

Antibody Sequences

In one aspect, the present disclosure provides an anti-CD4 antibody or an antigen-binding fragment thereof provided herein, comprising a heavy chain variable (VH) region and/or a light chain variable (VL) region, wherein the heavy chain variable region comprises:
  a) a HCDR1 comprises a sequence selected from SEQ ID NOs: 1, 11, 21, 31 and 41,
  b) a HCDR2 comprises a sequence selected from SEQ ID NOs: 2, 12, 22 and 42,
  c) a HCDR3 comprises a sequence selected from SEQ ID NOs: 3, 13, 23 and 33 and 43, and/or
wherein the light chain variable region comprises:
  d) a LCDR1 comprises a sequence selected from SEQ ID NOs: 4, 14, 24 and 34,
  e) a LCDR2 comprises a sequence selected from SEQ ID NOs: 5, 15 and 25, and
  f) a LCDR3 comprises a sequence selected from SEQ ID NOs: 6, 16, 26 and 46.

In certain embodiments, the antibody or an antigen-binding fragment thereof provided herein comprises:
  a) a heavy chain variable region comprising a HCDR1 comprising the sequence of SEQ ID NO: 1, a HCDR2 comprising the sequence of SEQ ID NO: 2, and a HCDR3 comprising the sequence of SEQ ID NO: 3; or
  b) a heavy chain variable region comprising a HCDR1 comprising the sequence of SEQ ID NO: 11, a HCDR2 comprising the sequence of SEQ ID NO: 12, and a HCDR3 comprising the sequence of SEQ ID NO: 13; or
  c) a heavy chain variable region comprising a HCDR1 comprising the sequence of SEQ ID NO: 21, a HCDR2 comprising the sequence of SEQ ID NO: 22, and a HCDR3 comprising the sequence of SEQ ID NO: 23; or
  d) a heavy chain variable region comprising a HCDR1 comprising the sequence of SEQ ID NO: 31, a HCDR2 comprising the sequence of SEQ ID NO: 2, and a HCDR3 comprising the sequence of SEQ ID NO: 33; or
  e) a heavy chain variable region comprising a HCDR1 comprising the sequence of SEQ ID NO: 41, a HCDR2 comprising the sequence of SEQ ID NO: 42, and a HCDR3 comprising the sequence of SEQ ID NO: 43.

In certain embodiments, the antibody or an antigen-binding fragment thereof provided herein comprises:
  a) a light chain variable region comprising a LCDR1 comprising the sequence of SEQ ID NO: 4, a LCDR2 comprising the sequence of SEQ ID NO: 5, and a LCDR3 comprising the sequence of SEQ ID NO: 6; or b) a light chain variable region comprising a LCDR1 comprising the sequence of SEQ ID NO: 14, a LCDR2 comprising the sequence of SEQ ID NO: 15, and a LCDR3 comprising the sequence of SEQ ID NO: 16; or c) a light chain variable region comprising a LCDR1 comprising the sequence of SEQ ID NO: 24, a LCDR2 comprising the sequence of SEQ ID NO: 25, and a LCDR3 comprising the sequence of SEQ ID NO: 26; or d) a light chain variable region comprising a LCDR1 comprising the sequence of SEQ ID NO: 34, a LCDR2 comprising the sequence of SEQ ID NO: 5, and a LCDR3 comprising the sequence of SEQ ID NO: 6; or e) a light chain variable region comprising a LCDR1 comprising the sequence of SEQ ID NO: 24, a LCDR2 comprising the sequence of SEQ ID NO: 25, and a LCDR3 comprising the sequence of SEQ ID NO: 46.

In certain embodiments, the antibody or an antigen-binding fragment thereof provided herein comprises:

a) a heavy chain variable region comprising a HCDR1 comprising the sequence of SEQ ID NO: 1, a HCDR2 comprising the sequence of SEQ ID NO: 2, and a HCDR3 comprising the sequence of SEQ ID NO: 3; and a light chain variable region comprising a LCDR1 comprising the sequence of SEQ ID NO: 4, a LCDR2 comprising the sequence of SEQ ID NO: 5, and a LCDR3 comprising the sequence of SEQ ID NO: 6;

b) a heavy chain variable region comprising a HCDR1 comprising the sequence of SEQ ID NO: 11, a HCDR2 comprising the sequence of SEQ ID NO: 12, and a HCDR3 comprising the sequence of SEQ ID NO: 13; and a light chain variable region comprising a LCDR1 comprising the sequence of SEQ ID NO: 14, a LCDR2 comprising the sequence of SEQ ID NO: 15, and a LCDR3 comprising the sequence of SEQ ID NO: 16;

c) a heavy chain variable region comprising a HCDR1 comprising the sequence of SEQ ID NO: 21, a HCDR2 comprising the sequence of SEQ ID NO: 22, and a HCDR3 comprising the sequence of SEQ ID NO: 23; and a light chain variable region comprising a LCDR1 comprising the sequence of SEQ ID NO: 24, a LCDR2 comprising the sequence of SEQ ID NO: 25, and a LCDR3 comprising the sequence of SEQ ID NO: 26;

d) a heavy chain variable region comprising a HCDR1 comprising the sequence of SEQ ID NO: 31, a HCDR2 comprising the sequence of SEQ ID NO: 2, and a HCDR3 comprising the sequence of SEQ ID NO: 33; and a light chain variable region comprising a LCDR1 comprising the sequence of SEQ ID NO: 34, a LCDR2 comprising the sequence of SEQ ID NO: 5, and a LCDR3 comprising the sequence of SEQ ID NO: 6; or e) a heavy chain variable region comprising a HCDR1 comprising the sequence of SEQ ID NO: 41, a HCDR2 comprising the sequence of SEQ ID NO: 42, and a HCDR3 comprising the sequence of SEQ ID NO: 43; and a light chain variable region comprising a LCDR1 comprising the sequence of SEQ ID NO: 24, a LCDR2 comprising the sequence of SEQ ID NO: 25, and a LCDR3 comprising the sequence of SEQ ID NO: 46.

In certain embodiments, the antibodies provided herein comprise one or more (e.g., 1, 2, 3, 4, 5, or 6) CDR sequences of anti-hCD4 antibodies 2B6, 29B7, 33E12, 11E12, 10C2, MT412.

"2B6" as used herein refers to an antibody having a heavy chain variable region of SEQ ID NO: 7, and a light chain variable region of SEQ ID NO: 8.

"29B7" as used herein refers to an antibody having a heavy chain variable region of SEQ ID NO: 17, and a light chain variable region of SEQ ID NO: 18.

"33E12" as used herein refers to an antibody having a heavy chain variable region of SEQ ID NO: 27, and a light chain variable region of SEQ ID NO: 28.

"11E12" as used herein refers to an antibody having a heavy chain variable region of SEQ ID NO: 37, and a light chain variable region of SEQ ID NO: 38.

"10C2" as used herein refers to an antibody having a heavy chain variable region of SEQ ID NO: 47, and a light chain variable region of SEQ ID NO: 48.

"MT412" as used herein refers to an antibody having a heavy chain variable region of SEQ ID NO: 57, and a light chain variable region of SEQ ID NO: 58.

"2B6 humanized" as used herein refers to an antibody having a heavy chain variable region of SEQ ID NO: 61, and a light chain variable region of SEQ ID NO: 62.

"29B7 humanized" as used herein refers to an antibody having a heavy chain variable region of SEQ ID NO: 63, and a light chain variable region of SEQ ID NO: 64.

"MT412 humanized" as used herein refers to an antibody having a heavy chain variable region of SEQ ID NO: 65, and a light chain variable region of SEQ ID NO: 66.

Table 1 shows the CDR sequences of these anti-hCD4 antibodies. The heavy chain and light chain variable region sequences are also provided below in Tables 2 and 3.

Table 1. Sequences of Anti-hCD4 Antibodies' CDR Region

TABLE 1

Sequences of Anti-hCD4 antibodies' CDR region

| Antibody | Region | CDR1 | CDR2 | CDR3 |
|---|---|---|---|---|
| 2B6 | HCDR | SEQ ID NO: 1<br>SGYWN | SEQ ID NO: 2<br>YISFADTTNYNPSLKS | SEQ ID NO: 3<br>DDYGYYAMDY |
|  | LCDR | SEQ ID NO: 4<br>RASQDIDNYLN | SEQ ID NO: 5<br>YTSRLHS | SEQ ID NO: 6<br>QQGNTLPT |
| 29B7 | HCDR | SEQ ID NO: 11<br>THWMH | SEQ ID NO: 12<br>YINPYTGSGEYSQKFKG | SEQ ID NO: 13<br>DSTGAMDY |
|  | LCDR | SEQ ID NO: 14<br>KASQDINRYLS | SEQ ID NO: 15<br>RADRSVD | SEQ ID NO: 16<br>YDEFPYT |
| 33E12 | HCDR | SEQ ID NO: 21<br>SDYAWN | SEQ ID NO: 22<br>YISYSGITSYNPSLKS | SEQ ID NO: 23<br>LDSSGYGAMDY |
|  | LCDR | SEQ ID NO: 24<br>RASQSVSTSSYSYMH | SEQ ID NO: 25<br>YASNLES | SEQ ID NO: 26<br>QHSWDFPLT |

TABLE 1-continued

Sequences of Anti-hCD4 antibodies' CDR region

| Antibody | Region | CDR1 | CDR2 | CDR3 |
|---|---|---|---|---|
| 11E12 | HCDR | SEQ ID NO: 31<br>SSYWN | SEQ ID NO: 2<br>YISFADTTNYNPSLKS | SEQ ID NO: 33<br>DDFGYYAMDY |
|  | LCDR | SEQ ID NO: 34<br>RASQDINNYLN | SEQ ID NO: 5<br>YTSRLHS | SEQ ID NO: 6<br>QQGNTLPT |
| 10C2 | HCDR | SEQ ID NO: 41<br>SYWIE | SEQ ID NO: 42<br>EILPGSGSTNYNEEFTG | SEQ ID NO: 43<br>SVSASNWYFDV |
|  | LCDR | SEQ ID NO: 24<br>RASQSVSTSSYSYMH | SEQ ID NO: 25<br>YASNLES | SEQ ID NO: 46<br>QHSWEIPPT |
| MT412 | HCDR | SEQ ID NO: 51<br>DYSMH | SEQ ID NO: 52<br>WINTETGEPTYADDFKG | SEQ ID NO: 53<br>EDYYGHDGFLY |
|  | LCDR | SEQ ID NO: 54<br>KASQDVVTTVA | SEQ ID NO: 55<br>WASLRHT | SEQ ID NO: 56<br>QQYSSYPYT |

Table 2. Sequences Anti-hCD4 Antibodies' VH/VL

TABLE 2

Sequences anti-hCD4 antibodies' VH/VL

| Antibody | VH | VL |
|---|---|---|
| 2B6 | SEQ ID NO: 7<br>EVQLQESGPSLVKPSQTLSLT<br>CSVTGDSITSGYWNWIRKFPG<br>HKLEFLGYISFADTTNYNPSL<br>KSRVSITRDTSKNQFDLQLKS<br>VTTEDTATYHCARDDYGYYAM<br>DYWGQGISVTVSS | SEQ ID NO: 8<br>DIHLTQTTSSLSASLGDRVTI<br>ICRASQDIDNYLNWYQLKPDG<br>TLKLLIYYTSRLHSGVPSRFS<br>GSGSGTEYSLTISNLEREDVA<br>TYFCQQGNTLPTFGAGTKLEL<br>K |
| 29B7 | SEQ ID NO: 17<br>QVQLQQSGAELAKPGASVKMS<br>CKTSADSLNTHVVMHWVKQRP<br>GQGLEWIGYINPYTGSGEYSQ<br>KFKGKATLTADISSSTAYMQL<br>ISLTSEDSAVYYCAYDSTGAM<br>DYWGQGTSVTVSS | SEQ ID NO: 18<br>DIKMTQSPSSMYASLGERITI<br>TCKASQDINRYLSWFQQKPGK<br>SPKTPIYRADRSVDGVPSRFS<br>GSGSGQDYSLTISSLEYEDMG<br>IYYCQQYDEFPYTFGGGTKLE<br>IK |
| 33E12 | SEQ ID NO: 27<br>DVQLQESGPGLVKPSQSLSLT<br>CTVTGYSITSDYAWNWIRQFP<br>GNKLEWMGYISYSGITSYNPS<br>LKSRFSITRDTSKNQFFLQLN<br>SVTTEDTATYYCARLDSSGYG<br>AMDYWGQGTSVTVSS | SEQ ID NO: 28<br>DIVLTQSPASLPVSLGQRATI<br>SCRASQSVSTSSYSYMHVVYQ<br>QKPGQPPKLLIRYASNLESGV<br>PARFSGSGSGTDFTLNIHPVE<br>EEDTATYYCQHSWDFPLTFGA<br>GTKLELK |
| 11E12 | SEQ ID NO: 37<br>EVQLEESGPSLVKPSQTLSLTC<br>SVTGDSITSSYWNWIRKFPGHK<br>LEFLGYISFADTTNYNPSLKS<br>RISITRDTSKNQFDLQLKSVT<br>TEDTATYYCARDDFGYYAMDW<br>GQGISVTVSS | SEQ ID NO: 38<br>DIYVTQTTSSLSASLGDRVTI<br>ICRASQDINNYLNWYQLKPDG<br>TLKLLIYYTSRLHSGVPSRFG<br>GSGSGTEYSLTISNLEQEDVA<br>TYFCQQGNTLPTFGAGTKLEL<br>K |
| 10C2 | SEQ ID NO: 47<br>EVKLQQSGTELMKPGASVKIS<br>CKATGYTFSSYWIEWIKQRPGR<br>GLEWIGEILPGSGSTNYNEEFT<br>GRATFTADTFSNTAYMQLSSLT<br>SEDSAVYYCARSVSASNWYFD<br>VWGAGTTVTVSS | SEQ ID NO: 48<br>DIVMTQSPASLAVSLGQRATI<br>SCRASQSVSTSSYSYMHWYQQ<br>KPGQPPKFLIKYASNLESGVP<br>ARFSGSGSGTDFTLNIHPVEE<br>EDTATYYCQHSWEIPPTFGGG<br>TKLEIK |
| MT412 | SEQ ID NO: 57<br>QIQLVQSGPELKKPGETVKISC<br>KASGYTFTDYSMHWVKQAPG<br>KDLKWMGWINTETGEPTYAD<br>DFKGRFAFSLETSASTAYLQIN<br>NLKNEDTATYFCAREDYYGHD<br>GFLYWGQGTLVTVSS | SEQ ID NO: 58<br>DIVMTQSHKFMSTSVGDRVSI<br>TCKASQDVVTTVAWYQQKPG<br>QSPKLLIYWASLRHTGVPDRF<br>TGSGSGTDFTLTISNVQFEDL<br>ADYFCQQYSSYPYTFGGGTKL<br>EIK |

The antibody or antigen-binding fragment thereof provided herein can be a monoclonal antibody, polyclonal antibody, humanized antibody, chimeric antibody, recombinant antibody, bispecific antibody, labeled antibody, bivalent antibody, or anti-idiotypic antibody. A recombinant antibody is an antibody prepared in vitro using recombinant methods rather than in animals.

CDRs are known to be responsible for antigen binding, however, it has been found that not all of the 6 CDRs are necessarily indispensable or unchangeable. In other words, it is possible to replace or change or modify 1, 2, or 3 CDRs in anti-hCD4 antibodies 2B6, 29B7, 33E12, 11E12, 10C2 or MT412, yet substantially retain the specific binding affinity to hCD4.

In certain embodiments, the anti-hCD4 antibodies and the antigen-binding fragments provided herein comprise a heavy chain CDR3 sequence of one of the anti-hCD4 antibodies 2B6, 29B7, 33E12, 11E12, 10C2 or MT412. In certain embodiments, the anti-hCD4 antibodies and the antigen-binding fragments provided herein comprise a heavy chain CDR3 sequence of SEQ ID NOs: 3, 13, 23, 33, 43 and 53. Heavy chain CDR3 regions are located at the center of the antigen-binding site, and therefore are believed to make the most contact with antigen and provide the most free energy to the affinity of antibody to antigen. It is also believed that the heavy chain CDR3 is by far the most diverse CDR of the antigen-binding site in terms of length, amino acid composition and conformation by multiple diversification mechanisms (Tonegawa S. Nature. 302:575-81). The diversity in the heavy chain CDR3 is sufficient to produce most antibody specificities (Xu J L, Davis M M. Immunity. 13:37-45) as well as desirable antigen-binding affinity (Schier R, etc. J Mol Biol. 263:551-67).

In some embodiments, the anti-hCD4 antibodies and the antigen-binding fragments provided herein comprise all or a portion of the heavy chain variable domain and/or all or a portion of the light chain variable domain. In one embodiment, the anti-hCD4 antibodies and the antigen-binding fragments provided herein is a single domain antibody which consists of all or a portion of the heavy chain variable domain provided herein. More information of such a single domain antibody is available in the art (see, e.g., U.S. Pat. No. 6,248,516).

In certain embodiments, the antibodies and antigen-binding fragments thereof provided herein comprise suitable framework region (FR) sequences, as long as the antibodies and antigen-binding fragments thereof can specifically bind to CD4. The CDR sequences provided in Table 1 are obtained from mouse antibodies, but they can be grafted to any suitable FR sequences of any suitable species such as mouse, human, rat, rabbit, among others, using suitable methods known in the art such as recombinant techniques.

In certain embodiments, the antibodies and antigen-binding fragments thereof provided herein are humanized. A humanized antibody or antigen-binding fragment is desirable in its reduced immunogenicity in human. A humanized antibody is chimeric in its variable regions, as non-human CDR sequences are grafted to human or substantially human FR sequences. Humanization of an antibody or antigen-binding fragment can be essentially performed by substituting the non-human (such as murine) CDR genes for the corresponding human CDR genes in a human immunoglobulin gene (see, for example, Jones et al., Nature (1986) 321:522-525; Riechmann et al., Nature (1988) 332:323-327; Verhoeyen et al., Science (1988) 239:1534-1536). Simulation of the three-dimensional structure of variable regions or domains of the parent non-human antibody can be performed before or after this.

Suitable human heavy chain and light chain variable domains can be selected to achieve CDR grafting using methods known in the art. In an illustrative example, "best-fit" approach can be used, where a non-human (e.g., rodent) antibody variable domain sequence is screened or BLASTed against a database (e.g., Protein Data Bank) of known human variable domain germline sequences, and the human sequence closest to the non-human query sequence is identified and used as the human scaffold for grafting the non-human CDR sequences (see, for example, Sims et al., J. Immunol. (1993) 151:2296; Chothia et al., J. Mot. Biol. (1987) 196:901). Alternatively, a framework derived from the consensus sequence of all human antibodies may be used for the grafting of the non-human CDRs (see, for example, Carter et al., Proc. Natl. Acad. Sci. USA (1992) 89:4285; Presta et al., J. Immunol. (1993) 151:2623).

In certain embodiments, the humanized antibodies or antigen-binding fragments provided herein are composed of substantially all human sequences except for the CDR sequences which are non-human. In some embodiments, the variable region FRs, and constant regions if present, are entirely or substantially from human immunoglobulin sequences. The human FR sequences and human constant region sequences may be derived from different human immunoglobulin genes, for example, FR sequences derived from one human antibody and constant region from another human antibody.

In some embodiments, the FR regions derived from human may comprise the same amino acid sequence as the human immunoglobulin from which it is derived. In some embodiments, one or more amino acid residues of the human FR are substituted with the corresponding residues from the parent non-human antibody. This may be desirable in certain embodiments to make the humanized antibody or its fragment closely approximate the non-human parent antibody structure to reduce or avoid immunogenicity and/or improve or retain the binding activity or binding affinity.

In certain embodiments, the humanized antibody or antigen-binding fragment provided herein comprises no more than 10, 9, 8, 7, 6, 5, 4, 3, 2, or 1 amino acid residue substitutions in each of the human FR sequences, or no more than 10, 9, 8, 7, 6, 5, 4, 3, 2, or 1 amino acid residue substitutions in all the FRs of a heavy or a light chain variable domain. In some embodiments, such change in amino acid residue could be present in heavy chain FR regions only, in light chain FR regions only, or in both chains. In certain embodiments, the one or more amino acid residues are mutated, for example, back-mutated to the corresponding residue found in the non-human parent antibody (e.g., in the mouse framework region) from which the CDR sequences are derived. Suitable positions for mutations can be selected by a skilled person following principles known in the art. For example, a position for mutation can be selected where: 1) the residue in the framework of the human germline sequence is rare (e.g. in less than 20% or less than 10% in human variable region sequence); 2) the position is immediately adjacent to one or more of the 3 CDR's in the primary sequence of the human germline chain, as it is likely to interact with residues in the CDRs; or 3) the position is close to CDRs in a 3-dimensional model, and therefore can have a good probability of interacting with amino acids in the CDR. The residue at the selected position can be mutated back to the corresponding residue in the parent antibody, or to a residue which is neither the corresponding residue in human germline sequence nor in parent antibody, but to a residue typical of human sequences, i.e., that occurs more frequently at that position in the known human sequences belonging to the same subgroup as the human germline sequence (see U.S. Pat. No. 5,693,762).

In certain embodiments, the humanized light and heavy chains of the present disclosure are substantially non-immunogenic in humans and retain substantially the same affinity as or even higher affinity than the parent antibody to hCD4.

In certain embodiments, the humanized antibody or antigen-binding fragment provided herein comprises a heavy chain variable region comprising a sequence selected from the group consisting of SEQ ID NO: 61, SEQ ID NO: 63, SEQ ID NO: 65, and a homologous sequence thereof having at least 80% (e.g., at least 85%, 90%, 95%, 96%, 97%, 98%, or 99%) sequence identity yet retaining specific binding specificity or affinity to hCD4.

In certain embodiments, the humanized antibody or an antigen-binding fragment thereof provided herein further comprises a light chain variable region comprising a sequence selected from the group consisting of SEQ ID NO: 62, SEQ ID NO: 64, SEQ ID NO: 66, and a homologous sequence thereof having at least 80% (e.g. at least 85%, 90%, 95%, 96%, 97%, 98%, or 99%) sequence identity yet retaining specific binding specificity or affinity to hCD4.

In certain embodiments, the humanized antibody or antigen-binding fragment provided herein comprises a heavy chain variable region comprising a sequence selected from the group consisting of SEQ ID NO: 61, SEQ ID NO: 63, and SEQ ID NO: 65, and a homologous sequence thereof having at least 80% (e.g. at least 85%, 90%, 95%, 96%, 97%, 98%, or 99%) sequence identity yet retaining specific binding specificity or affinity to hCD4, and a light chain variable region comprising a sequence selected from the group consisting of SEQ ID NO: 62, SEQ ID NO: 64, and SEQ ID NO: 66 and a homologous sequence thereof having at least 80% (e.g. at least 85%, 90%, 95%, 96%, 97%, 98%, or 99%) sequence identity yet retaining specific binding specificity or affinity to hCD4.

In certain embodiments, the humanized antibody or antigen-binding fragment provided herein comprises a heavy chain variable region comprising a sequence selected from the group consisting of SEQ ID NO: 61, SEQ ID NO: 63, and SEQ ID NO: 65 and a homologous sequence thereof having at least 80% (e.g. at least 85%, 90%, 95%, 96%, 97%, 98%, or 99%) sequence identity, and a light chain variable region comprising a sequence selected from the group consisting of SEQ ID NO: 62, SEQ ID NO: 64 and SEQ ID NO: 66 and a homologous sequence thereof having at least 80% (e.g. at least 85%, 90%, 95%, 96%, 97%, 98%, or 99%) sequence identity, yet retaining specific binding specificity or affinity to hCD4.

In certain embodiments, the humanized antibody or an antigen-binding fragment thereof provided herein further comprises a pair of heavy chain variable region and light chain variable region sequences selected from the group consisting of: SEQ ID NOs: 61/62, 63/64, 65/66, or a pair of sequences having at least 80% (e.g., at least 85%, 90%, 95%, 96%, 97%, 98%, or 99%) sequence identity thereof yet retaining specific binding specificity or affinity to hCD4.

Table 3. Sequences of Humanized Antibody VH/VL

| Antibody | VH | VL |
|---|---|---|
| 2B6 humanized | SEQ ID NO: 61<br>QVQLQESGPGLVKPSETLSLTCTVSG<br>DSITSGYWNWIRQPPGKGLEFLGYI<br>SFADTTNYNPSLKSRVTISRDTSKNQ<br>FSLKLSSVTAADTAVYYCARDDYG<br>YYAMDYWGQGTLVTVSS | SEQ ID NO: 62<br>DIQLTQSPSSLSASVGDRVTITCR<br>ASQDIDNYLNWYQQKPGKAPKL<br>LIYYTSRLHSGVPSRFSGSGSGTD<br>YTLTISSLQPEDFATYYCQQGNTL<br>PTFGQGTKLEIK |
| 29B7 humanized | SEQ ID NO: 63<br>QVQLVQSGAEVKKPGASVKVSCKA<br>SGDSLNTHWMHWVRQAPGQRLEVvr<br>IGYINPYTGSGEYSQKFKGRATLTAD<br>ISASTAYMELSSLRSEDTAVYYCAYD<br>STGAMDYWGQGTLVTVSS | SEQ ID NO: 64<br>DIQMTQSPSSLSASVGDRVTITCK<br>ASQDINRYLSWFQQKPGKAPKTP<br>IYRADRSVDGVPSRFSGSGSGQD<br>YTLTISSLQPEDFATYYCQQYDEF<br>PYTFGQGTKLEIK |
| MT412 humanized | SEQ ID NO: 65<br>QIQLVQSGSELKKPGASVKVSCKAS<br>GYTFTDYSMHWVRQAPGQGLEWM<br>GWINTETGEPTYADDFKGRFVFSLD<br>TSVSTAYLQISSLKAEDTAVYYCARE<br>DYYGHDGFLYWGQGTLVTVSS | SEQ ID NO: 66<br>DIQMTQSPSFLSASVGDRVTITCK<br>ASQDVVTTVAWYQQKPGKAPKL<br>LIYWASLRHTGVPSRFSGSGSGTE<br>FTLTISSLQPEDFATYFCQQYSSYP<br>YTFGQGTKLEIKR |

The humanized anti-hCD4 antibodies provided herein retained the specific binding affinity to hCD4, and are at least comparable to, or even better than, the parent antibodies in that aspect. In certain embodiments, the humanized anti-hCD4 antibodies provided herein exhibited significantly higher specific binding affinity to hCD4, as compared to the parent antibodies in that aspect.

Antibody Variants

The anti-hCD4 antibodies and antigen-binding fragments thereof provided herein also encompass various types of variants of the antibody sequences provided herein.

In certain embodiments, the variants comprise one or more modification(s) or substitution(s) in 1, 2, or 3 CDR sequences as provided in Table 1, in one or more FR sequences, in the heavy or light chain variable region sequences provided herein, and/or in the constant region (e.g., Fc region). Such antibody variants retain specific binding affinity to hCD4 of their parent antibodies, but have one or more desirable properties conferred by the modification(s) or substitution(s). For example, the antibody variants may have improved antigen-binding affinity, improved glycosylation pattern, reduced risk of glycosylation, reduced deamination, increased effector function(s), improved FcRn receptor binding, increased pharmacokinetic half-life, pH sensitivity, and/or compatibility to conjugation (e.g., one or more introduced cysteine residues), to name a few.

A parent antibody sequence may be screened to identify suitable or preferred residues to be modified or substituted, using methods known in the art, for example "alanine scanning mutagenesis" (see, for example, Cunningham and Wells (1989) Science, 244:1081-1085). Briefly, target residues (e.g., charged residues such as Arg, Asp, His, Lys, and Glu) can be identified and replaced by a neutral or negatively charged amino acid (e.g., alanine or polyalanine), and the modified antibodies are produced and screened for the interested property. If substitution at a particular amino acid location demonstrates an interested functional change, then the position can be identified as a potential residue for modification or substitution. The potential residues may be further assessed by substituting with a different type of residue (e.g., cysteine residue, positively charged residue, etc.).

Constant Region and Variants Thereof

In certain embodiments, the anti-hCD4 antibodies and the fragments thereof provided herein further comprise an immunoglobulin constant region. In certain embodiments, the anti-hCD4 antibodies and the fragments thereof provided herein further comprise a constant region of human Ig, such as human IgG. In some embodiments, an immunoglobulin constant region comprises a heavy chain and/or a light chain constant region. The heavy chain constant region comprises CH1, hinge, and/or CH2-CH3 regions. In certain embodiments, the heavy chain constant region comprises an Fc region. In certain embodiments, the light chain constant region comprises Cκ or Cλ.

In certain embodiments, the humanized antibodies provided herein may comprise the heavy chain variable region fused to the constant region of human IgG1 isotype and the light chain variable region fused to the constant region of human kappa chain. In certain embodiments, the kappa chain comprises an amino acid sequence of SEQ ID NO: 68.

Fc regions of different Ig isotypes have different abilities to induce effector functions. For example, Fc regions of IgG1 and IgG3 have been recognized to induce both ADCC and CDC more effectively than those of IgG2 and IgG4. In certain embodiments, the antibodies and antigen-binding fragments thereof provided herein comprises an Fc region of IgG1, or IgG3 isotype, which could induce ADCC or CDC; or alternatively, a constant region of IgG4 or IgG2 isotype, which has reduced or depleted effector function. In some embodiments, the Fc region is derived from human IgG1 with increased effector functions, e.g., ADCC. In certain embodiments, the antibodies and antigen-binding fragments thereof provided herein comprise a wild type human IgG1 Fc region or other wild type human IgG1 alleles. In some embodiments, the Fc region derived from human IgG1 comprises an amino acid sequence having at least 80%, at least 85%, at least 90%, or at least 95% sequence identity of SEQ ID NO: 69. In some embodiments, the Fc region derived from human IgG1 comprises an amino acid sequence of SEQ ID NO: 67. In certain embodiments, the antibodies and antigen-binding fragments thereof provided herein comprise a human IgG1 Fc region comprising one or more mutations, which can confer increased CDC or ADCC relative to wild-type constant region.

In certain embodiments, the antibodies and antigen-binding fragments thereof provided herein comprise a human IgG1 Fc region comprising a S298A mutation, an E333A mutation, and/or a K334A mutation, which confers increased ADCC relative to wild-type constant region. Other such mutations that increases ADCC include without limitation S239D, I332E, H268F, S324T, S236A, G236A, P247I, A339(D/Q), D280H, K290S, 5298 (D/V), F243L, R292P, Y300L, P396L, V305I, K290(E/N), S298G, T299A, K326E, E382V, M428I, S298A, K326A, E333A, K334A, and any combination thereof, wherein the numbering of the residues in the Fc region is according to EU numbering (Edelman, G. M. et al., Proc. Natl. Acad. USA, 63, 78-85 (1969)4 In certain embodiments, the antibodies and antigen-binding fragments thereof provided herein comprise a human IgG1 Fc region comprising a S298A mutation, an E333A mutation, and a K334A mutation, i.e., "3A mutation" as used herein, which confers increased ADCC relative to wild-type constant region.

Affinity Variant

An affinity variant retains specific binding affinity to hCD4 of the parent antibody, or even have improved hCD4 specific binding affinity over the parent antibody. Various methods known in the art can be used to achieve this purpose. For example, a library of antibody variants (such as Fab or scFv variants) can be generated and expressed with phage display technology, and then screened for the binding affinity to human CD4. For another example, computer software can be used to virtually simulate the binding of the antibodies to human CD4, and identify the amino acid residues on the antibodies which form the binding interface. Such residues may be either avoided in the substitution so as to prevent reduction in binding affinity, or targeted for substitution to provide for a stronger binding.

In certain embodiments, at least one (or all) of the substitution(s) in the CDR sequences, FR sequences, or variable region sequences comprises a conservative substitution.

In certain embodiments, the anti-hCD4 antibodies or antigen-binding fragments provided herein comprise one or more amino acid residue substitutions in one or more CDR sequences, and/or one or more FR sequences. In certain embodiments, an affinity variant comprises no more than 10, 9, 8, 7, 6, 5, 4, 3, 2, or 1 substitutions in one or more of the CDR sequences and/or FR sequences in total.

In certain embodiments, the anti-hCD4 antibodies and antigen-binding fragments thereof comprise 1, 2, or 3 CDR sequences having at least 80% (e.g., at least 85%, 88%, 90%, 91%, 92%, 93%, 94%, 95%, 96%, 97%, 98%, 99%) sequence identity to that (or those) listed in Table 1, and in the meantime retain the binding affinity to hCD4 at a level similar to or even higher than its parental antibody.

Glycosylation Variant

The anti-hCD4 antibodies and antigen-binding fragments provided herein also encompass a glycosylation variant, which can be obtained to either increase or decrease the extent of glycosylation of the antibody or antigen binding fragment. The term "glycosylation" as used herein, refers to enzymatic process that attaches glycans such as fucose, xylose, mannose, or GlcNAc phosphoserine glycan to proteins, lipids, or other organic molecules. Depending on the carbon linked to the glycan, glycosylation can be divided into five classes including: N-linked glycosylation, O-linked glycosylation, phospho-glycosylation, C-linked glycosylation, and glypiation.

Glycosylation of antibodies is typically N-linked or O-linked. N-linked refers to the attachment of the carbohydrate moiety to the side chain of an asparagine residue, for example, an asparagine residue in a tripeptide sequence such as asparagine-X-serine and asparagine-X-threonine, where X is any amino acid except proline. O-linked glycosylation refers to the attachment of one of the sugars N-aceylgalactosamine, galactose, or xylose to a hydroxyamino acid, most commonly to serine or threonine.

The classic ADCC response is mediated by natural killer (NK) cells following the binding of the FcγRIIIa to the Fc region of antibody molecules. This binding triggers the NK cells to release cytokines and cytolytic agents that eventually kill the target cell. Without wishing to be bound by any theory, it is believed that the FcγRIII binds the Fc region of IgG1 antibodies by interacting with the hinge region and the CH2 domain, and such interaction can be significantly affected by the glycan present at the conserved N-glycosylation site Asn297 (N297) in each of the CH2 domains (Krapp S et al., J Mol Biol. 2003; 325:979-89.). Isothermal titration calorimetry showed that the IgG1-FcgRIIIa binding is driven by favorable binding enthalpy ($\Delta H$), but opposed by unfavorable binding entropy change ($\Delta S$). Fucose removal enhanced the favorable $\Delta H$ leading to an increase in the binding constant of IgG1 for the receptor by a factor of 20-30 fold (Okazaki A et al., J Mol Biol. 2004; 336:1239-49.). Accordingly, glycoengineering the Fc N-glycan to reduce core fucose can increase the affinity between antibody and the FcγRIII so as to enhance ADCC activity. For example, the afucosylated IgG1 could significantly improve ADCC activity in vitro using peripheral blood mononuclear cells (PBMCs) or NK cells in comparison to its fucosylated counterpart (Iida S et al., Clin Cancer Res. 2006; 12:2879-87; Shields R L et al., J Biol Chem. 2002; 277:26733-40; Shinkawa T et al., J Biol Chem. 2003; 278:3466-73).

In certain embodiments, anti-hCD4 antibodies and antigen-binding fragments provided herein comprises a glycoengineered Fc region, wherein the Fc region comprises reduced core fucose. In certain embodiments, anti-hCD4 antibodies and antigen-binding fragments provided herein comprises an Fc region derived from the afucosylated IgG1.

Cysteine-Engineered Variant

The anti-hCD4 antibodies and antigen-binding fragments provided herein also encompass a cysteine-engineered variant, which comprises one or more introduced free cysteine amino acid residues.

A free cysteine residue is one which is not part of a disulfide bridge. A cysteine-engineered variant is useful for conjugation with, for example a cytotoxic and/or imaging compound, a label, or a radio-isotope among others, at the site of the engineered cysteine, through for example a maleimide or haloacetyl. Methods for engineering antibodies or antigen-binding fragments to introduce free cysteine residues are known in the art, see, for example, WO2006/034488.

Antigen-Binding Fragments

Provided herein are also anti-hCD4 antigen-binding fragments. Various types of antigen-binding fragments are known in the art and can be developed based on the anti-hCD4 antibodies provided herein, including for example, the exemplary antibodies whose CDR sequences are shown in Tables 1, and their different variants (such as affinity variants, glycosylation variants, Fc variants, cysteine-engineered variants and so on).

In certain embodiments, an anti-hCD4 antigen-binding fragment provided herein is a diabody, a Fab, a Fab', a F(ab')$_2$, a Fd, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), an scFv dimer (bivalent diabody), a multispecific antibody, a camelized single domain antibody, a nanobody, a domain antibody, or a bivalent domain antibody.

Various techniques can be used for the production of such antigen-binding fragments. Illustrative methods include, enzymatic digestion of intact antibodies (see, e.g., Morimoto et al., Journal of Biochemical and Biophysical Methods 24:107-117 (1992); and Brennan et al., Science, 229:81 (1985)), recombinant expression by host cells such as E. coli (e.g., for Fab, Fv and ScFv antibody fragments), screening from a phage display library as discussed above (e.g., for ScFv), and chemical coupling of two Fab'-SH fragments to form F(ab')$_2$ fragments (Carter et al., Bio/Technology 10:163-167 (1992)). Other techniques for the production of antibody fragments will be apparent to a skilled practitioner.

In certain embodiments, the antigen-binding fragment is a scFv. Generation of scFv is described in, for example, WO 93/16185; U.S. Pat. Nos. 5,571,894; and 5,587,458. scFv may be fused to an effector protein at either the amino or the carboxyl terminus to provide for a fusion protein (see, for example, Antibody Engineering, ed. Borrebaeck).

In certain embodiments, the anti-hCD4 antibodies and antigen-binding fragments thereof provided herein are bivalent, tetravalent, hexavalent, or multivalent. The term "valent" as used herein refers to the presence of a specified number of antigen binding sites in a given molecule. As such, the terms "bivalent", "tetravalent", and "hexavalent" denote the presence of two binding site, four binding sites, and six binding sites, respectively, in an antigen-binding molecule. Any molecule being more than bivalent is considered multivalent, encompassing for example, trivalent, tetravalent, hexavalent, and so on.

A bivalent molecule can be monospecific if the two binding sites are both specific for binding to the same antigen or the same epitope. This, in certain embodiments, provides for stronger binding to the antigen or the epitope than a monovalent counterpart. Similar, a multivalent molecule may also be monospecific. In certain embodiments, in a bivalent or multivalent antigen-binding moiety, the first valent of binding site and the second valent of binding site are structurally identical (i.e. having the same sequences), or structurally different (i.e. having different sequences albeit with the same specificity).

A bivalent can also be bispecific, if the two binding sites are specific for different antigens or epitopes. This also applies to a multivalent molecule. For example, a trivalent molecule can be bispecific when two binding sites are monospecific for a first antigen (or epitope) and the third binding site is specific for a second antigen (or epitope).

Epitope-Competing Antibodies

In another aspect, the present disclosure provides antibodies that binds to the same epitope to which the antibody or antigen-binding fragment thereof provided herein binds. In another aspect, the present disclosure provides antibodies that competes for binding to hCD4 with the antibody or antigen-binding fragment thereof provided herein.

The term "epitope" as used herein refers to the specific group of atoms or amino acids on an antigen to which an antibody binds. An epitope can include specific amino acids, sugar side chains, phosphoryl or sulfonyl groups that directly contact an antibody. Those skilled in the art will recognize that it is possible to determine, without undue experimentation, if an antibody binds to the same or overlapping or adjacent epitope as the antibody of present disclosure (e.g., hybridoma/chimeric or humanized antibodies 2B6, 29B7, 33E12, 11E12, 10C2, MT412 and any of the chimeric and humanized variant thereof provided herein) by ascertaining whether the two competes for binding to a CD4 antigen polypeptide.

The term "compete for binding" as used herein with respect to two antigen-binding proteins (e.g., antibodies), means that one antigen-binding protein blocks or reduces binding of the other to the antigen (e.g., human/mouse CD4), as determined by a competitive binding assay. Competitive binding assays are well known in the art, include, for example, direct or indirect radioimmunoassay (RIA), direct or indirect enzyme immunoassay (EIA), Fortebio, competition ELISA assay, and sandwich competition assay (see, e.g., Stahli et al., 1983, Methods in Enzymology 9:242-253). Typically, such an assay involves the use of purified antigen bound to a solid surface or cells bearing the antigen, an unlabeled test antibody and a labeled reference antibody. Competitive inhibition is measured by determining the amount of label bound to the solid surface or cells in the presence of the test antibody. Usually, the test antibody is present in excess. If two antibodies compete for binding to the hCD4, then the two antibodies bind to the same or overlapping epitope, or an adjacent epitope sufficiently proximal to the epitope bound by the other antibody for steric hindrance to occur. Usually, when a competing antibody is present in excess, it will inhibit (e.g., reduce) specific binding of a test antibody to a common antigen by at least 50-55%, 55-60%, 60-65%, 65-70%, 70-75% 75-80%, 80-85%, 85-90% or more.

Bispecific Antibodies

In certain embodiments, the antibodies and antigen-binding fragments thereof provided herein are bispecific. The term "bispecific" as used herein encompasses molecules having more than two specificity and molecules having more than two specificity, i.e., multi-specific. In certain embodiments, the bispecific antibodies and antigen-binding fragments thereof provided herein is capable of specifically binding to a first and a second epitopes of hCD4, or capable of specifically binding to hCD4 and a second antigen. In certain embodiments, the first epitope and the second epitopes of hCD4 are distinct from each other or non-overlapping. In certain embodiments, the bispecific antibodies and antigen-binding fragments thereof can bind to both the first epitope and the second epitope at the same time. In certain embodiments, the second antigen is different from hCD4.

In certain embodiments, the second antigen is an immune related target. An immune related target as used herein, encompasses a biological molecule that is involved in the generation, inhibition or modulation of an immune response, optionally, cellular immune responses. An example of the immune related target is immune checkpoint molecule that expresses on a tumor cell.

Immune checkpoint molecule can mediate co-stimulatory signal to augment immune response, or can mediate co-inhibitory signals to suppress immune response. Examples of an immune checkpoint molecule include, for example, PD-L1, PD-L2, PD-1, CTLA-4, TIM-3, LAG3, A2AR, CD160, 2B4, TGF β, VISTA, BTLA, TIGIT, LAIR1, OX40, CD2, CD27, CD28, CD30, CD40, CD47, CD122, ICAM-1, IDO, NKG2C, SLAMF7, SIGLEC7, NKp80, CD160, B7-H3, LFA-1, ICOS, 4-1BB, GITR, BAFFR, HVEM, CD7, LIGHT, IL-2, IL-7, IL-15, IL-21, CD3, CD16 and CD83. In certain embodiments, the second antigen comprises PD-1, PD-L1, CTLA-4, or LAG-3.

In certain embodiments, the second antigen comprises a tumor antigen. "Tumor antigen" as used herein refers to tumor specific antigens (e.g., those unique to tumor cells and normally not found on non-tumor cells), and tumor-associated antigens (e.g., found in both tumor and non-tumor cells but expressed differently in tumor cells, or found in tumor microenvironment). Tumor specific antigens can also include tumor neo-antigens (e.g., that are expressed in cancer cells because of somatic mutations that change the protein sequence or create fusion proteins between two unrelated sequences).

Examples of tumor antigens include, without limitation, prostate specific antigen (PSA), CA-125, gangliosides G(D2), G(M2) and G(D3), CD20, CD52, CD33, Ep-CAM, CEA, bombesin-like peptides, HER2/neu, epidermal growth factor receptor (EGFR), erbB2, erbB3/HER3, erbB4, CD44v6, Ki-67, cancer-associated mucin, VEGF, VEGFRs (e.g., VEGFR3), estrogen receptors, Lewis-Y antigen, TGFβ1, IGF-1 receptor, EGFα, c-Kit receptor, transferrin receptor, Claudin 18.2, GPC-3, Nectin-4, ROR1, methothelin, PCMA, MAGE-1, MAGE-3, BAGE, GAGE-1, GAGE-2, p15, BCR-ABL, E2APRL, H4-RET, IGH-IGK, MYL-RAR, IL-2R, CO17-1A, TROP2, or LIV-1.

Bispecific antibodies and antigen-binding fragments thereof provided herein can be in a suitable format known in the art. For example, an exemplary bispecific format can be, bispecific diabodies, scFv-based bispecific formats, IgG-scFv fusions, dual variable domain (DVD)-Ig, Quadroma, knobs-into-holes, common light chain (e.g., common light chain with knobs-into-holes, etc.), BiTE, CrossMab, Cross-Fab, Duobody, SEEDbody, leucine zipper, dual acting Fab (DAF)-IgG, and Mab$^2$ bispecific formats (see, e.g., Brinkmann et al. 2017, Mabs, 9(2): 182-212). The bispecific molecules can be in symmetric or asymmetric architecture.

The bispecific antibodies and antigen-binding fragments provided herein can be made with any suitable methods known in the art.

In one embodiment, two immunoglobulin heavy chain-light chain pairs having different antigenic specificities are co-expressed in a host cell to produce bispecific antibodies in a recombinant way (see, for example, Milstein and Cuello, Nature, 305: 537 (1983)), followed by purification by affinity chromatography.

Conjugates

In some embodiments, the anti-hCD4 antibodies and antigen-binding fragments thereof are linked to one or more conjugate moieties. A conjugate is a moiety that can be attached to the antibody or antigen-binding fragment thereof. It is contemplated that a variety of conjugates may be linked to the antibodies or antigen-binding fragments provided herein (see, for example, "Conjugate Vaccines", Contributions to Microbiology and Immunology, J. M. Cruse and R E. Lewis, Jr. (eds.), Carger Press, New York, (1989)). These conjugates may be linked to the antibodies or antigen-binding fragments by covalent binding, affinity binding, intercalation, coordinate binding, complexation, association, blending, or addition, among other methods. In certain embodiments, the antibodies or antigen binding fragments thereof are linked to one or more conjugates via a linker. In certain embodiments, the linker is a hydrazone linker, a disulfide linker, a bifunctional linker, dipeptide linker, glucuronide linker, a thioether linker.

In certain embodiments, the anti-hCD4 antibodies and antigen-binding fragments disclosed herein may be engineered to contain specific sites outside the epitope binding portion that may be utilized for binding to one or more conjugates. For example, such a site may include one or more reactive amino acid residues, such as for example cysteine or histidine residues, to facilitate covalent linkage to a conjugate.

The conjugate can be a clearance-modifying agent, therapeutic agent (e.g., a chemotherapeutic agent), a toxin, a radioactive isotope, a detectable label (e.g., a lanthanide, a luminescent label, a fluorescent label, or an enzyme-substrate label), a pharmacokinetic modifying moiety, a DNA-alkylator, a topoisomerase inhibitor, a tubulin-binders, other anticancer drugs called such as androgen receptor inhibitor.

Examples of detectable label may include a fluorescent label (e.g., fluorescein, rhodamine, dansyl, phycoerythrin, or Texas Red), enzyme-substrate labels (e.g., horseradish peroxidase, alkaline phosphatase, luciferase, glucoamylase, lysozyme, saccharide oxidases or β-D-galactosidase), radio-isotypes, other lanthanides, luminescent labels, chromophoric moiety, digoxigenin, biotin/avidin, a DNA molecule or gold for detection.

Examples of radioisotopes may include $^{123}$I, $^{124}$I, $^{125}$I, $^{131}$I, $^{35}$S, $^{3}$H, $^{111}$In, $^{112}$In, $^{14}$C, $^{64}$Cu, $^{67}$Cu, $^{86}$Y, $^{88}$Y, $^{90}$Y, $^{177}$Lu, $^{211}$At, $^{186}$Re, $^{188}$Re, $^{153}$Sm, $^{212}$Bi, and $^{32}$P. Radioisotope labelled antibodies are useful in receptor targeted imaging experiments.

In certain embodiments, the conjugate can be a pharmacokinetic modifying moiety such as PEG which helps increase half-life of the antibody. Other suitable polymers include, such as, carboxymethylcellulose, dextran, polyvinyl alcohol, polyvinyl pyrrolidone, copolymers of ethylene glycol/propylene glycol, and the like.

In certain embodiments, the conjugate can be a purification moiety such as a magnetic bead or a nanoparticle.

III. Pharmaceutical Composition

The present disclosure in another aspect provides pharmaceutical compositions comprising the anti-hCD4 antibodies or antigen-binding fragments thereof provided herein and one or more pharmaceutically acceptable carriers.

Pharmaceutical acceptable carriers for use in the pharmaceutical compositions disclosed herein may include, for example, pharmaceutically acceptable liquid, gel, or solid carriers, aqueous vehicles, nonaqueous vehicles, antimicrobial agents, isotonic agents, buffers, antioxidants, anesthetics, suspending/dispending agents, sequestering or chelating agents, diluents, adjuvants, excipients, or non-toxic auxiliary substances, other components known in the art, or various combinations thereof.

Suitable components may include, for example, antioxidants, fillers, binders, disintegrants, buffers, preservatives, lubricants, flavorings, thickeners, coloring agents, emulsifiers or stabilizers such as sugars and cyclodextrins. Suitable antioxidants may include, for example, methionine, ascorbic acid, EDTA, sodium thiosulfate, platinum, catalase, citric acid, cysteine, thioglycerol, thioglycolic acid, thiosorbitol, butylated hydroxanisol, butylated hydroxytoluene, and/or propyl gallate. As disclosed herein, inclusion of one or more antioxidants such as methionine in a composition comprising an antibody or antigen-binding fragment and conjugates as provided herein decreases oxidation of the antibody or antigen-binding fragment. This reduction in oxidation prevents or reduces loss of binding affinity, thereby improving antibody stability and maximizing shelf-life. Therefore, in certain embodiments compositions are provided that comprise one or more antibodies or antigen-binding fragments as disclosed herein and one or more antioxidants such as methionine. Further provided are methods for preventing oxidation of, extending the shelf-life of, and/or improving the efficacy of an antibody or antigen-binding fragment as provided herein by mixing the antibody or antigen-binding fragment with one or more antioxidants such as methionine.

To further illustrate, pharmaceutical acceptable carriers may include, for example, aqueous vehicles such as sodium chloride injection, Ringer's injection, isotonic dextrose injection, sterile water injection, or dextrose and lactated Ringer's injection, nonaqueous vehicles such as fixed oils of vegetable origin, cottonseed oil, corn oil, sesame oil, or peanut oil, antimicrobial agents at bacteriostatic or fungistatic concentrations, isotonic agents such as sodium chloride or dextrose, buffers such as phosphate or citrate buffers, antioxidants such as sodium bisulfate, local anesthetics such as procaine hydrochloride, suspending and dispersing agents such as sodium carboxymethylcelluose, hydroxypropyl methylcellulose, or polyvinylpyrrolidone, emulsifying agents such as Polysorbate 80 (TWEEN™-80), sequestering or chelating agents such as EDTA (ethylenediaminetetraacetic acid) or EGTA (ethylene glycol tetraacetic acid), ethyl alcohol, polyethylene glycol, propylene glycol, sodium hydroxide, hydrochloric acid, citric acid, or lactic acid. Antimicrobial agents utilized as carriers may be added to pharmaceutical compositions in multiple-dose containers that include phenols or cresols, mercurials, benzyl alcohol, chlorobutanol, methyl and propyl p-hydroxybenzoic acid esters, thimerosal, benzalkonium chloride and benzethonium chloride. Suitable excipients may include, for example, water, saline, dextrose, glycerol, or ethanol. Suitable non-toxic auxiliary substances may include, for example, wetting or emulsifying agents, pH buffering agents, stabilizers, solubility enhancers, or agents such as sodium acetate, sorbitan monolaurate, triethanolamine oleate, or cyclodextrin.

The pharmaceutical compositions can be a liquid solution, suspension, emulsion, pill, capsule, tablet, sustained release formulation, or powder. Oral formulations can include standard carriers such as pharmaceutical grades of mannitol, lactose, starch, magnesium stearate, polyvinyl pyrollidone, sodium saccharine, cellulose, magnesium carbonate, etc.

In certain embodiments, the pharmaceutical compositions are formulated into an injectable composition. The injectable pharmaceutical compositions may be prepared in any conventional form, such as for example liquid solution, suspension, emulsion, or solid forms suitable for generating liquid solution, suspension, or emulsion. Preparations for injection may include sterile and/or non-pyretic solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use, and sterile and/or non-pyretic emulsions. The solutions may be either aqueous or nonaqueous.

In certain embodiments, unit-dose parenteral preparations are packaged in an ampoule, a vial or a syringe with a needle. All preparations for parenteral administration should be sterile and not pyretic, as is known and practiced in the art.

In certain embodiments, a sterile, lyophilized powder is prepared by dissolving an antibody or antigen-binding fragment as disclosed herein in a suitable solvent. The solvent may contain an excipient which improves the stability or other pharmacological components of the powder or reconstituted solution, prepared from the powder. Excipients that may be used include, but are not limited to, water, dextrose, sorbital, fructose, corn syrup, xylitol, glycerin, glucose, sucrose or other suitable agent. The solvent may contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides a desirable formulation. In one embodiment, the resulting solution will be apportioned into vials for lyophilization. Each vial can contain a single dosage or multiple dosages of the anti-hCD4 antibody or antigen-binding fragment thereof or composition thereof. Overfilling vials with a small amount above that needed for a dose or set of doses (e.g., about 10%) is acceptable so as to facilitate accurate sample withdrawal and accurate dosing. The lyophilized powder can be stored under appropriate conditions, such as at about 4° C. to room temperature.

Reconstitution of a lyophilized powder with water for injection provides a formulation for use in parenteral administration. In one embodiment, for reconstitution the sterile and/or non-pyretic water or other liquid suitable carrier is added to lyophilized powder. The precise amount depends upon the selected therapy being given, and can be empirically determined.

In certain embodiments, the pharmaceutical composition further comprises a second therapeutic agent.

In certain embodiments, the second therapeutic agent can be an agent for treating cancer (i.e., an anti-cancer agent), for example, a chemotherapeutic agent, an anti-cancer drug (e.g., mTOR inhibitor), radiation therapy, an immunotherapy (e.g., an immune checkpoint inhibitor), anti-angiogenesis agent (e.g. antagonist of a VEGFR such as VEGFR-1, VEGFR-2, and VEGFR-3), a targeted therapy (e.g., a T cell recruiting antibody), a cellular therapy, a gene therapy agent, a hormonal therapy agent, cytokines, palliative care, surgery for the treatment of cancer (e.g., tumorectomy), or one or more anti-emetics or other treatments for complications arising from chemotherapy. Anti-angiogenesis agent can block the growth of blood vessels that support tumor growth. Some of the anti-angiogenesis agent target VEGF or its receptor VEGFR. Examples of anti-angiogenesis agent include, without limitation, Axitinib, Bevacizumab, Cabozantinib, Everolimus, Lenalidomide, Lenvatinib mesylate, Pazopanib, Ramucirumab, Regorafenib, Sorafenib, Sunitinib, Thalidomide, Vandetanib, and Ziv-aflibercept.

In certain embodiments, the second therapeutic agent comprises a T cell-recruiting antibody, for example, a CD19/CD3 bispecific antibody. The CD19/CD3 bispecific antibody can be designed in any format known in the art, such as the bispecific T-cell engager (BiTE) format (Nicola et al., Blood. (2018) 131(14): 1522-1531), and the single-chain Fv-Fc format (Hannah et al., Blood (2018) 132(5): 521-532). Exemplary CD19/CD3 bispecific antibodies include, without limitation, Blinatumomab (Nicola et al., Blood. (2018) 131(14): 1522-1531) and AFM11 (Uwe et al., MAbs. (2015) 7(3): 584-604.).

In certain embodiments, the second therapeutic agent comprises an immune checkpoint inhibitor selected from the group consisting of an PD-1 antibody, PD-L1 antibody, PD-L2 antibody, LAG-3 antibody, TIM-1 antibody, CTLA-4 antibody, VISTA antibody, B7-H2 antibody, B7-H3 antibody, B7-H4 antibody, B7-H antibody, ICOS antibody, HVEM antibody, CD160 antibody, gp49B antibody, PIR-B antibody, KIR family receptors antibody, TIM-1 antibody, TIM-4 antibody, BTLA antibody, SIRPalpha (CD47) antibody, CD244 antibody, B7.1 antibody, B7.2 antibody, ILT-2 antibody, ILT-4 antibody, TIGIT antibody and A2aR antibody. In certain embodiments, the second therapeutic agent comprises an mTOR inhibitor selected from the group consisting of Temsirolimus (CCI-779) or a pharmaceutical equivalent, analog, derivative or a salt thereof, Evirolimus (RAD001) or a pharmaceutical equivalent, analog, derivative or a salt thereof, and Rapamycin or a pharmaceutical equivalent, analog, derivative or a salt thereof.

In certain embodiments, the second therapeutic agent that manages or treats at least one complication associated with cancer.

IV. Polynucleotides and Recombinant Methods

The present disclosure in another aspect provides isolated polynucleotides that encode the anti-hCD4 antibodies and antigen-binding fragments thereof. The term "nucleic acid" or "polynucleotide" as used herein refers to deoxyribonucleic acids (DNA) or ribonucleic acids (RNA) and polymers thereof in either single- or double-stranded form. Unless otherwise indicated, a particular polynucleotide sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (see Batzer et al., Nucleic Acid Res. 19:5081 (1991); Ohtsuka et al., J. Biol. Chem. 260: 2605-2608 (1985); and Rossolini et al., Mol. Cell. Probes 8:91-98 (1994)).

In certain embodiments, the isolated polynucleotides comprise one or more nucleotide sequences as shown in SEQ ID NOs: 9, 10, 19, 20, 29, 30, 39, 40, 49, 50, 59 and 60, and/or a sequence having at least 80% (e.g., at least 85%, 88%, 90%, 92%, 93%, 94%, 95%, 96%, 97%, 98%, or 99%) sequence identity thereof, and/or a variant thereof having only degenerate substitutions, and encodes the variable region of the exemplary antibodies provided herein.

DNA encoding the monoclonal antibody is readily isolated and sequenced using conventional procedures (e.g., by using oligonucleotide probes that are capable of binding specifically to genes encoding the heavy and light chains of the antibody). The encoding DNA may also be obtained by synthetic methods.

The present disclosure provides vectors (e.g., expression vectors) comprising the isolated polynucleotide provided herein. In certain embodiments, the expression vector provided herein comprises the polynucleotide encoding the antibodies or antigen-binding fragments thereof provided herein, at least one promoter (e.g., SV40, CMV, EF-1α) operably linked to the polynucleotide sequence, and at least one selection marker. Examples of vectors include, but are not limited to, retrovirus (including lentivirus), adenovirus, adeno-associated virus, herpesvirus (e.g. herpes simplex virus), poxvirus, baculovirus, papillomavirus, papovavirus (e.g. SV40), lambda phage, and M13 phage, plasmids such as pcDNA3.3, pMD18-T, pOptivec, pCMV, pEGFP, pIRES, pQD-Hyg-GSeu, pALTER, pBAD, pcDNA, pCal, pL, pET, pGEMEX, pGEX, pCI, pEGFT, pSV2, pFUSE, pVITRO, pVIVO, pMAL, pMONO, pSELECT, pUNO, pDUO, Psg5L, pBABE, pWPXL, pBI, p15TV-L, pPro18, pTD, pRS10, pLexA, pACT2.2, pCMV-SCRIPT®, pCDM8, pCDNA1.1/amp, pcDNA3.1, pRc/RSV, PCR 2.1, pEF-1, pFB, pSG5, pXT1, pCDEF3, pSVSPORT, pEF-Bos etc.

Vectors comprising the polynucleotide sequence encoding the antibody or antigen-binding fragment thereof can be introduced to a host cell for cloning or gene expression. Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g. *Salmonella typhimurium*, *Serratia*, e.g. *Serratia marcescans*, and *Shigella*, as well as Bacilli such as *B. subtilis* and *B. licheniformis*, *Pseudomonas* such as *P. aeruginosa*, and *Streptomyces*.

In addition to prokaryotes, eukaryotic microbes such as filamentous fungi or yeast are suitable cloning or expression hosts for anti-hCD4 antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g. *K. lactis*, *K. fragilis* (ATCC 12,424), *K. bulgaricus* (ATCC 16,045), *K. wickeramii* (ATCC 24,178), *K. wallii* (ATCC 56,500), *K. drosophilarum* (ATCC 36,906), *K. thermotokrans*, and *K. marxianus; yarrowia* (EP 402,226); *Pichia pastoris* (EP 183,070); *Candida*; *Trichoderma reesia* (EP 244,234); *Neurospora crassa; Schwanniomyces* such as *Schwanniomyces occidentalis*; and filamentous fungi such as, e.g. *Neurospora*, *Penicillium*, *Tolypocladium*, and *Aspergillus* hosts such as *A. nidulans* and *A. niger*.

Suitable host cells for the expression of glycosylated antibodies or antigen-fragment provided herein are derived from multicellular organisms such as invertebrate cells, for example plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, 1-113 8065); mouse mammary tumor (MMT 060562, ATCC CCL51); TRI cells (Mather et al., *Annals N.Y. Acad. Sci.* 383:44-68

(1982)); MRC 5 cells; FS4 cells; and a human hepatoma line (Hep G2). In some preferable embodiments, the host cell is a mammalian cultured cell line, such as CHO, BHK, NS0, 293 and their derivatives.

Host cells are transformed with the above-described expression or cloning vectors for anti-hCD4 antibody production and cultured in conventional nutrient media modified as appropriate for inducing promoters, selecting transformants, or amplifying the genes encoding the desired sequences. In another embodiment, the antibody may be produced by homologous recombination known in the art.

The host cells used to produce the antibodies or antigen-binding fragments provided herein may be cultured in a variety of media. Commercially available media such as Ham's F10 (Sigma), Minimal Essential Medium (MEM), (Sigma), RPMI-1640 (Sigma), and Dulbecco's Modified Eagle's Medium (DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., Bio/Technology 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The anti-hCD4 antibodies and antigen-binding fragments thereof prepared from the cells can be purified using, for example, hydroxylapatite chromatography, gel electrophoresis, dialysis, DEAE-cellulose ion exchange chromatography, ammonium sulfate precipitation, salting out, and affinity chromatography, with affinity chromatography being the preferred purification technique.

In certain embodiments, Protein A immobilized on a solid phase is used for immunoaffinity purification of the antibody and antigen-binding fragment thereof. The suitability of protein A as an affinity ligand depends on the species and isotype of any immunoglobulin Fc domain that is present in the antibody. Protein A can be used to purify antibodies that are based on human gamma1, gamma2, or gamma4 heavy chains (Lindmark et al., J. Immunol. Meth. 62:1-13 (1983)). Protein G is recommended for all mouse isotypes and for human gamma3 (Guss et al., EMBO J. 5:1567 1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

V. Methods of Use

In one aspect, the present disclosure provides therapeutic uses of the antibodies provided herein.

In certain embodiments, the present disclosure provides methods of treating a CD4-related disease or condition in a subject in need thereof, comprising: administering a therapeutically effective amount of the antibody or antigen-binding fragment as provided herein and/or the pharmaceutical composition provided herein, thereby treating the CD4-related disease or condition.

A CD4-related disease or condition can be a disease or condition that would benefit from the CDC and/or ADCC activity on CD4-expressing cells, such as CD4+ T cells, especially Tregs. The CD4-related disease or condition can be cancer, adaptive immune disease, autoimmune disease, inflammatory disease, or infectious disease. In certain embodiments, the cancer is selected from the group consisting of lung cancer, bronchial cancer, bone cancer, liver and bile duct cancer, pancreatic cancer, breast cancer, liver cancer, ovarian cancer, testicle cancer, kidney cancer, bladder cancer, head and neck cancer, spine cancer, brain cancer, cervix cancer, uterine cancer, endometrial cancer, colon cancer, colorectal cancer, rectal cancer, anal cancer, esophageal cancer, gastrointestinal cancer, skin cancer, prostate cancer, pituitary cancer, stomach cancer, vagina cancer, thyroid cancer, glioblastoma, astrocytoma, melanoma, myelodysplastic syndrome, sarcoma, teratoma, adenocarcinoma, leukemia (e.g., chronic lymphocytic leukemia, relapsed or refractory B-cell precursor acute lymphoblastic leukemia), myeloma and lymphoma.

The present disclosure also provides a method of detecting presence or amount of CD4 in a sample, comprising contacting the sample with the antibody or antigen-binding fragment thereof provided herein, and determining the presence or the amount of CD4 in the sample.

Also provided herein is a method of diagnosing a CD4-related disease or condition in a subject, comprising: a) obtaining a sample from the subject; b) contacting the sample obtained from the subject with the antibody or antigen-binding fragment thereof provided herein; c) determining presence or amount of CD4 in the sample; and d) correlating the presence or the amount of CD4 to existence or status of the CD4 related disease or condition in the subject.

In another aspect, the present disclosure also provides a method of eliminating CD4-expressing cells in a subject in need thereof, comprising administering to the subject a therapeutically effective amount of the antibody or antigen-binding fragment thereof or the pharmaceutical composition provided herein. In certain embodiments, the CD4-expressing cell is a CD4+ T cell, optionally a regulatory T cell (Treg).

The term "CD4+ T cell" as used herein is defined as a thymus-derived lymphocyte with surface expression of CD4 that participates in a variety of cell-mediated immune reactions.

CD4+ T cells are crucial in achieving a regulated effective immune response to pathogens. Naïve CD4+ T cells are activated and differentiate into specific subtypes depending mainly on the cytokine milieu of the microenvironment. Several subsets of CD4+ T cells, including T-helper 1 and T-helper 2, T-helper 9, T-helper 17, follicular helper T cell (Tfh) and regulatory T cell (Tregs) have been identified, and each of these subsets expresses unique combinations of cell surface receptors, transcription factors, and secreted cytokines (Luckheeram R V, et al., Clin Dev Immunol (2012) 2012: 925135). Th1 cells are responsible for control of intracellular pathogens such as viruses and some bacteria (Prete G D, et al., Allergy (1992) 47: 450). Th2 cells are critical in the elimination of large extracellular organisms (Prete G D, et al., Allergy (1992) 47: 450). Th9 cells are involved with defence against parasitic helminth infections (Rajamanickam A, et al., PLoS Neglected Tropical Diseases (2016) 10: e0004317; Hosseini M A S, et al., International Journal of Epidemiologic Research (2015) 2: 233). Th17 is important for immune response against extracellular bacteria and fungi (Annunziato F, et al., J Exp Med (2007) 204: 1849; Weaver C T, Immunity (2006) 24: 677). Tfh cells are required for promoting the survival and proliferation of germinal center B cells and supporting germinal center development (Ise W, et al., Immunity (2018) 48: 702; Mints M A, et al., Immunological Reviews (2020) 296: 48).

The activities of above effector T cell subsets can be balanced in part by a unique subpopulation of CD4+ T cells known as regulatory T cells (Tregs). Tregs specialize in maintaining homeostasis and self-tolerance, limit the development and progression of immune responses (Vignali D A, et al., Nature Reviews Immunology (2008) 8: 523). In certain embodiments, the CD4-expressing cell is Treg.

As used herein, the term "regulatory T cell" or the term "Treg" that can be used interchangeably, refers to a distinct population of T lymphocytes characterized by the expression of CD4, CD25, and/or the forkhead family transcription factor FoxP3. It is a minority subpopulation of CD4+ T cells that constitutively express CD25 and FoxP3 transcription factor. Tregs have immune suppressive properties conferred by restraining the activation, proliferation, and effector functions of a wide range of immune cells, such as CD8+ T cells, NK and NKT cells, B cells and antigen present cells (APCs). For specific examples, Tregs suppress tumor-specific T cells in ovarian cancer, and increased number of tumor-associated Tregs is often associated with reduced survival time (Curiel et al., Nat. Med. (2003) 9:562-567; Wolf et al., 2005, Clin. Cancer Res. 11:8326-8331 and Curiel et al., 2006, Meeting Abstract, Can. Immunity 6 Suppl. 1, p. 20). Similar observations have been made with respect to colorectal cancer (Pages et al., N. Engl. J. Med. (2005) 353:2654-2666), lung cancer (Woo et al., J. Immunol. (2002) 168:4272-4276), and glioblastoma multiforme (Andaloussi et al., Neuro-oncol. (2006) 8:234-243).

Tregs also negatively affect the immunity of a subject with some viral and parasitic infections. For example, accumulation of Tregs and resultant immune suppression have been detected in subjects with retroviral infections, Leishmania and malaria mouse models and a filarial-infected mouse model (Iwashiro et al., 2001, PNAS 98:9226-9230; Belkaid et al., Nature 420:502; Hisaeda et al., 2004, Nat. Med. 10:29 and Taylor et al., 2005, J. Immunol. 174:4924-4933). Studies further showed that reduction in the number of Tregs by antibody therapy resulted in a dramatic reduction in parasite numbers (Taylor et al., 2005, J. Immunol. 174:4924-4933).

The term "eliminating", "eliminates", "eliminated" or "elimination" with respect to Tregs as used herein refers to decrease or reduction in the amount or percentage of the Tregs, or complete depletion of the Tregs, or inhibits/reduces the production or function of the Tregs. The percentage of Tregs can be determined by any methods known in the art, such as flow cytometry. The function of Tregs can be measured by any methods known in the art, for example, by measuring the level of immunosuppressive cytokines and molecules expressed by the Tregs, e.g., Cytotoxic T-lymphocyte associated protein 4 (CTLA-4), Programmed death-1 ligand 1 (PD-L1), Transforming growth factor-beta (TGF-β), Receptor activator of nuclear factor-κB ligand (RANKL), LAG-3, glucoeortscotd-mduced tumor necrosis factor receptor family-related gene (GITR; TNFRSF18 glucoeortscotd-mduced tumor necrosis factor receptor family-related gene (GITR; TNFRSF18) and/or IL-10. These molecules act in concert to induce immune tolerance and promote tumor progression and metastases (see, e.g., WO2011109789A2) The function of Tregs can also be measured by assaying their suppressive effect on, for example, the proliferation of CD8 lymphocytes.

In another aspect, the present disclosure also provides a method of enhancing immunogenicity of tumor microenvironment in a subject in need thereof, comprising administering to the subject a therapeutically effective amount of the antibody or antigen-binding fragment thereof or the pharmaceutical composition provided herein. The term "tumor microenvironment" as used herein refers to the tissue, cell and environment (e.g. extracellular environment) that surround the tumor cell. Tumor microenvironment can comprise stromal cells such as fibroblasts, pericytes, endothelial cells, adipose cells, and bone marrow mesenchymal stromal cells (MSCs). In certain embodiments, tumor microenvironment also comprises a variety of immune cells, such as effector T cells (e.g., CD8+ effector T cells) and Tregs.

In the setting of malignancy, Tregs cells can suppress anticancer immunity, thereby hindering protective immunosurveillance of neoplasia, hampering effective antitumor immune responses, and promoting tumor development and progression (Baba J, et al., Blood (2012) 120: 2417; Togashi Y, et al., Nature Reviews Clinical Oncology (2019) 16: 356). Increased Tregs in the tumor microenvironment are associated with a worse prognosis in a variety of cancers (Shang B, et al., Scientific Rep (2015) 5: 15179; Saleh R, et al., Cancer Letters (2020) 490: 174). Treatments targeted Tregs have been proved effective in enhancing the immunogenicity of the tumor microenvironment (Togashi Y, et al., Nature Reviews Clinical Oncology (2019) 16: 356; Onizuka S, et al., Cancer Res (1999) 59: 3128; Rech A J, et al., Sci. Transl Med (2012) 4: 134; Sugiyama D, et al., Proc. Natl Acad. Sci. USA (2013) 110: 17945; Kurose K, et al., Clin. Cancer Res (2015) 21: 4327).

Studies have shown that CD4 antibody-based depletion of Tregs cells potentiated antitumor immune memory stimulated by mTOR inhibition (Wang Y, et al., Cancer Res (2014) 74: 2217; Kim H L, OncoImmunology (2014) 3: e29081), and its combination with CD4 or CD4 antibody therapy mediated a very potent, CD8-dependent, synergistic effect, leading to significant elongation of tumor-free survival of mice bearing neuroblastoma (Rego V, et al., Scientific Reports (2017) 7:14049). Near complete CD4 depletion was achieved in several trials of chimeric αCD4 antibodies for refractory cutaneous T-cell lymphoma and rheumatoid arthritis, and no serious infections or other dose-related toxicities were observed (Prinz J C, et al., J Am Acad Dermatol (1996) 34: 244; Moreland L W, et al., Arthritis & Rheumatism (1994) 37: 834; Moreland L W, et al., Arthritis & Rheumatism (1994) 38: 1581). Therefore, depleting Tregs by administering the anti-CD4 antibodies or antigen-binding fragments thereof provided herein to a subject can enhance immunogenicity of tumor microenvironment in the subject.

In another aspect, the present disclosure also provides a method of improving the therapeutic efficacy of cancer therapy (e.g., chemotherapy, immunotherapy, radiotherapy) in a subject in need thereof, comprising administering to the subject a therapeutically effective amount of the antibody or antigen-binding fragment thereof or the pharmaceutical composition provided herein. The term "immunotherapy" as used herein, refers to a type of therapy that stimulates immune system to fight against disease such as cancer or that boosts immune system in a general way. Immunotherapy includes passive immunotherapy by delivering agents with established tumor-immune reactivity (such as effector cells) that can directly or indirectly mediate anti-tumor effects and does not necessarily depend on an intact host immune system (such as an antibody therapy or CAR-T cell therapy). Immunotherapy can further include active immunotherapy, in which treatment relies on the in vivo stimulation of the endogenous host immune system to react against diseased cells with the administration of immune response-modifying agents. Examples of immunotherapy include, without limitation, checkpoint modulators, adoptive cell transfer, cytokines, oncolytic virus and therapeutic vaccines.

Checkpoint modulators can interfere with the ability of cancer cells to avoid immune system attack, and help the immune system respond more strongly to a tumor. Immune checkpoint molecule can mediate co-stimulatory signal to augment immune response, or can mediate co-inhibitory signals to suppress immune response. Examples of checkpoint modulators include, without limitation, modulators of PD-1, PD-L1, PD-L2, CTLA-4, TIM-3, LAG3, A2AR, CD160, 2B4, TGF β, VISTA, BTLA, TIGIT, LAIR1, OX40, CD2, CD27, CD28, CD30 CD40 CD47, CD122, ICAM-1, IDO, NKG2C, SLAMF7, SIGLEC7, NKp80, CD160, B7-H3, LFA-1, 1COS, 4-1BB, GITR, BAFFR, HVEM, CD7, LIGHT, IL-2, IL-7, IL-15, IL-21, CD3, CD16 and CD83. In certain embodiments, the immune checkpoint modulator comprises a PD-1/PD-L1 axis inhibitor.

Adoptive cell transfer, which is a treatment that attempts to boost the natural ability of the T cells to fight cancer. In this treatment, T cells are taken from the patient, and are expanded and activated in vitro. In certain embodiments, the T cells are modified in vitro to CAR-T cells. T cells or CAR-T cells that are most active against the cancer are cultured in large batches in vitro for 2 to 8 weeks. During this period, the patients will receive treatments such as chemotherapy and radiation therapy to reduce the body's immunity. After these treatments, the in vitro cultured T cells or CAR-T cells will be given back to the patient. In certain embodiments, the immunotherapy is CAR-T therapy.

Cytokine therapy can also be used to enhance tumor antigen presentation to the immune system. The two main types of cytokines used to treat cancer are interferons and interleukins. Examples of cytokine therapy include, without limitation, interferons such as interferon-α, -β, and -γ, colony stimulating factors such as macrophage-CSF, granulocyte macrophage CSF, and granulocyte-CSF, insulin growth factor (IGF-1), vascular endothelial growth factor (VEGF), transforming growth factor (TGF), fibroblast growth factor (FGF), interleukins such as IL-1, IL-1α, IL-2, IL-3, IL-4, IL-5, IL-6, IL-7, IL-8, IL-9, IL-10, IL-11, and IL-12, tumor necrosis factors such as TNF-α and TNF-β or any combination thereof.

Oncolytic viruses are genetically modified viruses that can kill cancer cells. Oncolytic virus can specifically infect tumor cells, thereby leading to tumor cell lysis followed by release of large amount of tumor antigens that trigger the immune system to target and eliminate cancer cells having such tumor antigens. Examples of oncolytic viruses include, without limitation, talimogenelaherparepvec.

Therapeutic vaccines work against cancer by boosting the immune system's response to cancer cells. Therapeutic vaccines can comprise non-pathogenic microorganism (e.g., *Mycobacterium bovis* Bacillus Calmette-Guérin, BCG), genetically modified virus targeting a tumor cell, or one or more immunogenic components. For example, BCG can be inserted directly into the bladder with a catheter and can cause an immune response against bladder cancer cells.

Bedi et al. (see, WO2011109789A2) has shown that tumors foster the accumulation of Tregs in their microenvironment, which suppress priming of tumor-reactive immune responses by some of the immunotherapies (e.g., vaccination, chemotherapy) mentioned above. Bedi et al., also showed that the tumor-induced immune suppression mediated via Tregs is a crucial determinant of the resistance of cancers to chemotherapy and tumor-targeted antibodies. As confirmed by a previous study, elimination of CD4-expressing cells with an anti-CD4 antibody could result in Treg elimination and thereby enhances tumor-specific immunity (see, e.g., US2017/0007698). As such, administration of the anti-CD4 antibodies or antigen binding fragment thereof provided herein can effectively eliminate CD4-expressing cells (including Tregs), and is capable of enhancing the therapeutic efficacy of cancer therapies.

In certain embodiments, the method provided herein further comprises administering a second therapeutic agent. The second therapeutic agent can comprise an anti-cancer agent, such as an mTOR inhibitor, an immune checkpoint inhibitor or a T cell-recruiting antibody.

In certain embodiments, the T cell-recruiting antibody comprises a CD19/CD3 bispecific antibody.

In certain embodiments, the second therapeutic agent comprises a T cell-recruiting antibody, for example, a CD19/CD3 bispecific antibody. The CD19/CD3 bispecific antibody can be designed in any format known in the art, such as the bispecific T-cell engager (BiTE) format, and the single-chain Fv-Fc format (Hannah et al., Blood. (2018) 132(5): 521-532). Exemplary CD19/CD3 bispecific antibodies include, without limitation, Blinatumomab and AFM11 (Uwe et al., MAbs. (2015) 7(3): 584-604.).

In another aspect, the present disclosure provides use of the antibody or antigen-binding fragment thereof provided herein in the manufacture of a medicament for treating a CD4-related disease or condition in a subject.

In another aspect, the present disclosure provides use of the antibody or antigen-binding fragment thereof provided herein in the manufacture of a medicament for eliminating CD4-expressing cells in a subject in need thereof.

In another aspect, the present disclosure provides use of the antibody or antigen-binding fragment thereof provided herein in the manufacture of a medicament for enhancing immunogenicity of tumor microenvironment in a subject in need thereof.

In another aspect, the present disclosure provides use of the antibody or antigen-binding fragment thereof provided herein in the manufacture of a medicament for improving the therapeutic efficacy of immunotherapy in a subject in need thereof.

Administration Route and Dosage Regime

The antibody or antigen-binding fragment as provided herein may be administered at a therapeutically effective dosage. The therapeutically effective amount of an antibody or antigen-binding fragment as provided herein will depend on various factors known in the art, such as for example body weight, age, past medical history, present medications, state of health of the subject and potential for cross-reaction, allergies, sensitivities and adverse side-effects, as well as the administration route and extent of disease development. Dosages may be proportionally reduced or increased by one of ordinary skill in the art (e.g., physician or veterinarian) as indicated by these and other circumstances or requirements.

In certain embodiments, the antibody or antigen-binding fragment as provided herein may be administered at a therapeutically effective dosage of about 0.01 mg/kg to about 100 mg/kg. In certain embodiments, the administration dosage may change over the course of treatment. In certain embodiments, the administration dosage may vary over the course of treatment depending on the reaction of the subject.

Dosage regimens may be adjusted to provide the optimum desired response (e.g., a therapeutic response). For example, a single dose may be administered, or several divided doses may be administered over time.

The antibodies and antigen-binding fragments disclosed herein may be administered by any route known in the art, such as for example parenteral (e.g., subcutaneous, intraperitoneal, intravenous, including intravenous infusion, intramuscular, or intradermal injection) or non-parenteral (e.g., oral, intranasal, intraocular, sublingual, rectal, or topical) routes.

Without wishing to be bound by any theory, while elimination of CD4-expressing cells (e.g., Tregs) has been shown to enhance the therapeutic efficacy of cancer therapy (see, e.g., US 2017/0007698; and WO2011109789A2), CD4 elimination or depletion before stimulation of immunity (as indicated by, e.g., increased level of IFN-γ) induced by specific tumors and/or in specific conditions may result in poor or even suppressed CD8 memory formation and faster tumor growth (see, e.g., Fukui et al., Cancer Immunol Immunother (2006) 55:538-546; and US 2017/0007698). Therefore, the anti-CD4 antibodies or antigen-binding fragment thereof provided herein is preferably administered to a subject in need thereof, after the subject is confirmed to have tumor-induced immunity.

The tumor-induced immunity in a subject can be determined by any method known in the art, for example, by comparing the immune stimulation level (e.g., the serum level of IFN-γ in a subject) with a reference level of immune stimulation (e.g., the reference serum level of IFN-γ). As used herein, the term "reference level" with respect to immune stimulation refers to a benchmark level which allows for comparison. A reference level may be chosen by the persons skilled in the art according to the desired purpose. Means for determining suitable reference levels are known to the persons skilled in the art, e. g. a reference level can be determined from experience, existing knowledge or data collected from clinical studies. For example, the reference level of immune stimulation can be the level of immune stimulation in a normal healthy person with the same gender and comparable body weight, and optionally having other factors that are also comparable, such as, the physical condition, medication history, diet, sleep, etc.

Combination Therapies

In some embodiments, the antibodies or antigen-binding fragments disclosed herein may be administered alone or in combination with one or more additional therapeutic means or agents, which can be selected based on the disease or condition to be treated.

In some embodiments, the antibodies or antigen-binding fragments disclosed herein may be administered for treating cancer in combination with a second anti-cancer drug, for example, a chemotherapeutic agent, an anti-cancer drug (e.g., mTOR inhibitor), radiation therapy, an immunotherapy (e.g., an immune checkpoint inhibitor), anti-angiogenesis agent, a targeted therapy, a cellular therapy, a gene therapy agent, a hormonal therapy agent, cytokines, palliative care, surgery for the treatment of cancer (e.g., tumorectomy), one or more anti-emetics, treatments for complications arising from chemotherapy, or a diet supplement for cancer patients.

Anti-angiogenesis agent can block the growth of blood vessels that support tumor growth. Some of the anti-angiogenesis agent target VEGF or its receptor VEGFR. Examples of anti-angiogenesis agent include, without limitation, Axitinib, Bevacizumab, Cabozantinib, Everolimus, Lenalidomide, Lenvatinib mesylate, Pazopanib, Ramucirumab, Regorafenib, Sorafenib, Sunitinib, Thalidomide, Vandetanib, and Ziv-aflibercept.

"Targeted therapy" is a type of therapy that acts on specific molecules associated with cancer, such as specific proteins that are present in cancer cells but not normal cells or that are more abundant in cancer cells, or the target molecules in the cancer microenvironment that contributes to cancer growth and survival. Targeted therapy targets a therapeutic agent to a tumor, thereby sparing of normal tissue from the effects of the therapeutic agent.

Targeted therapy can target, for example, tyrosine kinase receptors and nuclear receptors. Examples of such receptors include, erbB1 (EGFR or HER1), erbB2 (HER2), erbB3, erbB4, FGFR, platelet-derived growth factor receptor (PDGFR), and insulin-like growth factor-1 receptor (IGF-1R), estrogen receptors (ERs), nuclear receptors (NR) and PRs.

Targeted therapy can target molecules in tyrosine kinase or nuclear receptors signaling cascade, such as, Erk and PI3K/Akt, AP-2α, AP-2β, AP-2γ, mitogen-activated protein kinase (MAPK), PTEN, p53, p19ARF, Rb, Apaf-1, CD-95/Fas, TRAIL-R1/R2, Caspase-8, Forkhead, Box 03A, MDM2, IAPs, NF-kB, Myc, P13K, Ras, FLIP, heregulin (HRG) (also known as gp30), Bcl-2, Bcl-xL, Bax, Bak, Bad, Bok, Bik, Blk, Hrk, BNIP3, BimL, Bid, and EGL-1.

Targeted therapy can also target tumor-associated ligands such estrogen, estradiol (E2), progesterone, oestrogen, androgen, glucocorticoid, prolactin, thyroid hormone, insulin, P70 S6 kinase protein (PS6), Survivin, fibroblast growth factors (FGFs), EGF, Neu Differentiation Factor (NDF), transforming growth factor alpha (TGF-α), IL-1A, TGF-beta, IGF-1, IGF-II, IGFBPs, IGFBP proteases, and IL-10.

In another aspect, the present disclosure provides kits or pharmaceutical compositions comprising the antibody or antigen-binding fragment thereof provided herein and the second therapeutic agent, which may be formulated in one composition, or in different compositions. Instructions for use or indications can be further included to provide information on how combined therapy are to be carried out.

EXAMPLES

While the disclosure has been particularly shown and described with reference to specific embodiments (some of which are preferred embodiments), it should be understood by those having skill in the art that various changes in form and detail may be made therein without departing from the spirit and scope of the present disclosure as disclosed herein.

Example 1: Mouse Immunization and Production of Mouse Antibodies Against Human CD4

To generate antibodies against the human CD4, cDNAs encoding the open reading frame of the extracellular domain of hCD4 fused with a histidine tag (hCD4-HisTag), mouse Fc (hCD4-mFc), and human Fc tag (hCD4-hFc) obtained by PCR and subcloned into expression vector pcDNA3.1 (Invitrogen Cat. No: V-790), respectively. After transient expression in freestyle 293 cells, hCD4-HisTag was purified with NTA column (GE healthcare), hCD4-mFc and hCD4-hFc were purified with Protein A column (GE healthcare).

BALB/c mice were immunized subcutaneously every 2 weeks for 6 weeks with recombinant hCD4-mFc (100 μg/mouse) emulsified with an equal volume of Freund's complete/incomplete adjuvant. Three days before fusion, mice were boosted by intravenous injection of the antigen without adjuvant. Spleen cells ($1 \times 10^8$) from immunized mouse were fused with SP2/0 myeloma cells ($1.5 \times 10^7$) with PEG Hybri-Max™ (Sigma Inc., Cat. No:7181). After fusion, the cells were distributed into 96-well plates at 0.1 ml per well and incubated at 37° C., 5% $CO_2$ incubator. On day 1, an additional 0.1 ml media containing serum and HAT plus 2×methotrexate was added to each well. On day 3 and day 7, 0.1 ml of media from each well was replaced with 0.1 ml of fresh HT media. The screening typically occurred between days 8-9, and the culture supernatant from each well was tested for hCD4-hFc binding by ELISA. Subcloning was conducted to obtain individual hybridoma clones producing monoclonal antibodies. Each of the hybridomas was subjected to multiple rounds (3-4 rounds) of limiting dilution. For each round of subcloning, the clones were tested by ELISA binding analysis.

Example 2: Selection of the Anti-hCD4 Hybridoma Antibodies Based on Binding and Gene Reporter Assays The binding interaction between hybridoma antibody and human CD4-hFc was measured by ELISA. 96-well plates (Costar, Cat. No:9018) were coated with 100 μL of 2 μg/ml CD4-hFc (CrownBio) in PBS buffer (Hyclone, Cat. No: SH30256.01B) overnight at 4° C. The wells were aspirated and non-specific binding sites were blocked by adding 200 μL of blocking buffer containing 1% (w/v) of bovine serum albumin (BSA, Roche, Cat. No: 738328) and incubating for 1 hour at 37° C. After the plates are washed three times with PBS buffer containing 0.05% (v/v) Tween™ 20 (Sigma, Cat. No: P1379), 100 μL hybridoma supernatant or a serial concentrations of purified antibody (starting from 20 μg/mL) diluted in blocking buffer was added to each well and incubated at room temperature for 1 hour. The plates were washed and incubated with 100 μL/well of Goat anti-Mouse IgG (Thermo, Cat. No:31432) in blocking buffer for 60 min. After the plates were washed, 100 μL/well of substrate solution TMB (eBioscience, Cat. No:00-4201-56) was added, and the plates were incubated for 2 min at room temperature before 100 μL/well of 2N $H_2SO_4$ was added to stop the reaction. The colorimetric signals were monitored at 450 nm using a SpectraMax Plus microplate reader (Molecular Devices). For the purified antibody, data were analyzed using GraphPad Prism 5 to calculated the $EC_{50}$.

Cell binding analysis of anti-CD4 antibody was performed using 293T cell line stably expressing CD4 (CD4-293T). $2*10^5$ CD4-293T cells were added to each well of 96-well plate and incubated with the indicated hybridoma supernatant or a serial concentrations of purified antibody (starting from 20 μg/mL) at 4° C. for 1 h. After the cells were washed three times with FACS buffer, the secondary antibody (PE Goat anti-mouse: 1:200) was added to the cells at 100 μl/well, and incubated at 4° C. for 40 min. Cells were washed three times with FACS buffer and analyzed by FACS Array. The binding EC50 of purified antibody was calculated with GraphPad Prism 5.

Figure 2:
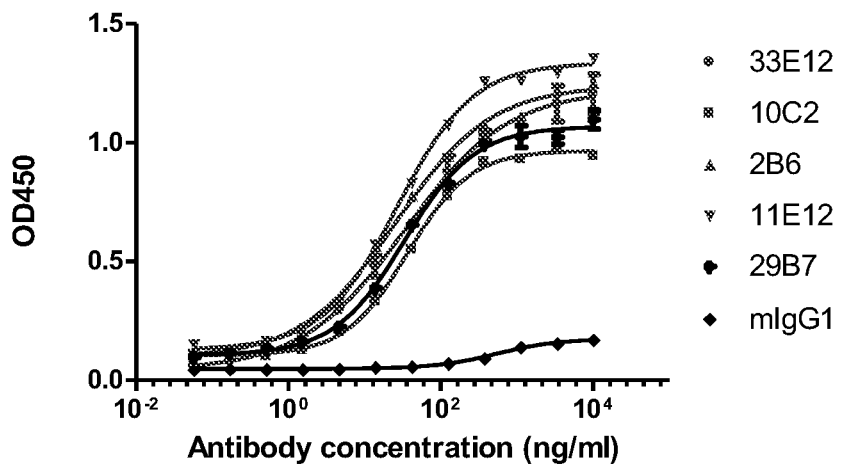
FIG. 2 shows the binding EC50 of the murine hybridoma anti-CD4 antibodies to human CD4 as measured by ELISA. The binding of mIgG1 is shown as a negative control.

Hybridoma clones with positive CD4 binding in both ELISA and FACS test were further screened with gene reporter assay. In 96-well plate, 40 μL CD4-293T cells were seeded at a density of $1*10^4$/well, and incubated with 20 μL culture medium from CD4-hFc binding positive hybridoma clones at 37° C., 5% $CO_2$ for 30 min. $1*10^5$ Jurkat-CD16a-NFAT-Luc cells (ADCC reporter T-cell line) in 40 μL medium were then added to each well, and continued the culture for 4 hours before adding 100 μL Bright-Glo reconstituted reagent (Promega, Cat. No: E2620). The luminescence signal from each well was monitored with EnVison multilabel plate reader (Perkin Elmer). It was found that the supernatant from hybridoma clone 2B6, 29B7, 33E12, 11E12, and 10C2 could induce NFAT activation and luciferase expression in the gene reporter assay, indicating that these hybridoma clones can induce ADCC effects (FIG. 1). These hybridoma clones were then adapted in serum free culture medium, and the antibodies were purified from the supernatant using Protein-A column (GE healthcare). The binding of these antibodies with human CD4 was quantified with ELISA (FIG. 2, Table 4).

TABLE 4

| EC50 of hybridoma antibody binding to hCD4 by ELISA | | | | | |
|---|---|---|---|---|---|
| Antibody | 33E12 | 10C2 | 2B6 | 11E12 | 29B7 |
| EC50 (ng/ml) | 33.95 | 36.78 | 26.13 | 26.98 | 33.39 |

Example 3: Anti-hCD4 Hybridoma Antibody Gene Cloning, Chimeric Antibody Generation and Characterization The total RNA of anti-hCD4 hybridoma clone 33E12, 10C2, 2B6, 11E12, 29B7 was isolated by RNeasy™ Mini Kit (Qiagen, Cat. No:74104) and used as the template to synthesize first-strand cDNA with SuperScript® II Reverse Transcriptase (Life Technology, Cat. No:18064-14) according to the manufacturer's instructions. The cDNA product was then subjected to PCR in a 50 µl volume reaction mixture using degenerate mouse IgG primers (Kettleborough C A, et al., (1993) European Journal of Immunology 23:206; Strebe N, et al., (2010) Antibody Engineering 1:3). The reaction was carried out in a S1000™ Thermal Cycler (Bio-Rad, Cat. No:184-2000) with 30 cycles of: 94° C., 1.5 minutes for denaturation; 50° C., 1 minutes for annealing; and 72° C., 1 minute for synthesis. At the end of the 30th cycle, the reaction mixture was incubated for additional 7 minutes at 72° C. for extension. The PCR mixture was subjected to electrophoresis in a 1% agarose/Tris™-Borate gel containing 0.5 µg/ml ethidium bromide. DNA fragments having the expected sizes (approximately 450 bp for the heavy chain and the light chain) were excised from the gel and purified. 3 µl of purified PCR product were cloned into the pMD-18T vector (Takara, Cat. No: D101A) and transformed into One Shot® TOP10 chemically competent *E. coli* (Invitrogen, CAT. NO: C4040-03). Clones were screened by colony PCR using universal M13 forward and reverse primers, and 5 positive clones from each reaction were chosen for DNA sequencing in both directions using M13 forward and M13 reverse primers. The heavy and light variable region sequences of antibody 33E12, 10C2, 2B6, 11E12 and 29B7 were listed in Table 2.

MT412 antibody produced by JL3A3.13 cell line (ATCC, Cat. No: PTA-6196) is a chimeric antibody which has a potent activity in CD4+ T cell depletion and immunogenicity in clinics (Prinz J C, et al., (1996) J Am Acad Dermatol 34: 244; Moreland L W, et al., (1994) Arthritis & Rheumatism 37: 834; Moreland L W, et al., (1994) Arthritis & Rheumatism 38: 1581). The heavy chain and light chain variable region sequences of antibody MT412 were determined by next generation sequencing (Table 2).

33E12, 10C2, 2B6, 11E12, 29B7 and MT412 chimeric light chains were constructed by linking the PCR-amplified cDNAs of mouse VL regions with human kappa chain constant region (SEQ ID NO: 62), respectively, and their chimeric heavy chains were constructed by linking the cDNAs of mouse VH regions with human IgG1 constant region which contained S298A/E333A/K334A mutations (Shields R L, et al., (2001) J Biol Chem 276: 6591). The 5'ends of the mouse cDNA sequences were modified using PCR primers designed to add a leader sequence to both light chain and heavy chain, and the DNA encoding the light chain and heavy chain of each chimeric antibody was subcloned into expression vector pcDNA3.1 (Invitrogen Cat. No: V-790), respectively.

IgG1 with 3A mutations
(SEQ ID NO: 67)
ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKV

EPKSCDKTHTCPPCPAPELLGGPSVFLFPPKPKDTLMISRTPEVTCVVV

DVSHEDPEVKFNWYVDGVEVHNAKTKPREEQYNATYRVVSVLTVLHQDW

LNGKEYKCKVSNKALPAPIAATISKAKGQPREPQVYTLPPSRDELTKNQ

VSLTCLVKGFYPSDIAVEWESNGQPENNYKTTPPVLDSDGSFFLYSKLT

VDKSRWQQGNVFSCSVMHEALHNHYTQKSLSLSPGK

Immunoglobulin kappa chain constant region
(SEQ ID NO: 68)
RTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPV

TKSFNRGEC

Figure 3:
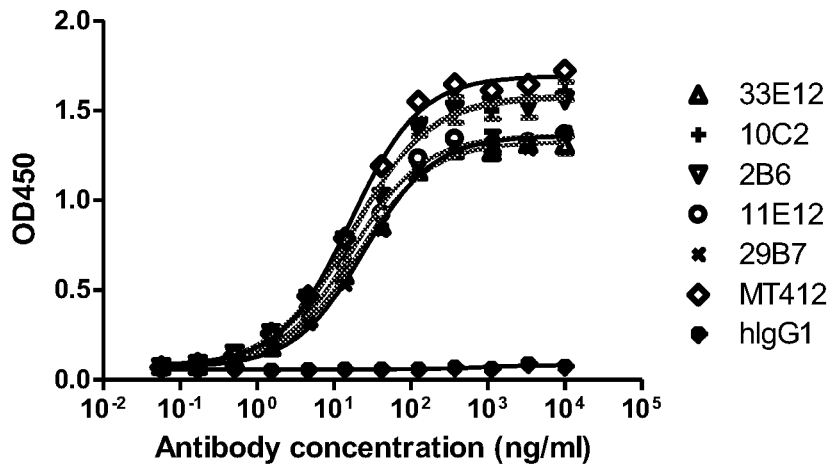
FIG. 3 shows the binding EC50 of the chimeric anti-CD4 antibodies to human CD4 as measured by ELISA.
Figure 4:
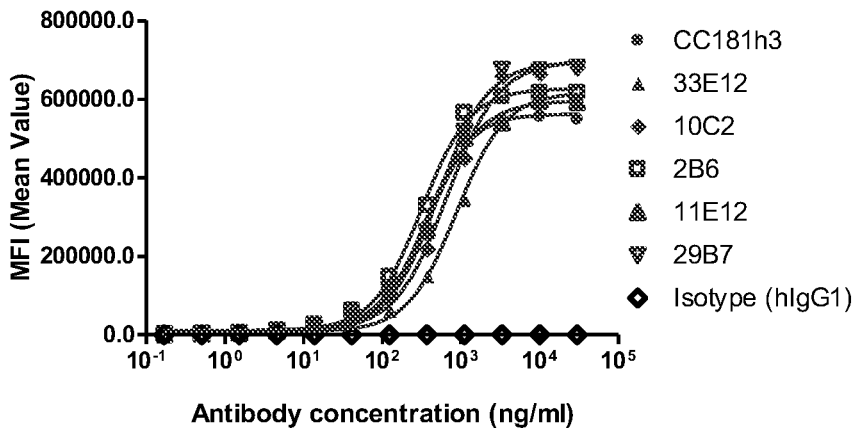
FIG. 4 shows the binding EC50 of the chimeric anti-CD4 antibodies to human CD4 on 293T-CD4 cells as measured by FACS.

Freestyle 293 cells (200 mL at 1*10^6/mL) were transfected with 100 µg of each of the chimeric heavy and light chain expression plasmids and cultured for 6 days at 37° C. The chimeric antibody in the supernatant was then purified with Protein-A column (GE healthcare). Binding of the chimeric antibody with CD4 was measured by ELISA (FIG. 3, Table 5) and FACS (FIG. 4, Table 6), using the similar methods described above in Example 2.

TABLE 5

EC50 of chimeric antibody binding to hCD4 by ELISA

| | Antibody | | | | | |
|---|---|---|---|---|---|---|
| | 33E12 | 10C2 | 2B6 | 11E12 | 29B7 | MT412 |
| EC50 (ng/ml) | 20.38 | 17.93 | 16.52 | 16.78 | 24.28 | 16.47 |

TABLE 6

EC50 of chimeric antibody binding to hCD4 by FACS

| | Antibody | | | | | |
|---|---|---|---|---|---|---|
| | 33E12 | 10C2 | 2B6 | 11E12 | 29B7 | MT412 |
| EC50 (ng/ml) | 351.4 | 882.4 | 669.3 | 316.1 | 400.9 | 515.2 |

Figure 5:
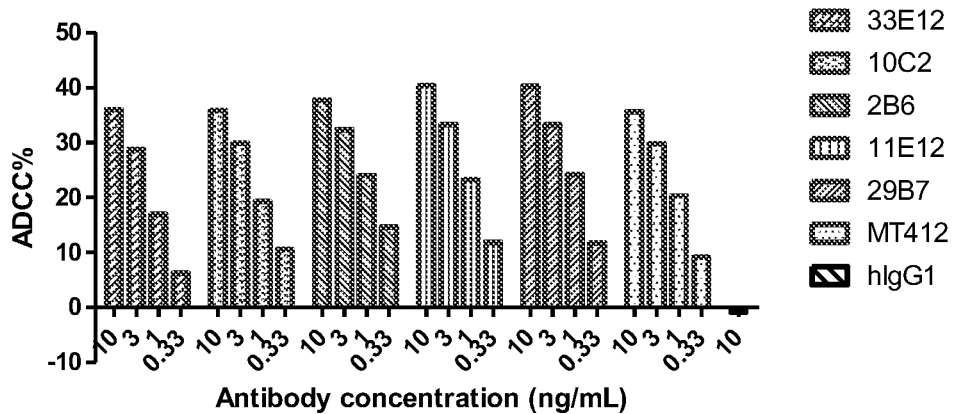
FIG. 5 shows the effect of chimeric anti-CD4 antibodies on the ADCC of CD4+ cells targeted by NK cells.

The ability of CD4 antibody to induce antibody-dependent cell-mediated cytotoxicity (ADCC) was assessed based on the killing of CD4-293T cells by natural killer (NK) cells evaluated by lactate dehydrogenase (LDH) measurement (Broussas M, et al., (2013) Methods Mol Biol 988:305). CD4-293T (2*10^4 cells/well) and human NK cells (2*10^5 cells/well) suspended in CTL Test Medium (Cellular Technology Limited) were seeded in a 96-well plate with serially diluted CD4 antibody (10 ng/mL, 3 ng/mL, 1 ng/mL, 0.3 ng/mL). After incubation for 4 hours at 37° C. in 5% $CO_2$, the LDH activities of cell culture supernatants were measured by using Cytotoxicity Detection KitPLUS (LDH) (Roche Applied Science). The percentage cytotoxicity was calculated as described in the manufacturer's protocol. As shown in FIG. 5, chimeric antibody 33E12, 10C2, 2B6, 11E12, 29B7 and MT412 elicited ADCC of CD4-293T in a dose dependent manner.

Example 4: Antibody Humanization Design, Humanized Antibody Generation and Characterization 2B6, 29B7 and MT412 antibody were humanized using the CDR grafting approach as described in U.S. Pat. No. 5,225,539. The light chain and heavy chain variable chain sequences of the murine antibody 2B6, 29B7 and MT412 were compared to those available in the Research Collaboratory for Structural Bioinformatics (RCSB) protein databank by searching the NCBI database. The model of antibody 2B6, 29B7 and MT412 were generated respectively based on the VH and VL structure with the highest sequence homology.

Human antibody germlines which have high sequence homology with 2B6, 29B7 and MT412 mouse antibody were obtained by searching the IMGT/Domain Gap Align 3D structure database. The frameworks of human germline antibodies were used as template for grafting the complementary determining regions (CDRs) from the VH and VL of mouse antibodies. For 2B6, the template human VH selected was a combination of IGHV4-59*11 and IGHJ4*01, and template human VL selected was a combination of IGKV1-39*01 and IGKJ2*01. For 29B7, the template human VH selected was a combination of IGHV1-3*01 and IGHJ4*01, and template human VL selected was a combination of IGKV1-16*01 and IGKJ2*01. For MT412, the template human VH selected was a combination of IGHV7-4-1*02 and IGHJ4*01, and template human VL selected was a combination of IGKV1-9*01 and IGKJ2*01.

CDR amino acid sequences of the aforementioned template human antibodies were substituted by the amino acid sequence of CDRs of mouse 2B6, 29B7 and MT412 antibody, respectively. In addition, the frameworks of the above-mentioned template human antibody VH and VL were grafted with the necessary amino acid sequences from VH and VL of mouse 2B6, 29B7 and MT412 antibody to give a functional humanized antibody. As for VH and VL of 2B6, 29B7 and MT412, several sites of framework amino acid of the aforementioned template human antibody were back mutated to the corresponding amino acid sequences in mouse 2B6, 29B7 and MT412 antibody. For the light chain variable region of humanized 2B6 antibody, the amino acid at position 4 was mutated from Met (M) to Leu (L) and the amino acid at position 71 was mutated from Phe (F) to Tyr (Y); and for the heavy chain variable region of humanized 2B6 antibody, the amino acid at position 27 was mutated from Gly (G) to Asp (D), the amino acid at position 30 was mutated from Ser (S) to Thr (T), the amino acid at position 47 was mutated from Trp (W) to Phe (F), the amino acid at position 48 was mutated from Ile (I) to Leu (L), and the amino acid at position 71 was mutated from Val (V) to Arg (R). For the light chain variable region of humanized 29B7 antibody, the amino acid at position 46 was mutated from Ser (S) to Thr (T), the amino acid at position 47 was mutated from Leu (L) to Pro (P), the amino acid at position 69 was mutated from Thr (T) to Gln (Q), and the amino acid at position 71 was mutated from Phe (F) to Tyr (Y); and for the heavy chain variable region of humanized 29B7 antibody, the amino acid at position 27 was mutated from Tyr (Y) to Asp (D), the amino acid at position 28 was mutated from Thr (T) to Ser (S), the amino acid at position 29 was mutated from Phe (F) to Leu (L), the amino acid at position 30 was mutated from Thr (T) to Asn (N), the amino acid at position 48 was mutated from Met (M) to Ile (I), the amino acid at position 68 was mutated from Val (V) to Ala (A), the amino acid at position 70 was mutated from Ile (I) to Leu (L), the amino acid at position 72 was mutated from Arg (R) to Ala (A), and the amino acid at position 74 was mutated from The (T) to Ile (I). For the light chain variable region of humanized MT412 antibody, the amino acid at position 4 was mutated from Leu (L) to Met (M) and the amino acid at position 87 was mutated from Tyr (Y) to Phe (F); for the heavy chain variable region of humanized MT412 antibody, the amino acid at position 2 was mutated from Val (V) to Ile (I).

The amino acid sequences of the variable light and variable heavy chains of humanized 2B6 antibody were designated SEQ ID NOs: 61 and 62, respectively. The amino acid sequences of the variable light and variable heavy chains of humanized 29B6 antibody were designated SEQ ID NOs: 63 and 64, respectively. The amino acid sequences of the variable light and variable heavy chains of humanized MT412 antibody were designated SEQ ID NOs: 65 and 66, respectively.

Figure 6:
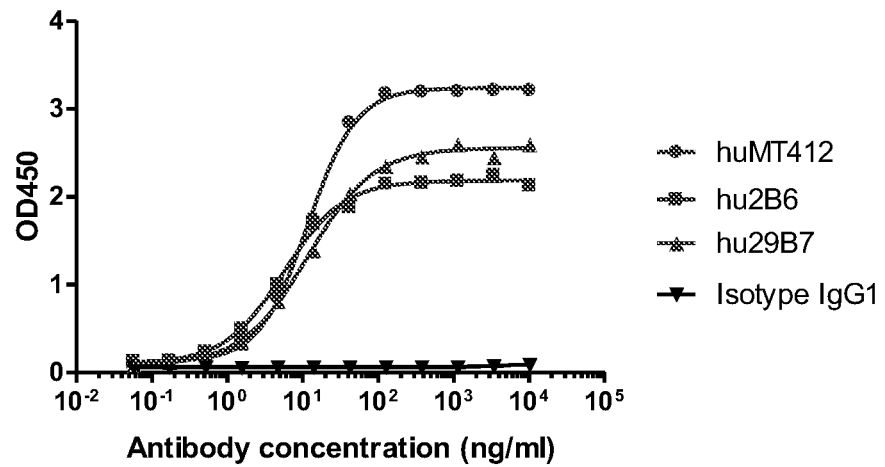
FIG. 6 shows the binding EC50 of the humanized anti-CD4 antibodies to human CD4 as measured by ELISA.
Figure 7:
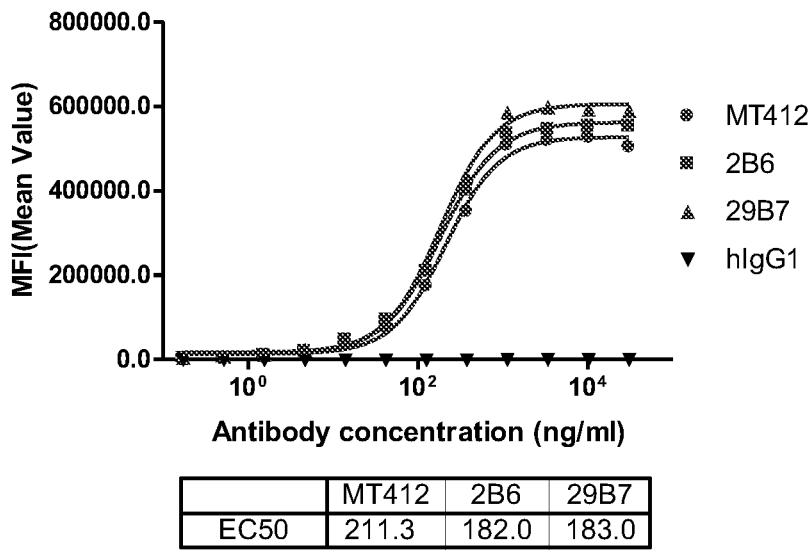
FIG. 7 shows the binding EC50 of the humanized anti-CD4 antibodies to human CD4 on 293T-CD4 cells as measured by FACS.

DNA encoding humanized 2B6, 29B7 and MT412 antibody light chain and heavy chain was synthesized and cloned to the expression vector pcDNA3.1 (Invitrogen, Cat. No: V-790). Freestyle 293 cells (200 mL at $10^6$/mL) were transfected with 100 µg of each of the humanized heavy and light chain expression plasmids and cultured for 6 days at 37° C. The humanized antibody in the supernatant was then purified with Protein-A column (GE healthcare). Binding of the chimeric antibody with CD4 was measured by ELISA (FIG. 6, Table 7) and FACS (FIG. 7, Table 8), and the methods used were similar to those described above in Example 2.

TABLE 7

EC50 of humanized antibody binding to hCD4 by ELISA

| Antibody | 2B6 | 29B7 | MT412 |
| --- | --- | --- | --- |
| EC50 (ng/ml) | 11.63 | 5.605 | 11.61 |

TABLE 8

EC50 of humanized antibody binding to hCD4 by FACS

| Antibody | 2B6 | 29B7 | MT412 |
| --- | --- | --- | --- |
| EC50 (ng/ml) | 211.3 | 182.0 | 183.0 |

Figure 8:
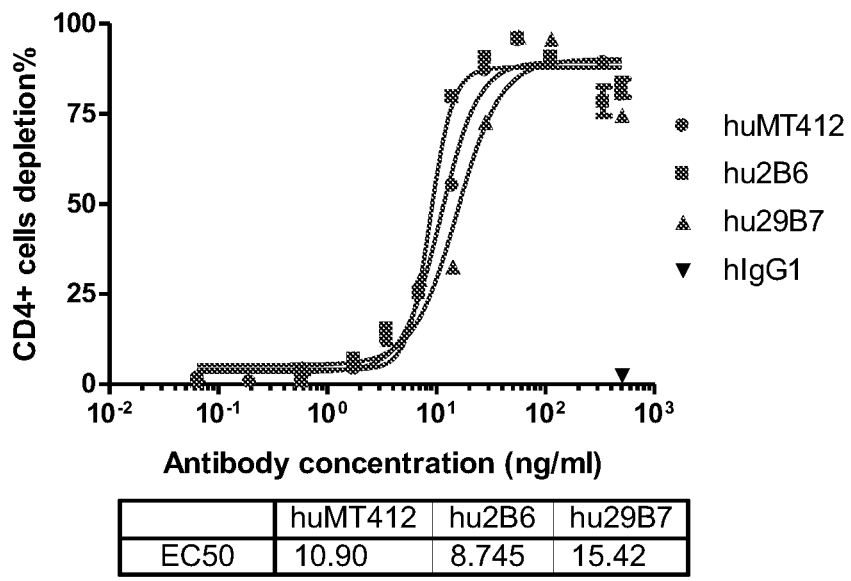
FIG. 8 shows the effect of humanized anti-CD4 antibodies on the ADCC of CD4+ cells in PBMC.

The ability of humanized CD4 antibody inducing ADCC was also evaluated with PBMC. In 96-well plate, PBMCs (2×10^5 cells/well) were incubated with series concentrations of humanized 2B6, 29B7 and MT412 antibody (1000 ng/mL, 100 ng/mL, 10 ng/mL, 1 ng/mL, 0.1 ng/mL, 0 ng/mL) at 37° C., 5% $CO_2$ for 4 and 24 hours. AF-488 labeled CD4 antibody (OKT4-AF488, the binding epitope of OKT4 antibody is not overlap with humanized 2B6, 29B7 and MT412 antibody) was then added to each well and incubated at 4° C. for 1 hour, and living CD4+ cells in each well were detected with FACS. The ADCC effect was shown in FIG. 8 by calculating with the following formula:

ADCC %=(1−No. of living CD4+ cells in the presence of antibody/No. of living CD4+ cells in the absence of antibody)×100%

The binding kinetics between CD4 and CD4 antibodies were measured by Biacore™ analysis, which was performed at 25° C. on a Biacore™ T200 instrument. Protein A (GE, Cat. No:29139131-AA) was diluted with 10 mM pH 5.0 sodium acetate and immobilized onto reference and experiment flow cells of a CM5 biosensor chip to around 15000 RU using an amine coupling kit (GE, BR10050). In the beginning of each cycle, diluted test antibody (1.5 µg/mL) was injected over experiment flow cell for 1 minute to be captured. CD4-HisTag analyte series were prepared by diluting the stocks with running buffer to 100 nM followed by 2-fold serial dilution in the same buffer down to 0.78 nM. Analytes were injected in series over the reference and experiment flow cells for 3 minutes at a flow rate of 30

μL/minute. Running buffer (PBS with 0.05% P20) was allowed to flow over for 10 minutes at a flow rate of 30 μL/minute. At the end of each cycle, the biosensor surface was regenerated with 3-minute injection of 10 mM pH 2.0 Glycine-HCl buffer at a flow rate of 10 μL/minute. For each analyte sample injection (i.e., each cycle), binding responses obtained from the experimental biosensor surface were double referenced by subtracting simultaneously recorded responses from the reference surface followed by additional subtraction of responses from a single referenced running buffer sample. The association and dissociation rate constants (ka and kd) were determined simultaneously by fitting double-referenced sensorgrams of the entire titration series to Langmuir model (1:1) using Biaevaluation software. The dissociation constant, KD, was calculated from the determined rate constants by the equation KD=kd/ka. The binding affinity of chimeric and humanized anti-CD4 antibodies with human CD4-HisTag are summarized in Table 9.

TABLE 9

Binding kinetics of chimeric and humanized anti-CD4 antibody

| Antibody | Ka(1/Ms) | Kd(1/s) | KD(M) |
|---|---|---|---|
| Chimeric 33E12 | 1.09E+06 | 0.004612 | 4.25E−09 |
| Chimeric 10C2 | 1.60E+05 | 1.90E−04 | 1.19E−09 |
| Chimeric 2B6 | 3.27E+05 | 1.22E−04 | 3.73E−10 |
| Chimeric 11E12 | 9.87E+05 | 0.006182 | 6.26E−09 |
| Chimeric 29B7 | 7.09E+05 | 5.98E−05 | 8.43E−11 |
| Chimeric MT412 | 5.86E+05 | 9.41E−04 | 1.61E−09 |
| Humanized 2B6 | 5.20E+05 | 7.89E−05 | 1.52E−10 |
| Humanized 29B7 | 1.03E+06 | 4.57E−04 | 4.44E−10 |
| Humanized MT412 | 1.11E+06 | 1.99E−03 | 1.80E−09 |

TABLE 10

Sequences mentioned or used in the present application

| SEQ ID NO | Sequence | Annotation |
|---|---|---|
| 1 | SGYWN | 2B6-HCDR1 |
| 2 | YISFADTTNYNPSLKS | 2B6-HCDR2/11E12-HCDR2 |
| 3 | DDYGYYAMDY | 2B6-HCDR3 |
| 4 | RASQDIDNYLN | 2B6-LCDR1 |
| 5 | YTSRLHS | 2B6-LCDR2/11E12-LCDR2 |
| 6 | QQGNTLPT | 2B6-LCDR3/11E12-LCDR3 |
| 7 | EVQLQESGPSLVKPSQTLSLTCSVTGDSITS GYWNWIRKFPGHKLEFLGYISFADTTNYN PSLKSRVSITRDTSKNQFDLQLKSVTTEDT ATYHCARDDYGYYAMDYWGQGISVTVSS | 2B6-VH |
| 8 | DIHLTQTTSSLSASLGDRVTIICRASQDIDN YLNWYQLKPDGTLKLLIYYTSRLHSGVPS RFSGSGSGTEYSLTISNLEREDVATYFCQQ GNTLPTFGAGTKLELK | 2B6-VL |
| 9 | gaagtgcagcttcaggagtcaggacctagcctcgtgaaaccttct cagactctgtccctcacctgttctgtcactggcgactccatcacca gcggttactggaattggatccggaagttcccaggacataaacttg agttttgggtacataagtttcgctgataccactaactacaatccat ctctcaaaagtcgagtctccatcactcgagacacatccaagaacc agttcgacctgcagttgaagtctgtgactactgaggacacagcca catatcactgtgcaagagatgattatggttattatgcaatggactac tggggtcaaggaatatcagtcaccgtctcctca | 2B6-VH nucleic acid |
| 10 | gatatccacttgacacagactacatcctccctgtctgcctctctggg agacagagtcaccatcatttgtagggcaagtcaggacattgacaa ttatttgaactggtatcagctgaagccagatggaactcttaaactcc tgatctactacacatcaagactacactcaggagtcccatcaaggtt cagtggcagtgggtctggaacagaatattctctcaccattagcaa cctggaacgtgaagatgttgccacttacttttgccaacagggtaat acacttcccacgttcggtgctgggaccaagctggagctgaaa | 2B6-VL nucleic acid |
| 11 | THWME | 29B7-HCDR1 |
| 12 | YINPYTGSGEYSQKFKG | 29B7-HCDR2 |
| 13 | DSTGAMDY | 29B7-HCDR3 |
| 14 | KASQDINRYLS | 29B7-LCDR1 |
| 15 | RADRSVD | 29B7-LCDR2 |

TABLE 10-continued

Sequences mentioned or used in the present application

| SEQ ID NO | Sequence | Annotation |
|---|---|---|
| 16 | YDEFPYT | 29B7-LCDR3 |
| 17 | QVQLQQSGAELAKPGASVKMSCKTSADS LNTHWMFIWVKQRPGQGLEWIGYINPYT GSGEYSQKFKGKATLTADISSSTAYMQLIS LTSEDSAVYYCAYDSTGAMDYWGQGTSV TVSS | 29B7-VH |
| 18 | DIKMTQSPSSMYASLGERITITCKASQDIN RYLSWFQQKPGKSPKTPIYRADRSVDGVP SRFSGSGSGQDYSLTISSLEYEDMGIYYCQ QYDEFPYTEGGGTKLEIK | 29B7-VL |
| 19 | caggtccagcttcagcagtctggggctgaactggcaaaacctgg ggcctcagtgaagatgtcctgcaagacttctgccgcagagccttaa tacccactggatgcactgggtaaaacagaggcctggacagggtc tggaatggattggatacattaatccttacactggttctggtgaatac agtcagaagttcaagggcaaggccacattgactgcagacatatc ctccagcacagcctacatgcaactgatcagcctgacatctgagga ctcagcagtctattactgtgcctatgattcgacaggtgccatggact actggggtcagggaacctcagtcaccgtctcctca | 29B7-VH nucleic acid |
| 20 | gacatcaagatgacccagtctccatcttccatgtatgcatctctagg agagagaatcactatcacttgcaaggcgagtcaggacattaatag gtatttaagctggttccagcagaaaccagggaaatctcctaagac cccgatctatcgtgcagacagatcggtagatggggtcccatcaa ggttcagtggcagtggatctgggcaagattattctcaccatcag cagcctggagtatgaggatatgggaatttattattgtcaacagtatg atgagtttccgtacacgttcggaggggggaccaagctggaaata aaa | 29B7-VL nucleic acid |
| 21 | SDYAWN | 33E12-HCDR1 |
| 22 | YISYSGITSYNPSLKS | 33E12-HCDR2 |
| 23 | LDSSGYGAMDY | 33E12-HCDR3 |
| 24 | RASQSVSTSSYSYMH | 33E12-LCDR1/10C2-LCDR1 |
| 25 | YASNLES | 33E12-LCDR2/10C2-LCDR2 |
| 26 | QHSWDFPLT | 33E12-LCDR3 |
| 27 | DVQLQESGPGLVKPSQSLSLTCTVTGYSIT SDYAWNWIRQFPGNKLEWMGYISYSGITS YNPSLKSRFSITRDTSKNQFFLQLNSVTTE DTATYYCARLDSSGYGAMDYWGQGTSV TVSS | 33E12-VH |
| 28 | DIVLTQSPASLPVSLGQRATISCRASQSVST SSYSYMHWYQQKPGQPPKLLIRYASNLES GVPARFSGSGSGTDFTLNIHPVEEEDTATY YCQHSWDFPLTFGAGTKLELK | 33E12-VL |
| 29 | gatgtgcagcttcaggagtcgggacctggcctggtgaaaccttct cagtctctgtccctcacctgcactgtcactggctactcaatcacca gtgattatgcctggaactggatccggcagtttccaggaaacaaac tggagtggatgggctacataagctacagtggtatcactagctaca acccatctctcaaaagtcgattctctatcactcgagacacatccaa gaaccagttcttcctgcagttgaattctgtgactactgaggacaca gccacatattactgtgcaaggctagacagctcgggctacggtgct atggactactggggtcaaggaacctcagtcaccgtctcctca | 33E12-VH nucleic acid |
| 30 | gacattgtgctgacacagtctcctgcttccttacctgtatctctggg gcagagggccaccatctcatgcagggccagccaaagtgtcagt acatctagtatagttatatgcactggtaccaacagaaaccagga cagccacccaaactcctcatcaggtatgcatccaacctagaatct ggggtccctgccaggttcagtggcagtgggtctgggacagactt cacccctcaacatccatcctgtggaggaggaggatactgcaacat attactgtcagcacagttgggactttccgctcacgttcggtgctgg gaccaagctggagctgaaa | 33E12-VL nucleic acid |

TABLE 10-continued

Sequences mentioned or used in the present application

| SEQ ID NO | Sequence | Annotation |
|---|---|---|
| 31 | SSYWN | 11E12-HCDR1 |
| 33 | DDFGYYAMDY | 11E12-HCDR3 |
| 34 | RASQDINNYLN | 11E12-LCDR1 |
| 37 | EVQLEESGPSLVKPSQTLSLTCSVTGDSITS SYWNWIRKFPGHKLEFLGYISFADTTNYN PSLKSRISITRDTSKNQFDLQLKSVTTEDT ATYYCARDDFGYYAMDYWGQGISVTVSS | 11E12-VH |
| 38 | DIYVTQTTSSLSASLGDRVTIICRASQDINN YLNWYQLKPDGTLKLLIYYTSRLHSGVPS RFGGSGSGTEYSLTISNLEQEDVATYFCQQ GNTLPTFGAGTKLELK | 11E12-VL |
| 39 | gaagtacagctggaggagtctggacctagcctcgtgaaaccttct cagactctgtccctcacctgttctgtcactggcgactccatcacca gcagttactggaattggatccggaagtttcccaggacataaacttg agttifiggggtacataagtttcgctgataccactaactacaatccat ctctcaaaagtcgaatctccatcactcgagacacatccaagaacc agttcgacctgcagttgaagtctgtgactactgaggacacagcca catattactgtgcaagagatgattttggttactatgcaatggactact ggggtcaagggatatcagtcactgtctcctca | 11E12-VH nucleic acid |
| 40 | gatatttacgtgacacagactacatcctccctgtctgcctctctggg agacagagtcaccatcatttgtagggcaagtcaggacattaacaa ttatttgaactggtatcagttgaagccagatggaactcttaaactcct gatctactacacatcaagactacactcaggagtcccatcaaggttc ggtggcagtgggtctggaacagaatattctctcaccattagcaac ctggaacaagaagatgttgccacttacttttgccaacagggtaata cacttcccacgttcggtgctgggaccaagctggagctgaaa | 11E12-VL nucleic acid |
| 41 | SYWIE | 10C2-HCDR1 |
| 42 | EILPGSGSTNYNEEFTG | 10C2-HCDR2 |
| 43 | SVSASNWYFDV | 10C2-HCDR3 |
| 46 | QHSWEIPPT | 10C2-LCDR3 |
| 47 | EVKLQQSGTELMKPGASVKISCKATGYTF SSYWIEWIKQRPGRGLEWIGEILPGSGSTN YNEEFTGRATFTADTFSNTAYMQLSSLTSE DSAVYYCARSVSASNWYFDVWGAGTTV TVSS | 10C2-VH |
| 48 | DIVMTQSPASLAVSLGQRATISCRASQSVS TSSYSYMHWYQQKPGQPPKFLIKYASNLE SGVPARFSGSGSGTDFTLNIHPVEEEDTAT YYCQHSWEIPPTFGGGTKLEIK | 10C2-VL |
| 49 | gaggtgaagctgcagcagtctggaactgagttgatgaagcctgg ggcctcagtgaagatatcctgcaaggctactggctacacattcag tagctactggatagagtggataaagcagaggcctggacgtggcc ttgagtggattggagagattttacctggaagtggtagtactaactac aatgaggagttcacgggcagggccacattcactgcagatacattt tccaatacagcctacatgcaactcagcagcctgacatctgaggac tctgccgtctattactgtgcaagatctgtttcggcttccaactggtac ttcgatgtctggggcgcaggaccacggtcaccgtctcgagc | 10C2-VH nucleic acid |
| 50 | gacattgtgatgacccaatctccagcttccctagctgtgtctctggg gcagagggccaccatctcatgcagggccagcaaagtgtcagt acatctagttacagttatatgcactggtaccaacagaagccagga cagccacccaaattcctcatcaaatatgcatccaacctggaatctg gggtccctgccaggttcagtggcagtgggtctggacagacttc accctcaacatccatcctgtgaggaggaggatactgcaacatat tactgtcagcacagttgggagattcctcccacgttcggagggggg gaccaagctggaaataaaa | 10C2-VL nucleic acid |
| 51 | DYSMH | MT412-HCDR1 |
| 52 | WINTETGEPTYADDFKG | MT412-HCDR2 |

TABLE 10-continued

Sequences mentioned or used in the present application

| SEQ ID NO | Sequence | Annotation |
|---|---|---|
| 53 | EDYYGHDGFLY | MT412-HCDR3 |
| 54 | KASQDVVTTVA | MT412-LCDR1 |
| 55 | WASLRHT | MT412-LCDR2 |
| 56 | QQYSSYPYT | MT412-LCDR3 |
| 57 | QIQLVQSGPELKKPGETVKISCKASGYTFT DYSMHVVVKQAPGKDLKWMGWINTETG EPTYADDFKGRFAFSLETSASTAYLQINNL KNEDTATYFCAREDYYGHDGFLYWGQGT LVTVSS | MT412-VH |
| 58 | DIVMTQSHKFMSTSVGDRVSITCKASQDV VTTVAWYQQKPGQSPKLLIYWASLRHTG VPDRFTGSGSGTDFTLTISNVQFEDLADYF CQQYSSYPYTEGGGTKLEIK | MT412-VL |
| 59 | cagatccagttggtgcagtctggacctgagctgaagaagcctgg agagacagtcaagatctcctgcaaggcttctggttataccttcaca gactattcaatgcactgggtgaagcaggctccaggaaaggattta aagtggatgggctggataaacactgagactggtgagccaacata tgcagatgacttcaagggacggtttgccttctctttggaaacctctg ccagcactgcctatttgcagatcaacaacctcaaaaatgaggaca cggctacatatttctgtgctagagaggactactatggtcacgacgg gtttctttactggggccaagggactctggtcactgtctctgca | MT412-VH nucleic acid |
| 60 | gacattgtgatgacccagtctcacaaattcatgtccacttcagtag gagacagggtcagcatcacctgcaaggccagtcaggatgtggtt actactgtagcctggtatcaacagaaaccagggcaatctcctaaa ctactgatttactgggcatcctccggcacactggagtccctgatc gcttcacaggcagtggatctgggacagatttcactctcaccattag caatgtgcagtttgaagacttggcagattattctgtcagcaatata gcagctatccgtacacgttcggaggggggaccaagctggaaat aaaa | MT412-VL nucleic acid |
| 61 | QVQLQESGPGLVKPSETLSLTCTVSGDSIT SGYWNWIRQPPGKGLEFLGYISFADTTNY NPSLKSRVTISRDTSKNQFSLKLSSVTAAD TAVYYCARDDYGYYAMDYWGQGTLVTV SS | 2B6 humanized-VH |
| 62 | DIQLTQSPSSLSASVGDRVTITCRASQDIDN YLNWYQQKPGKAPKLLIYYTSRLHSGVPS RFSGSGSGTDYTLTISSLQPEDFATYYCQQ GNTLPTFGQGTKLEIK | 2B6 humanized-VL |
| 63 | QVQLVQSGAEVKKPGASVKVSCKASGDS LNTHWMEIWVRQAPGQRLEWIGYINPYT GSGEYSQKFKGRATLTADISASTAYMELSS LRSEDTAVYYCAYDSTGAMDYWGQGTLV TVSS | 29B7 humanized-VH |
| 64 | DIQMTQSPSSLSASVGDRVTITCKASQDIN RYLSWFQQKPGKAPKTPIYRADRSVDGVP SRFSGSGSGQDYTLTISSLQPEDFATYYCQ QYDEFPYTFGQGTKLEIK | 29B7 humanized-VL |
| 65 | QIQLVQSGSELKKPGASVKVSCKASGYTF TDYSMEIWVRQAPGQGLEWMGWINTETG EPTYADDFKGRFVFSLDTSVSTAYLQISSL KAEDTAVYYCAREDYYGHDGFLWGQG TLVTVSS | MT412 humanized-VH |
| 66 | DIQMTQSPSFLSASVGDRVTITCKASQDV VTTVAWYQQKPGKAPKLLIYWASLRHTG VPSRFSGSGSGTEFTLTISSLQPEDFATYFC QQYSSYPYTFGQGTKLEIKR | MT412 humanized-VL |

TABLE 10-continued

Sequences mentioned or used in the present application

| SEQ ID NO | Sequence | Annotation |
|---|---|---|
| 67 | ASTKGPSVFPLAPSSKSTSGGTAALGCLVK DYFPEPVTVSWNSGALTSGVHTFPAVLQS SGLYSLSSVVTVPSSSLGTQTYICNVNHKP SNTKVDKKVEPKSCDKTHTCPPCPAPELL GGPSVFLFPPKPKDTLMISRTPEVTCVVVD VSHEDPEVKFNWYVDGVEVHNAKTKPRE EQYNATYRVVSVLTVLHQDWLNGKEYKC KVSNKALPAPIAATISKAKGQPREPQVYTL PPSRDELTKNQVSLTCLVKGFYPSDIAVEW ESNGQPENNYKTTPPVLDSDGSFFLYSKLT VDKSRWQQGNVFSCSVMHEALHNHYTQ KSLSLSPGK | Fc region of human IgG1 with 3A mutations |
| 68 | RTVAAPSVFIFPPSDEQLKSGTASVVCLLN NFYPREAKVQWKVDNALQSGNSQESVTE QDSKDSTYSLSSTLTLSKADYEKHKVYAC EVTHQGLSSPVTKSFNRGEC | Human immunoglobulin kappa light chain constant region |
| 69 | ASTKGPSVFPLAPSSKSTSGGTAALGCLVK DYFPEPVTVSWNSGALTSGVHTFPAVLQS SGLYSLSSVVTVPSSSLGTQTYICNVNHKP SNTKVDKKVEPKSCDKTHTCPPCPAPELL GGPSVFLFPPKPKDTLMISRTPEVTCVVVD VSHEDPEVKFNWYVDGVEVHNAKTKPRE EQYNSTYRVVSVLTVLHQDWLNGKEYKC KVSNKALPAPIEKTISKAKGQPREPQVYTL PPSRDELTKNQVSLTCLVKGFYPSDIAVEW ESNGQPENNYKTTPPVLDSDGSFFLYSKLT VDKSRWQQGNVFSCSVMHEALHNHYTQ KSLSLSPGK | Human IgG1 Fc region- wild type |

The invention claimed is:

1. An isolated antibody specifically binding to human CD4 (hCD4) or an antigen-binding fragment thereof, comprising a heavy chain variable (VH) region and a light chain variable (VL) region, wherein:
   a) the heavy chain variable region comprises a HCDR1 comprising the sequence of SEQ ID NO: 1, a HCDR2 comprising the sequence of SEQ ID NO: 2, and a HCDR3 comprising the sequence of SEQ ID NO: 3; and the light chain variable region comprises a LCDR1 comprising the sequence of SEQ ID NO: 4, a LCDR2 comprising the sequence of SEQ ID NO: 5, and a LCDR3 comprising the sequence of SEQ ID NO: 6; or
   b) the heavy chain variable region comprises a HCDR1 comprising the sequence of SEQ ID NO: 11, a HCDR2 comprising the sequence of SEQ ID NO: 12, and a HCDR3 comprising the sequence of SEQ ID NO: 13; and the light chain variable region comprises a LCDR1 comprising the sequence of SEQ ID NO: 14, a LCDR2 comprising the sequence of SEQ ID NO: 15, and a LCDR3 comprising the sequence of SEQ ID NO: 16; or
   c) the heavy chain variable region comprises a HCDR1 comprising the sequence of SEQ ID NO: 21, a HCDR2 comprising the sequence of SEQ ID NO: 22, and a HCDR3 comprising the sequence of SEQ ID NO: 23; and the light chain variable region comprises a LCDR1 comprising the sequence of SEQ ID NO: 24, a LCDR2 comprising the sequence of SEQ ID NO: 25, and a LCDR3 comprising the sequence of SEQ ID NO: 26; or
   d) the heavy chain variable region comprises a HCDR1 comprising the sequence of SEQ ID NO: 31, a HCDR2 comprising the sequence of SEQ ID NO: 2, and a HCDR3 comprising the sequence of SEQ ID NO: 33; and the light chain variable region comprises a LCDR1 comprising the sequence of SEQ ID NO: 34, a LCDR2 comprising the sequence of SEQ ID NO: 5, and a LCDR3 comprising the sequence of SEQ ID NO: 6; or
   e) the heavy chain variable region comprises a HCDR1 comprising the sequence of SEQ ID NO: 41, a HCDR2 comprising the sequence of SEQ ID NO: 42, and a HCDR3 comprising the sequence of SEQ ID NO: 43; and the light chain variable region comprises a LCDR1 comprising the sequence of SEQ ID NO: 24, a LCDR2 comprising the sequence of SEQ ID NO: 25, and a LCDR3 comprising the sequence of SEQ ID NO: 46.

2. The antibody or an antigen-binding fragment thereof of claim 1, wherein the heavy chain variable region comprises a sequence selected from the group consisting of SEQ ID NO: 7, SEQ ID NO: 17, SEQ ID NO: 27, SEQ ID NO: 37, SEQ ID NO: 47, SEQ ID NO: 61, and SEQ ID NO: 63.

3. The antibody or an antigen-binding fragment thereof of claim 1, wherein the light chain variable region comprises a sequence selected from the group consisting of SEQ ID NO: 8, SEQ ID NO: 18, SEQ ID NO: 28, SEQ ID NO: 38, SEQ ID NO: 48, SEQ ID NO: 62, and SEQ ID NO: 64.

4. The antibody or an antigen-binding fragment thereof of claim 1, comprising:
   a) a heavy chain variable region comprising the sequence of SEQ ID NO: 7 and a light chain variable region comprising the sequence of SEQ ID NO: 8; or
   b) a heavy chain variable region comprising a sequence of SEQ ID NO: 17 and a light chain variable region comprising a sequence of SEQ ID NO: 18; or
   c) a heavy chain variable region comprising a sequence of SEQ ID NO: 27 and a light chain variable region comprising a sequence of SEQ ID NO: 28; or
   d) a heavy chain variable region comprising a sequence of SEQ ID NO: 37 and a light chain variable region comprising a sequence of SEQ ID NO: 38; or
   e) a heavy chain variable region comprising a sequence of SEQ ID NO: 47 and a light chain variable region comprising a sequence of SEQ ID NO: 48; or
   f) a heavy chain variable region comprising a sequence of SEQ ID NO: 61 and a light chain variable region comprising a sequence of SEQ ID NO: 62; or
   g) a heavy chain variable region comprising a sequence of SEQ ID NO: 63 and a light chain variable region comprising a sequence of SEQ ID NO: 64.

5. The antibody or antigen-binding fragment thereof of claim 1, further comprising an immunoglobulin constant region, optionally a constant region of human Ig, or optionally a constant region of human IgG.

6. The antibody or antigen-binding fragment thereof of claim 5, wherein the constant region comprises a constant region of human IgG1, IgG2, IgG3, or IgG4.

7. The antibody or antigen-binding fragment thereof of claim 6, wherein the constant region comprises a constant region of human IgG1.

8. The antibody or antigen-binding fragment thereof of claim 7, wherein the IgG1 comprises one or more mutations that can confer increased CDC or ADCC relative to wild-type constant region.

9. The antibody or antigen-binding fragment thereof of claim 8, wherein the one or more mutations is selected from the group consisting of S239D, I332E, H268F, S324T S236A, G236A, P247I, A339D/Q, D280H, K290S, S298D/V, F243L, R292P, Y300L, P396L, V305I, K290E/N, S298G, T299A, K326E, E382V, M428I, S298A, K326A, E333A, and K334A, according to EU numbering.

10. The antibody or antigen-binding fragment thereof of claim 9, wherein the one or more mutations comprise a combination of S298A, E333A, and K334A, according to EU numbering.

11. The antibody or an antigen-binding fragment thereof of claim 1, which is humanized.

12. The antibody or antigen-binding fragment thereof of claim 1, which is a diabody, a Fab, a Fab', a F(ab')$_2$, a Fd, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), an scFv dimer (bivalent diabody), a multispecific antibody, or a nanobody.

13. The antibody or antigen-binding fragment thereof of claim 1, which is bispecific.

14. The antibody or antigen-binding fragment thereof of claim 13, which specifically binds to a first and a second epitope of hCD4, or specifically binds to hCD4 and a second antigen.

15. The antibody or antigen-binding fragment thereof of claim 14, wherein the second antigen is an immune checkpoint.

16. The antibody or antigen-binding fragment thereof of claim 14, wherein the second antigen is a tumor antigen.

17. The antibody or antigen-binding fragment thereof of any of claim 1, which is linked to one or more conjugate moieties.

18. The antibody or antigen-binding fragment thereof of claim 17, wherein the conjugate moiety is selected from the group consisting of a clearance-modifying agent, a chemotherapeutic agent, a toxin, a radioactive isotope, a lanthanide, a luminescent label, a fluorescent label, an enzyme-substrate label, a DNA-alkylator, a topoisomerase inhibitor, a tubulin-binders, and androgen receptor inhibitor.

19. A pharmaceutical composition or kit comprising the antibody or antigen-binding fragment thereof of claim 1, and a pharmaceutically acceptable carrier.

20. The pharmaceutical composition or kit of claim 19, further comprising a second therapeutic agent selected from an mTOR inhibitor, an immune checkpoint inhibitor and a T cell-recruiting antibody.

21. The pharmaceutical composition or kit of claim 20, wherein the mTOR inhibitor is Temsirolimus, Evirolimus or Rapamycin.

22. The pharmaceutical composition or kit of claim 20, wherein the immune checkpoint inhibitor is selected from an PD-1 antibody, PD-L1 antibody, PD-L2 antibody, LAG-3 antibody, TIM-1 antibody, CTLA-4 antibody, VISTA antibody, B7-H2 antibody, B7-H3 antibody, B7-H4 antibody, B7-H antibody 6, ICOS antibody, HVEM antibody, CD160 antibody, gp49B antibody, PIR-B antibody, KIR family receptors antibody, TIM-1 antibody, TIM-4 antibody, BTLA antibody, SIRPalpha (CD47) antibody, CD244 antibody, B7.1 antibody, B7.2 antibody, ILT-2 antibody, ILT-4 antibody, TIGIT antibody and A2aR antibody.

23. The pharmaceutical composition or kit of claim 20, wherein the T cell-recruiting antibody is a CD19/CD3 bispecific antibody.

24. An isolated polynucleotide encoding the antibody or an antigen-binding fragment thereof of claim 1.

25. A vector comprising the isolated polynucleotide of claim 24.

26. A host cell comprising the vector of claim 25.

27. A method of expressing an anti-hCD4 antibody or antigen-binding fragment thereof, comprising culturing the host cell of claim 26 under the condition at which the anti-hCD4 antibody or antigen-binding fragment thereof is expressed.

* * * * *

SEQUENCE LISTING

<160> NUMBER OF SEQ ID NOS: 69

<210> SEQ ID NO 1
<211> LENGTH: 5
<212> TYPE: PRT
<213> ORGANISM: mus musculus

<400> SEQUENCE: 1

Ser Gly Tyr Trp Asn
1               5

<210> SEQ ID NO 2
<211> LENGTH: 16
<212> TYPE: PRT
<213> ORGANISM: mus musculus

<400> SEQUENCE: 2

Tyr Ile Ser Phe Ala Asp Thr Thr Asn Tyr Asn Pro Ser Leu Lys Ser
1               5                   10                  15

<210> SEQ ID NO 3
<211> LENGTH: 10
<212> TYPE: PRT
<213> ORGANISM: mus musculus

<400> SEQUENCE: 3

Asp Asp Tyr Gly Tyr Tyr Ala Met Asp Tyr
1               5                   10

<210> SEQ ID NO 4

```
<211> LENGTH: 11
<212> TYPE: PRT
<213> ORGANISM: mus musculus

<400> SEQUENCE: 4

Arg Ala Ser Gln Asp Ile Asp Asn Tyr Leu Asn
1               5                   10

<210> SEQ ID NO 5
<211> LENGTH: 7
<212> TYPE: PRT
<213> ORGANISM: mus musculus

<400> SEQUENCE: 5

Tyr Thr Ser Arg Leu His Ser
1               5

<210> SEQ ID NO 6
<211> LENGTH: 8
<212> TYPE: PRT
<213> ORGANISM: mus musculus

<400> SEQUENCE: 6

Gln Gln Gly Asn Thr Leu Pro Thr
1               5

<210> SEQ ID NO 7
<211> LENGTH: 118
<212> TYPE: PRT
<213> ORGANISM: mus musculus

<400> SEQUENCE: 7

Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Gly
                20                  25                  30

Tyr Trp Asn Trp Ile Arg Lys Phe Pro Gly His Lys Leu Glu Phe Leu
            35                  40                  45

Gly Tyr Ile Ser Phe Ala Asp Thr Thr Asn Tyr Asn Pro Ser Leu Lys
        50                  55                  60

Ser Arg Val Ser Ile Thr Arg Asp Thr Ser Lys Asn Gln Phe Asp Leu
65                  70                  75                  80

Gln Leu Lys Ser Val Thr Thr Glu Asp Thr Ala Thr Tyr His Cys Ala
                85                  90                  95

Arg Asp Asp Tyr Gly Tyr Tyr Ala Met Asp Tyr Trp Gly Gln Gly Ile
            100                 105                 110

Ser Val Thr Val Ser Ser
        115

<210> SEQ ID NO 8
<211> LENGTH: 106
<212> TYPE: PRT
<213> ORGANISM: mus musculus

<400> SEQUENCE: 8

Asp Ile His Leu Thr Gln Thr Ser Ser Leu Ser Ala Ser Leu Gly
1               5                   10                  15

Asp Arg Val Thr Ile Ile Cys Arg Ala Ser Gln Asp Ile Asp Asn Tyr
                20                  25                  30

Leu Asn Trp Tyr Gln Leu Lys Pro Asp Gly Thr Leu Lys Leu Leu Ile
            35                  40                  45
```

```
Tyr Tyr Thr Ser Arg Leu His Ser Gly Val Pro Ser Arg Phe Ser Gly
        50                  55                  60

Ser Gly Ser Gly Thr Glu Tyr Ser Leu Thr Ile Ser Asn Leu Glu Arg
 65                  70                  75                  80

Glu Asp Val Ala Thr Tyr Phe Cys Gln Gln Gly Asn Thr Leu Pro Thr
                 85                  90                  95

Phe Gly Ala Gly Thr Lys Leu Glu Leu Lys
            100                 105

<210> SEQ ID NO 9
<211> LENGTH: 354
<212> TYPE: DNA
<213> ORGANISM: Artificial
<220> FEATURE:
<223> OTHER INFORMATION: Synthetic

<400> SEQUENCE: 9
gaagtgcagc ttcaggagtc aggacctagc ctcgtgaaac cttctcagac tctgtccctc      60
acctgttctg tcactggcga ctccatcacc agcggttact ggaattggat ccggaagttc     120
ccaggacata aacttgagtt tttggggtac ataagtttcg ctgataccac taactacaat     180
ccatctctca aaagtcgagt ctccatcact cgagacacat ccaagaacca gttcgacctg     240
cagttgaagt ctgtgactac tgaggacaca gccacatatc actgtgcaag agatgattat     300
ggttattatg caatggacta ctgggggtcaa ggaatatcag tcaccgtctc ctca          354

<210> SEQ ID NO 10
<211> LENGTH: 318
<212> TYPE: DNA
<213> ORGANISM: Artificial
<220> FEATURE:
<223> OTHER INFORMATION: Synthetic

<400> SEQUENCE: 10
gatatccact tgacacagac tacatcctcc ctgtctgcct ctctgggaga cagagtcacc      60
atcatttgta gggcaagtca ggacattgac aattatttga actggtatca gctgaagcca     120
gatggaactc ttaaactcct gatctactac acatcaagac tacactcagg agtcccatca     180
aggttcagtg gcagtgggtc tggaacagaa tattctctca ccattagcaa cctggaacgt     240
gaagatgttg ccacttactt ttgccaacag ggtaatacac ttcccacgtt cggtgctggg     300
accaagctgg agctgaaa                                                   318

<210> SEQ ID NO 11
<211> LENGTH: 5
<212> TYPE: PRT
<213> ORGANISM: mus musculus

<400> SEQUENCE: 11

Thr His Trp Met His
1               5

<210> SEQ ID NO 12
<211> LENGTH: 17
<212> TYPE: PRT
<213> ORGANISM: mus musculus

<400> SEQUENCE: 12

Tyr Ile Asn Pro Tyr Thr Gly Ser Gly Glu Tyr Ser Gln Lys Phe Lys
1               5                   10                  15
```

Gly

<210> SEQ ID NO 13
<211> LENGTH: 8
<212> TYPE: PRT
<213> ORGANISM: mus musculus

<400> SEQUENCE: 13

```
Asp Ser Thr Gly Ala Met Asp Tyr
1               5
```

<210> SEQ ID NO 14
<211> LENGTH: 11
<212> TYPE: PRT
<213> ORGANISM: mus musculus

<400> SEQUENCE: 14

```
Lys Ala Ser Gln Asp Ile Asn Arg Tyr Leu Ser
1               5                   10
```

<210> SEQ ID NO 15
<211> LENGTH: 7
<212> TYPE: PRT
<213> ORGANISM: mus musculus

<400> SEQUENCE: 15

```
Arg Ala Asp Arg Ser Val Asp
1               5
```

<210> SEQ ID NO 16
<211> LENGTH: 7
<212> TYPE: PRT
<213> ORGANISM: mus musculus

<400> SEQUENCE: 16

```
Tyr Asp Glu Phe Pro Tyr Thr
1               5
```

<210> SEQ ID NO 17
<211> LENGTH: 117
<212> TYPE: PRT
<213> ORGANISM: mus musculus

<400> SEQUENCE: 17

```
Gln Val Gln Leu Gln Gln Ser Gly Ala Glu Leu Ala Lys Pro Gly Ala
1               5                   10                  15

Ser Val Lys Met Ser Cys Lys Thr Ser Ala Asp Ser Leu Asn Thr His
            20                  25                  30

Trp Met His Trp Val Lys Gln Arg Pro Gly Gln Gly Leu Glu Trp Ile
        35                  40                  45

Gly Tyr Ile Asn Pro Tyr Thr Gly Ser Gly Tyr Ser Gln Lys Phe
    50                  55                  60

Lys Gly Lys Ala Thr Leu Thr Ala Asp Ile Ser Ser Thr Ala Tyr
65                  70                  75                  80

Met Gln Leu Ile Ser Leu Thr Ser Glu Asp Ser Ala Val Tyr Tyr Cys
                85                  90                  95

Ala Tyr Asp Ser Thr Gly Ala Met Asp Tyr Trp Gly Gln Gly Thr Ser
            100                 105                 110

Val Thr Val Ser Ser
        115
```

```
<210> SEQ ID NO 18
<211> LENGTH: 107
<212> TYPE: PRT
<213> ORGANISM: mus musculus

<400> SEQUENCE: 18

Asp Ile Lys Met Thr Gln Ser Pro Ser Ser Met Tyr Ala Ser Leu Gly
1               5                   10                  15

Glu Arg Ile Thr Ile Thr Cys Lys Ala Ser Gln Asp Ile Asn Arg Tyr
            20                  25                  30

Leu Ser Trp Phe Gln Gln Lys Pro Gly Lys Ser Pro Lys Thr Pro Ile
        35                  40                  45

Tyr Arg Ala Asp Arg Ser Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Gln Gln Tyr Asp Glu Phe Pro Tyr
                85                  90                  95

Thr Phe Gly Gly Gly Thr Lys Leu Glu Ile Lys
                100                 105

<210> SEQ ID NO 19
<211> LENGTH: 351
<212> TYPE: DNA
<213> ORGANISM: Artificial sequence
<220> FEATURE:
<223> OTHER INFORMATION: Synthetic

<400> SEQUENCE: 19
caggtccagc ttcagcagtc tggggctgaa ctggcaaaac ctggggcctc agtgaagatg     60
tcctgcaaga cttctgccga cagccttaat acccactgga tgcactgggt aaaacagagg    120
cctggacagg gtctggaatg gattggatac attaatcctt acactggttc tggtgaatac    180
agtcagaagt tcaagggcaa ggccacattg actgcagaca tatcctccag cacagcctac    240
atgcaactga tcagcctgac atctgaggac tcagcagtct attactgtgc ctatgattcg    300
acaggtgcca tggactactg gggtcaggga acctcagtca ccgtctcctc a             351

<210> SEQ ID NO 20
<211> LENGTH: 321
<212> TYPE: DNA
<213> ORGANISM: Artificial sequence
<220> FEATURE:
<223> OTHER INFORMATION: Synthetic

<400> SEQUENCE: 20
gacatcaaga tgacccagtc tccatcttcc atgtatgcat ctctaggaga gagaatcact     60
atcacttgca aggcgagtca ggacattaat aggtatttaa gctggttcca gcagaaacca    120
gggaaatctc ctaagacccc gatctatcgt gcagacagat cggtagatgg ggtcccatca    180
aggttcagtg gcagtggatc tgggcaagat tattctctca ccatcagcag cctggagtat    240
gaggatatgg gaatttatta ttgtcaacag tatgatgagt tcccgtacac gttcggaggg    300
gggaccaagc tggaaataaa a                                              321

<210> SEQ ID NO 21
<211> LENGTH: 6
<212> TYPE: PRT
<213> ORGANISM: mus musculus

<400> SEQUENCE: 21
```

```
Ser Asp Tyr Ala Trp Asn
1               5

<210> SEQ ID NO 22
<211> LENGTH: 16
<212> TYPE: PRT
<213> ORGANISM: mus musculus

<400> SEQUENCE: 22

Tyr Ile Ser Tyr Ser Gly Ile Thr Ser Tyr Asn Pro Ser Leu Lys Ser
1               5                   10                  15

<210> SEQ ID NO 23
<211> LENGTH: 11
<212> TYPE: PRT
<213> ORGANISM: mus musculus

<400> SEQUENCE: 23

Leu Asp Ser Ser Gly Tyr Gly Ala Met Asp Tyr
1               5                   10

<210> SEQ ID NO 24
<211> LENGTH: 15
<212> TYPE: PRT
<213> ORGANISM: mus musculus

<400> SEQUENCE: 24

Arg Ala Ser Gln Ser Val Ser Thr Ser Ser Tyr Ser Tyr Met His
1               5                   10                  15

<210> SEQ ID NO 25
<211> LENGTH: 7
<212> TYPE: PRT
<213> ORGANISM: mus musculus

<400> SEQUENCE: 25

Tyr Ala Ser Asn Leu Glu Ser
1               5

<210> SEQ ID NO 26
<211> LENGTH: 9
<212> TYPE: PRT
<213> ORGANISM: mus musculus

<400> SEQUENCE: 26

Gln His Ser Trp Asp Phe Pro Leu Thr
1               5

<210> SEQ ID NO 27
<211> LENGTH: 120
<212> TYPE: PRT
<213> ORGANISM: mus musculus

<400> SEQUENCE: 27

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Ser Tyr Ser Gly Ile Thr Ser Tyr Asn Pro Ser Leu
    50                  55                  60
```

Lys Ser Arg Phe Ser Ile Thr Arg Asp Thr Ser Lys Asn Gln Phe Phe
 65                  70                  75                  80

Leu Gln Leu Asn Ser Val Thr Thr Glu Asp Thr Ala Thr Tyr Tyr Cys
                 85                  90                  95

Ala Arg Leu Asp Ser Ser Gly Tyr Gly Ala Met Asp Tyr Trp Gly Gln
            100                 105                 110

Gly Thr Ser Val Thr Val Ser Ser
            115                 120

<210> SEQ ID NO 28
<211> LENGTH: 111
<212> TYPE: PRT
<213> ORGANISM: mus musculus

<400> SEQUENCE: 28

Asp Ile Val Leu Thr Gln Ser Pro Ala Ser Leu Pro Val Ser Leu Gly
1               5                   10                  15

Gln Arg Ala Thr Ile Ser Cys Arg Ala Ser Gln Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Arg Tyr Ala Ser Asn Leu Glu Ser Gly Val Pro Ala
 50                 55                  60

Arg Phe Ser Gly Ser Gly Ser Gly Thr Asp Phe Thr Leu Asn Ile His
 65                 70                  75                  80

Pro Val Glu Glu Glu Asp Thr Ala Thr Tyr Tyr Cys Gln His Ser Trp
                85                  90                  95

Asp Phe Pro Leu Thr Phe Gly Ala Gly Thr Lys Leu Glu Leu Lys
            100                 105                 110

<210> SEQ ID NO 29
<211> LENGTH: 360
<212> TYPE: DNA
<213> ORGANISM: Artificial sequence
<220> FEATURE:
<223> OTHER INFORMATION: Synthetic

<400> SEQUENCE: 29
gatgtgcagc ttcaggagtc gggacctggc ctggtgaaac cttctcagtc tctgtccctc      60
acctgcactg tcactggcta ctcaatcacc agtgattatg cctggaactg gatccggcag     120
tttccaggaa acaaactgga gtggatgggc tacataagct acagtggtat cactagctac     180
aacccatctc tcaaaagtcg attctctatc actcgagaca catccaagaa ccagttcttc     240
ctgcagttga attctgtgac tactgaggac acagccacat attactgtgc aaggctagac     300
agctcgggct acggtgctat ggactactgg ggtcaaggaa cctcagtcac cgtctcctca     360

<210> SEQ ID NO 30
<211> LENGTH: 333
<212> TYPE: DNA
<213> ORGANISM: Artificial sequence
<220> FEATURE:
<223> OTHER INFORMATION: Synthetic

<400> SEQUENCE: 30
gacattgtgc tgacacagtc tcctgcttcc ttacctgtat ctctggggca gagggccacc      60
atctcatgca gggccagcca agtgtcagt acatctagct atagttatat gcactggtac     120
caacagaaac caggacagcc acccaaactc ctcatcaggt atgcatccaa cctagaatct     180

-continued

```
ggggtccctg ccaggttcag tggcagtggg tctgggacag acttcaccct caacatccat    240
cctgtggagg aggaggatac tgcaacatat tactgtcagc acagttggga ctttccgctc    300
acgttcggtg ctgggaccaa gctggagctg aaa                                 333
```

<210> SEQ ID NO 31
<211> LENGTH: 5
<212> TYPE: PRT
<213> ORGANISM: mus musculus

<400> SEQUENCE: 31

Ser Ser Tyr Trp Asn
1               5

<210> SEQ ID NO 32

<400> SEQUENCE: 32

000

<210> SEQ ID NO 33
<211> LENGTH: 10
<212> TYPE: PRT
<213> ORGANISM: mus musculus

<400> SEQUENCE: 33

Asp Asp Phe Gly Tyr Tyr Ala Met Asp Tyr
1               5                   10

<210> SEQ ID NO 34
<211> LENGTH: 11
<212> TYPE: PRT
<213> ORGANISM: mus musculus

<400> SEQUENCE: 34

Arg Ala Ser Gln Asp Ile Asn Asn Tyr Leu Asn
1               5                   10

<210> SEQ ID NO 35

<400> SEQUENCE: 35

000

<210> SEQ ID NO 36

<400> SEQUENCE: 36

000

<210> SEQ ID NO 37
<211> LENGTH: 118
<212> TYPE: PRT
<213> ORGANISM: mus musculus

<400> SEQUENCE: 37

Glu Val Gln Leu Glu Glu Ser Gly Pro Ser Leu Val Lys Pro Ser Gln
1               5                   10                  15

Thr Leu Ser Leu Thr Cys Ser Val Thr Gly Asp Ser Ile Thr Ser Ser
            20                  25                  30

Tyr Trp Asn Trp Ile Arg Lys Phe Pro Gly His Lys Leu Glu Phe Leu
        35                  40                  45

Gly Tyr Ile Ser Phe Ala Asp Thr Thr Asn Tyr Asn Pro Ser Leu Lys
    50                  55                  60

```
Ser Arg Ile Ser Ile Thr Arg Asp Thr Ser Lys Asn Gln Phe Asp Leu
 65                  70                  75                  80

Gln Leu Lys Ser Val Thr Thr Glu Asp Thr Ala Thr Tyr Tyr Cys Ala
                 85                  90                  95

Arg Asp Asp Phe Gly Tyr Tyr Ala Met Asp Tyr Trp Gly Gln Gly Ile
            100                 105                 110

Ser Val Thr Val Ser Ser
        115

<210> SEQ ID NO 38
<211> LENGTH: 106
<212> TYPE: PRT
<213> ORGANISM: mus musculus

<400> SEQUENCE: 38

Asp Ile Tyr Val Thr Gln Thr Thr Ser Ser Leu Ser Ala Ser Leu Gly
  1               5                  10                  15

Asp Arg Val Thr Ile Ile Cys Arg Ala Ser Gln Asp Ile Asn Asn Tyr
                 20                  25                  30

Leu Asn Trp Tyr Gln Leu Lys Pro Asp Gly Thr Leu Lys Leu Leu Ile
             35                  40                  45

Tyr Tyr Thr Ser Arg Leu His Ser Gly Val Pro Ser Arg Phe Gly Gly
 50                  55                  60

Ser Gly Ser Gly Thr Glu Tyr Ser Leu Thr Ile Ser Asn Leu Glu Gln
 65                  70                  75                  80

Glu Asp Val Ala Thr Tyr Phe Cys Gln Gln Gly Asn Thr Leu Pro Thr
                 85                  90                  95

Phe Gly Ala Gly Thr Lys Leu Glu Leu Lys
            100                 105

<210> SEQ ID NO 39
<211> LENGTH: 354
<212> TYPE: DNA
<213> ORGANISM: Artificial sequence
<220> FEATURE:
<223> OTHER INFORMATION: Synthetic

<400> SEQUENCE: 39
gaagtacagc tggaggagtc tggacctagc ctcgtgaaac cttctcagac tctgtccctc      60
acctgttctg tcactggcga ctccatcacc agcagttact ggaattggat ccggaagttc     120
ccaggacata aacttgagtt tttggggtac ataagtttcg ctgataccac taactacaat     180
ccatctctca aaagtcgaat ctccatcact cgagacacat ccaagaacca gttcgacctg     240
cagttgaagt ctgtgactac tgaggacaca gccacatatt actgtgcaag agatgatttt     300
ggttactatg caatggacta ctggggtcaa gggatatcag tcactgtctc ctca           354

<210> SEQ ID NO 40
<211> LENGTH: 318
<212> TYPE: DNA
<213> ORGANISM: Artificial sequence
<220> FEATURE:
<223> OTHER INFORMATION: Synthetic

<400> SEQUENCE: 40
gatatttacg tgacacagac tacatcctcc ctgtctgcct ctctgggaga cagagtcacc      60
atcatttgta gggcaagtca ggacattaac aattatttga actggtatca gttgaagcca     120
gatggaactc ttaaactcct gatctactac acatcaagac tacactcagg agtcccatca     180
```

```
aggttcggtg gcagtgggtc tggaacagaa tattctctca ccattagcaa cctgaacaa      240 gaagatgttg ccacttactt ttgccaacag ggtaatacac ttcccacgtt cggtgctggg      300
accaagctgg agctgaaa                                                    318
```

<210> SEQ ID NO 41
<211> LENGTH: 5
<212> TYPE: PRT
<213> ORGANISM: mus musculus

<400> SEQUENCE: 41

```
Ser Tyr Trp Ile Glu
1               5
```

<210> SEQ ID NO 42
<211> LENGTH: 17
<212> TYPE: PRT
<213> ORGANISM: mus musculus

<400> SEQUENCE: 42

```
Glu Ile Leu Pro Gly Ser Gly Ser Thr Asn Tyr Asn Glu Glu Phe Thr
1               5                   10                  15

Gly
```

<210> SEQ ID NO 43
<211> LENGTH: 11
<212> TYPE: PRT
<213> ORGANISM: mus musculus

<400> SEQUENCE: 43

```
Ser Val Ser Ala Ser Asn Trp Tyr Phe Asp Val
1               5                   10
```

<210> SEQ ID NO 44

<400> SEQUENCE: 44

000

<210> SEQ ID NO 45

<400> SEQUENCE: 45

000

<210> SEQ ID NO 46
<211> LENGTH: 9
<212> TYPE: PRT
<213> ORGANISM: mus musculus

<400> SEQUENCE: 46

```
Gln His Ser Trp Glu Ile Pro Pro Thr
1               5
```

<210> SEQ ID NO 47
<211> LENGTH: 120
<212> TYPE: PRT
<213> ORGANISM: mus musculus

<400> SEQUENCE: 47

```
Glu Val Lys Leu Gln Gln Ser Gly Thr Glu Leu Met Lys Pro Gly Ala
1               5                   10                  15

Ser Val Lys Ile Ser Cys Lys Ala Thr Gly Tyr Thr Phe Ser Ser Tyr
```

```
                    20                  25                  30

Trp Ile Glu Trp Ile Lys Gln Arg Pro Gly Arg Gly Leu Glu Trp Ile
             35                  40                  45

Gly Glu Ile Leu Pro Gly Ser Gly Ser Thr Asn Tyr Asn Glu Glu Phe
     50                  55                  60

Thr Gly Arg Ala Thr Phe Thr Ala Asp Thr Phe Ser Asn Thr Ala Tyr
 65                  70                  75                  80

Met Gln Leu Ser Ser Leu Thr Ser Glu Asp Ser Ala Val Tyr Tyr Cys
                 85                  90                  95

Ala Arg Ser Val Ser Ala Ser Asn Trp Tyr Phe Asp Val Trp Gly Ala
            100                 105                 110

Gly Thr Thr Val Thr Val Ser Ser
            115                 120

<210> SEQ ID NO 48
<211> LENGTH: 111
<212> TYPE: PRT
<213> ORGANISM: mus musculus

<400> SEQUENCE: 48

Asp Ile Val Met Thr Gln Ser Pro Ala Ser Leu Ala Val Ser Leu Gly
  1               5                  10                  15

Gln Arg Ala Thr Ile Ser Cys Arg Ala Ser Gln Ser Val Ser Thr Ser
             20                  25                  30

Ser Tyr Ser Tyr Met His Trp Tyr Gln Gln Lys Pro Gly Gln Pro Pro
         35                  40                  45

Lys Phe Leu Ile Lys Tyr Ala Ser Asn Leu Glu Ser Gly Val Pro Ala
     50                  55                  60

Arg Phe Ser Gly Ser Gly Ser Gly Thr Asp Phe Thr Leu Asn Ile His
 65                  70                  75                  80

Pro Val Glu Glu Glu Asp Thr Ala Thr Tyr Tyr Cys Gln His Ser Trp
                 85                  90                  95

Glu Ile Pro Pro Thr Phe Gly Gly Gly Thr Lys Leu Glu Ile Lys
            100                 105                 110

<210> SEQ ID NO 49
<211> LENGTH: 360
<212> TYPE: DNA
<213> ORGANISM: Artificial sequence
<220> FEATURE:
<223> OTHER INFORMATION: Synthetic

<400> SEQUENCE: 49
gaggtgaagc tgcagcagtc tggaactgag ttgatgaagc ctggggcctc agtgaagata    60
tcctgcaagg ctactggcta cacattcagt agctactgga tagagtggat aaagcagagg   120
cctggacgtg gccttgagtg gattggagag attttacctg gaagtggtag tactaactac   180
aatgaggagt tcacgggcag ggccacattc actgcagata catttccaa tacagcctac    240 atgcaactca gcagcctgac atctgaggac tctgccgtct attactgtgc aagatctgtt   300
tcggcttcca actggtactt cgatgtctgg ggcgcaggga ccacggtcac cgtctcgagc   360

<210> SEQ ID NO 50
<211> LENGTH: 333
<212> TYPE: DNA
<213> ORGANISM: Artificial sequence
<220> FEATURE:
<223> OTHER INFORMATION: Synthetic
```

-continued

```
<400> SEQUENCE: 50
gacattgtga tgacccaatc tccagcttcc ctagctgtgt ctctggggca gagggccacc      60
atctcatgca gggccagcca agtgtcagt  acatctagtt acagttatat gcactggtac     120
caacagaagc caggacagcc acccaaattc ctcatcaaat atgcatccaa cctggaatct     180
ggggtccctg ccaggttcag tggcagtggg tctgggacag acttcaccct caacatccat     240
cctgtggagg aggaggatac tgcaacatat tactgtcagc acagttggga gattcctccc     300
acgttcggag gggggaccaa gctggaaata aaa                                  333

<210> SEQ ID NO 51
<211> LENGTH: 5
<212> TYPE: PRT
<213> ORGANISM: mus musculus

<400> SEQUENCE: 51

Asp Tyr Ser Met His
1               5

<210> SEQ ID NO 52
<211> LENGTH: 17
<212> TYPE: PRT
<213> ORGANISM: mus musculus

<400> SEQUENCE: 52

Trp Ile Asn Thr Glu Thr Gly Glu Pro Thr Tyr Ala Asp Asp Phe Lys
1               5                  10                  15

Gly

<210> SEQ ID NO 53
<211> LENGTH: 11
<212> TYPE: PRT
<213> ORGANISM: mus musculus

<400> SEQUENCE: 53

Glu Asp Tyr Tyr Gly His Asp Gly Phe Leu Tyr
1               5                   10

<210> SEQ ID NO 54
<211> LENGTH: 11
<212> TYPE: PRT
<213> ORGANISM: mus musculus

<400> SEQUENCE: 54

Lys Ala Ser Gln Asp Val Val Thr Thr Val Ala
1               5                   10

<210> SEQ ID NO 55
<211> LENGTH: 7
<212> TYPE: PRT
<213> ORGANISM: mus musculus

<400> SEQUENCE: 55

Trp Ala Ser Leu Arg His Thr
1               5

<210> SEQ ID NO 56
<211> LENGTH: 9
<212> TYPE: PRT
<213> ORGANISM: mus musculus

<400> SEQUENCE: 56
```

Gln Gln Tyr Ser Ser Tyr Pro Tyr Thr
1               5

<210> SEQ ID NO 57
<211> LENGTH: 120
<212> TYPE: PRT
<213> ORGANISM: mus musculus

<400> SEQUENCE: 57

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Asp Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Glu Asp Tyr Tyr Gly His Asp Gly Phe Leu Tyr Trp Gly Gln
            100                 105                 110

Gly Thr Leu Val Thr Val Ser Ser
        115                 120

<210> SEQ ID NO 58
<211> LENGTH: 107
<212> TYPE: PRT
<213> ORGANISM: mus musculus

<400> SEQUENCE: 58

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Val Thr Thr
            20                  25                  30

Val Ala Trp Tyr Gln Gln Lys Pro Gly Gln Ser Pro Lys Leu Leu Ile
        35                  40                  45

Tyr Trp Ala Ser Leu Arg His Thr Gly Val Pro Asp Arg Phe Thr Gly
    50                  55                  60

Ser Gly Ser Gly Thr Asp Phe Thr Leu Thr Ile Ser Asn Val Gln Phe
65                  70                  75                  80

Glu Asp Leu Ala Asp Tyr Phe Cys Gln Gln Tyr Ser Ser Tyr Pro Tyr
                85                  90                  95

Thr Phe Gly Gly Gly Thr Lys Leu Glu Ile Lys
            100                 105

<210> SEQ ID NO 59
<211> LENGTH: 360
<212> TYPE: DNA
<213> ORGANISM: Artificial sequence
<220> FEATURE:
<223> OTHER INFORMATION: Synthetic

<400> SEQUENCE: 59
cagatccagt tggtgcagtc tggacctgag ctgaagaagc ctggagagac agtcaagatc      60
tcctgcaagg cttctggtta taccttcaca gactattcaa tgcactgggt gaagcaggct     120
ccaggaaagg atttaaagtg gatgggctgg ataaacactg agactggtga gccaacatat     180

```
gcagatgact tcaagggacg gtttgccttc tctttggaaa cctctgccag cactgcctat    240
ttgcagatca acaacctcaa aaatgaggac acggctacat atttctgtgc tagagaggac    300
tactatggtc acgacgggtt tctttactgg ggccaaggga ctctggtcac tgtctctgca    360
```

<210> SEQ ID NO 60
<211> LENGTH: 321
<212> TYPE: DNA
<213> ORGANISM: Artificial sequence
<220> FEATURE:
<223> OTHER INFORMATION: Synthetic

<400> SEQUENCE: 60

```
gacattgtga tgacccagtc tcacaaattc atgtccactt cagtaggaga cagggtcagc     60
atcacctgca aggccagtca ggatgtggtt actactgtag cctggtatca acagaaacca    120
gggcaatctc ctaaactact gatttactgg gcatccctcc ggcacactgg agtccctgat    180
cgcttcacag gcagtggatc tgggacagat ttcactctca ccattagcaa tgtgcagttt    240
gaagacttgg cagattattt ctgtcagcaa tatagcagct atccgtacac gttcggaggg    300
gggaccaagc tggaaataaa a                                               321
```

<210> SEQ ID NO 61
<211> LENGTH: 118
<212> TYPE: PRT
<213> ORGANISM: Artificial sequence
<220> FEATURE:
<223> OTHER INFORMATION: Synthetic

<400> SEQUENCE: 61

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Thr Ser Gly
            20                  25                  30

Tyr Trp Asn Trp Ile Arg Gln Pro Pro Gly Lys Gly Leu Glu Phe Leu
        35                  40                  45

Gly Tyr Ile Ser Phe Ala Asp Thr Thr Asn Tyr Asn Pro Ser Leu Lys
    50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Asp Tyr Gly Tyr Tyr Ala Met Asp Tyr Trp Gly Gln Gly Thr
            100                 105                 110

Leu Val Thr Val Ser Ser
        115
```

<210> SEQ ID NO 62
<211> LENGTH: 106
<212> TYPE: PRT
<213> ORGANISM: Artificial sequence
<220> FEATURE:
<223> OTHER INFORMATION: Synthetic

<400> SEQUENCE: 62

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Asp Asn Tyr
            20                  25                  30
```

```
Leu Asn Trp Tyr Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Gly
 50                      55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Gln Gly Asn Thr Leu Pro Thr
                    85                  90                  95

Phe Gly Gln Gly Thr Lys Leu Glu Ile Lys
                100                 105

<210> SEQ ID NO 63
<211> LENGTH: 117
<212> TYPE: PRT
<213> ORGANISM: Artificial sequence
<220> FEATURE:
<223> OTHER INFORMATION: Synthetic

<400> SEQUENCE: 63

Gln Val Gln Leu Val Gln Ser Gly Ala Glu Val Lys Lys Pro Gly Ala
 1               5                  10                  15

Ser Val Lys Val Ser Cys Lys Ala Ser Gly Asp Ser Leu Asn Thr His
                20                  25                  30

Trp Met His Trp Val Arg Gln Ala Pro Gly Gln Arg Leu Glu Trp Ile
            35                  40                  45

Gly Tyr Ile Asn Pro Tyr Thr Gly Ser Gly Glu Tyr Ser Gln Lys Phe
 50                      55                  60

Lys Gly Arg Ala Thr Leu Thr Ala Asp Ile Ala Ser Thr Ala Tyr
 65                  70                  75                  80

Met Glu Leu Ser Ser Leu Arg Ser Glu Asp Thr Ala Val Tyr Tyr Cys
                    85                  90                  95

Ala Tyr Asp Ser Thr Gly Ala Met Asp Tyr Trp Gly Gln Gly Thr Leu
                100                 105                 110

Val Thr Val Ser Ser
        115

<210> SEQ ID NO 64
<211> LENGTH: 107
<212> TYPE: PRT
<213> ORGANISM: Artificial sequence
<220> FEATURE:
<223> OTHER INFORMATION: Synthetic

<400> SEQUENCE: 64

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Ile Asn Arg Tyr
                20                  25                  30

Leu Ser Trp Phe Gln Gln Lys Pro Gly Lys Ala Pro Lys Thr Pro Ile
            35                  40                  45

Tyr Arg Ala Asp Arg Ser Val Asp Gly Val Pro Ser Arg Phe Ser Gly
 50                      55                  60

Ser Gly Ser Gly Gln Asp Tyr Thr Leu Thr Ile Ser Ser Leu Gln Pro
 65                  70                  75                  80

Glu Asp Phe Ala Thr Tyr Tyr Cys Gln Gln Tyr Asp Glu Phe Pro Tyr
                    85                  90                  95

Thr Phe Gly Gln Gly Thr Lys Leu Glu Ile Lys
                100                 105
```

<210> SEQ ID NO 65
<211> LENGTH: 120
<212> TYPE: PRT
<213> ORGANISM: Artificial sequence
<220> FEATURE:
<223> OTHER INFORMATION: Synthetic

<400> SEQUENCE: 65

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Ser Met His Trp Val Arg Gln Ala Pro Gly Gln Gly Leu Glu Trp Met
        35                  40                  45

Gly Trp Ile Asn Thr Glu Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Glu Asp Tyr Tyr Gly His Asp Gly Phe Leu Tyr Trp Gly Gln
            100                 105                 110

Gly Thr Leu Val Thr Val Ser Ser
        115                 120

<210> SEQ ID NO 66
<211> LENGTH: 108
<212> TYPE: PRT
<213> ORGANISM: Artificial sequence
<220> FEATURE:
<223> OTHER INFORMATION: Synthetic

<400> SEQUENCE: 66

Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asp Val Val Thr Thr
            20                  25                  30

Val Ala Trp Tyr Gln Gln Lys Pro Gly Lys Ala Pro Lys Leu Leu Ile
        35                  40                  45

Tyr Trp Ala Ser Leu Arg His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Phe Cys Gln Gln Tyr Ser Ser Tyr Pro Tyr
                85                  90                  95

Thr Phe Gly Gln Gly Thr Lys Leu Glu Ile Lys Arg
            100                 105

<210> SEQ ID NO 67
<211> LENGTH: 330
<212> TYPE: PRT
<213> ORGANISM: homo sapiens

<400> SEQUENCE: 67

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ala Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Ala Ala Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 68
<211> LENGTH: 107
<212> TYPE: PRT
<213> ORGANISM: homo sapiens

<400> SEQUENCE: 68

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu

```
                65                  70                  75                  80
Lys His Lys Val Tyr Ala Cys Glu Val Thr His Gln Gly Leu Ser Ser
                        85                  90                  95

Pro Val Thr Lys Ser Phe Asn Arg Gly Glu Cys
                100                 105

<210> SEQ ID NO 69
<211> LENGTH: 330
<212> TYPE: PRT
<213> ORGANISM: homo sapiens

<400> SEQUENCE: 69

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```